US012559731B2

(12) United States Patent
Ihnken et al.

(10) Patent No.: US 12,559,731 B2
(45) Date of Patent: Feb. 24, 2026

(54) MUTATED PglB OLIGOSACCHARYL TRANSFERASE ENZYMES

(71) Applicant: GlaxoSmithKline Biologicals SA, Rixensart (BE)

(72) Inventors: Leigh Anne Ihnken, Collegeville, PA (US); Joel Karpiak, Collegeville, PA (US); Stefan Jochen Kemmler, Schlieren (CH); Michael Thomas Kowarik, Schlieren (CH); Joel Melby, Collegeville, PA (US); Anne Ollis, Collegeville, PA (US); Julien Laurent Quebatte, Schlieren (CH)

(73) Assignee: GlaxoSmithKline Biologicals SA, Rixensart (BE)

( * ) Notice: Subject to any disclaimer, the term of this patent is extended or adjusted under 35 U.S.C. 154(b) by 784 days.

(21) Appl. No.: 17/630,488

(22) PCT Filed: Aug. 6, 2020

(86) PCT No.: PCT/EP2020/072102
§ 371 (c)(1),
(2) Date: Jan. 26, 2022

(87) PCT Pub. No.: WO2021/028303
PCT Pub. Date: Feb. 18, 2021

(65) Prior Publication Data
US 2022/0403347 A1    Dec. 22, 2022

Related U.S. Application Data

(60) Provisional application No. 62/884,791, filed on Aug. 9, 2019, provisional application No. 62/931,265, filed on Nov. 6, 2019.

(51) Int. Cl.
*C12N 9/10* (2006.01)

(52) U.S. Cl.
CPC .... *C12N 9/1048* (2013.01); *C12Y 204/99019* (2015.07)

(58) Field of Classification Search
CPC ...................... C12N 9/1048; C12Y 204/99019
See application file for complete search history.

(56) References Cited

FOREIGN PATENT DOCUMENTS

| | | | |
|---|---|---|---|
| AU | 2009215341 B2 | 8/2009 | |
| WO | 2009104074 A2 | 8/2009 | |
| WO | 2011106389 A1 | 9/2011 | |
| WO | 2012150034 A1 | 11/2012 | |
| WO | 2013067523 A1 | 5/2013 | |
| WO | WO-2014114926 A1 | 7/2014 | |
| WO | 2016023018 A2 | 2/2016 | |
| WO | WO-2016107818 A1 * | 7/2016 | ........... C12N 9/1081 |

OTHER PUBLICATIONS

Napiorkowska et al., "Molecular basis of lipid-linked oligosaccharide recognition and processing by bacterial oligosaccharyltransferase." Nature Structure and Molecular Biology. 24:12: 1100-1108 (Year: 2015).*
Ollis et al., "Substitute Sweeteners: diverse bacterial oligosaccharyltransferases with unique N-gylcosylation site preferences." Scientific Reports. 5:15237, 1-13. (Year: 2015).*
Siloto et al., "Site saturation mutagenesis: Methods and applicationsin protein engineering." Biocatalysis andAgriculturalBiotechnology. 1:181-189 (Year: 2012).*
Singh RK et al. Protein Engineering Approaches in the Post-Genomic Era. 2017. Current Protein and Peptide Science. 18, 1-11. (Year: 2017).*
Zhang M et al. Propagated Perturbations from a Peripheral Mutation Show Interactions Supporting WW Domain Thermostability. 2018, Structure, 26, 1474-1485. (Year: 2018).*
Barre, Yasmin, et al., "A conserved DGGK motif is essential for the function of the PglB oligosaccharyltransferase from Campylobacter jejuni", Glycobiology, Oct. 1, 2017;27(10):978-989.
Lai-Xi Wang et al: "Chemical and Chemoenzymatic Synthesis of Glycoproteins for Deciphering Functions", Chemistry and Biology., vol. 21, No. 1. Jan. 1, 2014 (Jan. 1, 2014), pp. 51-66, XP055452263, GB ISSN: 1074-5521, DOI: 10.1016/j.chembiol.2014.01.001, p. 55.
Decision of Rejection for Chinese Application No. CN20208056352, mailed Sep. 27, 2024, 12 Pages.
Jejuni Campylobacter: "Peptide-Binding Protein [Campylobacter Jejuni]—Protein—NCBI Peptide-Binding Protein [Campylobacter Jejuni]," Jun. 10, 2017, XP055734424, Retrieved on Sep. 28, 2020, Retrieved from URL: www.ncbi.nlm.nih.gov/protein/WP_0877227621.
Partial European Search Report for European Application No. 24171392.4, mailed Aug. 7, 2024, 12 Pages.

* cited by examiner

*Primary Examiner* — Paul J Holland

(57) ABSTRACT

The present disclosure provides mutated PglB oligosaccharyltransferase enzymes that have the ability to efficiently catalyze the transfer of a saccharide from a lipid carrier to an asparagine reissue in a glycosylation motif on a protein. Also provided are polynucleotides encoding the mutated PglB oligosaccharyltransferase enzymes, host cells capable of expressing the engineered PglB oligosaccharyltransferase enzymes, and methods of using the engineered PglB oligosaccharyltransferase enzymes to make N-glycosylated proteins. Also provided are N-glycosylated proteins that are made using the engineered PglB oligosaccharyltransferase enzymes.

9 Claims, 8 Drawing Sheets
Specification includes a Sequence Listing.

A

B

| C. jejuni PglB variant | | inactive | wt | N311V | N311V Y77R | N311V Y77R A57R | A57R;Y77R; N311V;N30 0L;L301P;F3 08W;Y46Z W;H479M;L S70K | Rd4 | Rd5 | Rd6 | Rd7 | |
|---|---|---|---|---|---|---|---|---|---|---|---|---|
| Fold improvement (ELISA) | | | | | 5.8 | 2.8 | 18.1 | 4.5 | 2.7 | 1.2 | 1.0 | cumulative 4343 fold |

A

B

ELISA

WB α22F

A

B

*Sp23A*

*Sp35B*

Cieslewicz et al., Structural
and Genetic Diversity of Group
B Streptococcus Capsular
Polysaccharides, I&I, 2005
May;73(5):3096-103. DOI:
https://doi.org/10.1128/IAI.73
.5.3096-3103.2005

Figure 7

SEQUENCE LISTING

<160> NUMBER OF SEQ ID NOS: 15

<210> SEQ ID NO 1
<211> LENGTH: 713
<212> TYPE: PRT
<213> ORGANISM: Campylobacter jejuni

<400> SEQUENCE: 1

Met Leu Lys Lys Glu Tyr Leu Lys Asn Pro Tyr Leu Val Leu Phe Ala
1               5                   10                  15

-continued

```
Met Ile Ile Leu Ala Tyr Val Phe Ser Val Phe Cys Arg Phe Tyr Trp
        20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
            115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
    210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
    290                 295                 300

Phe Met Tyr Phe Asn Val Asn Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
    370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430
```

-continued

```
Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Tyr Pro Val
        450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
            515                 520                 525

Met Met Lys Asp Tyr Asn Gln Ser Asn Val Asp Leu Phe Leu Ala Ser
    530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
            595                 600                 605

Leu Ser Asn Gly Val Val Leu Ser Asp Asp Phe Arg Ser Phe Lys Ile
    610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
            675                 680                 685

Leu Gly Asn Tyr Asp Lys Asn Leu Phe Asp Leu Val Ile Asn Ser Arg
    690                 695                 700

Asp Ala Lys Val Phe Lys Leu Lys Ile
705                 710

<210> SEQ ID NO 2
<211> LENGTH: 713
<212> TYPE: PRT
<213> ORGANISM: Campylobacter jejuni

<400> SEQUENCE: 2

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Arg Tyr Gly Ser
65                  70                  75                  80

Ser Leu Ser Ala Leu Thr Tyr Trp Leu Tyr Lys Ile Thr Pro Phe Ser
                85                  90                  95
```

-continued

```
Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
            115                 120                 125

Gly Phe Val Ala Ala Leu Leu Ala Ser Ile Ala Asn Ser Tyr Tyr Asn
            130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
            195                 200                 205

Leu Ile Tyr Thr Leu Ile Phe His Arg Lys Glu Lys Ile Phe Tyr Ile
            210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
            275                 280                 285

Lys Phe Tyr Ile Phe Arg Ser Asp Glu Ser Ala Asn Leu Thr Gln Gly
            290                 295                 300

Phe Met Tyr Phe Asn Val Val Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
            370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
                420                 425                 430

Phe Ser Gln Asn Glu Ala Ser Leu Leu Asn Gln Leu Lys Asn Ile Ala
            435                 440                 445

Asn Arg Glu Asp Tyr Val Val Thr Trp Trp Asp Tyr Gly Tyr Pro Val
            450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
                500                 505                 510
```

-continued

```
Phe Tyr Ala Pro Gln Asn Asp Ile Leu Lys Thr Asp Ile Leu Gln Ala
        515                 520                 525

Met Met Lys Asp Tyr Asn Gln Ser Asn Val Asp Leu Phe Leu Ala Ser
    530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
        595                 600                 605

Leu Ser Asn Gly Val Val Leu Ser Asp Asp Phe Arg Ser Phe Lys Ile
    610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
                660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
    690                 695                 700

Asp Ala Lys Val Phe Lys Leu Lys Ile
705                 710

<210> SEQ ID NO 3
<211> LENGTH: 713
<212> TYPE: PRT
<213> ORGANISM: Campylobacter jejuni

<400> SEQUENCE: 3

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Arg Phe Ala Glu Gly Ala Arg Asp
    50                  55                  60

Met Ile Ala Gly Phe His Gln Pro Asn Asp Leu Ser Arg Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175
```

```
Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
            195                 200                 205

Leu Ile Tyr Thr Leu Ile Phe His Arg Lys Glu Lys Ile Phe Tyr Ile
            210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
            275                 280                 285

Lys Phe Tyr Ile Phe Arg Ser Asp Glu Ser Ala Asn Leu Thr Gln Gly
            290                 295                 300

Phe Met Tyr Phe Asn Val Val Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
            370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
            435                 440                 445

Asn Arg Glu Asp Tyr Val Val Thr Trp Trp Asp Tyr Gly Tyr Pro Val
            450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
            515                 520                 525

Met Met Lys Asp Tyr Asn Gln Ser Asn Val Asp Leu Phe Leu Ala Ser
            530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590
```

```
Thr Phe Ser Thr Ala Tyr Pro Leu Asp Val Lys Asn Gly Glu Ile Tyr
        595                 600                 605

Leu Ser Asn Gly Val Val Leu Ser Asp Asp Phe Arg Ser Phe Lys Ile
        610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
                660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
        690                 695                 700

Asp Ala Lys Val Phe Lys Leu Lys Ile
705                 710

<210> SEQ ID NO 4
<211> LENGTH: 713
<212> TYPE: PRT
<213> ORGANISM: Campylobacter jejuni

<400> SEQUENCE: 4

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
                20                  25                  30

Val Trp Trp Ala Ser Glu Phe Asn Glu Tyr Phe Phe Asn Asn Gln Leu
                35                  40                  45

Met Ile Ile Ser Asn Asp Gly Tyr Arg Phe Ala Glu Gly Ala Arg Asp
        50                  55                  60

Met Ile Ala Gly Phe His Gln Pro Asn Asp Leu Ser Arg Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
                100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
        130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
                180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
        210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255
```

```
Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
            275                 280                 285

Lys Phe Tyr Ile Phe Arg Ser Asp Glu Ser Ala Leu Pro Thr Gln Gly
            290                 295                 300

Phe Met Tyr Trp Asn Val Val Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
                340                 345                 350

Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
    370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
                420                 425                 430

Phe Ser Gln Asn Glu Ala Ser Leu Leu Asn Gln Leu Lys Asn Ile Ala
            435                 440                 445

Asn Arg Glu Asp Tyr Val Val Thr Trp Trp Asp Tyr Gly Trp Pro Val
    450                 455                 460

Arg Tyr Tyr Ser Asp Val Lys Thr Leu Val Asp Gly Gly Lys Met Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
            515                 520                 525

Met Met Lys Asp Tyr Asn Gln Ser Asn Val Asp Leu Phe Leu Ala Ser
    530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Arg Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
            595                 600                 605

Leu Ser Asn Gly Val Val Leu Ser Asp Asp Phe Arg Ser Phe Lys Ile
    610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670
```

-continued

```
Leu Met Asp Lys Thr Met Phe Asn Ser Ala Tyr Val Gln Met Phe Phe
        675             680             685

Leu Gly Asn Tyr Asp Lys Asn Leu Phe Asp Leu Val Ile Asn Ser Arg
        690             695             700

Asp Ala Lys Val Phe Lys Leu Lys Ile
705             710

<210> SEQ ID NO 5
<211> LENGTH: 713
<212> TYPE: PRT
<213> ORGANISM: Campylobacter jejuni

<400> SEQUENCE: 5

Met Leu Lys Lys Glu Tyr Leu Lys Asn Pro Tyr Leu Val Leu Phe Ala
1               5               10              15

Met Ile Ile Leu Ala Tyr Val Phe Ser Val Phe Cys Arg Phe Tyr Trp
        20              25              30

Val Trp Trp Ala Ser Glu Phe Asn Glu Tyr Phe Phe Asn Asn Gln Leu
        35              40              45

Met Ile Ile Ser Asn Asp Gly Tyr Arg Phe Ala Glu Gly Ala Arg Asp
        50              55              60

Met Ile Ala Gly Phe His Gln Pro Asn Asp Leu Ser Arg Tyr Gly Ser
65              70              75              80

Ser Leu Ser Ala Leu Thr Tyr Trp Leu Tyr Lys Ile Thr Pro Phe Ser
                85              90              95

Phe Glu Ser Ile Ile Leu Tyr Met Ser Thr Phe Leu Ser Ser Leu Val
            100             105             110

Val Ile Pro Thr Ile Leu Leu Ala Asn Glu Tyr Lys Arg Pro Leu Met
        115             120             125

Gly Phe Val Ala Ala Leu Leu Ala Ser Ile Ala Asn Ser Tyr Tyr Asn
        130             135             140

Arg Thr Met Ser Gly Tyr Tyr Asp Thr Asp Met Leu Val Ile Val Leu
145             150             155             160

Pro Met Phe Ile Leu Phe Phe Met Val Arg Met Ile Leu Lys Lys Asp
                165             170             175

Phe Phe Ser Leu Ile Ala Leu Pro Leu Phe Ile Gly Ile Tyr Tyr Trp
            180             185             190

Trp Tyr Pro Ser Ser Tyr Thr Leu Asn Val Ala Leu Ile Gly Leu Phe
            195             200             205

Leu Ile Tyr Thr Leu Ile Phe His Arg Lys Glu Lys Ile Phe Tyr Ile
        210             215             220

Ala Val Ile Leu Ser Ser Leu Thr Leu Ser Asn Ile Ala Trp Phe Tyr
225             230             235             240

Gln Ser Ala Ile Ile Val Ile Leu Phe Ala Leu Phe Ala Leu Glu Gln
                245             250             255

Lys Arg Leu Asn Phe Met Ile Ile Gly Ile Leu Gly Ser Ala Thr Leu
            260             265             270

Ile Phe Leu Ile Leu Ser Gly Gly Val Asp Pro Ile Leu Gln Gln Leu
        275             280             285

Lys Phe Tyr Ile Phe Arg Leu Asp Glu Ser Ala Leu Pro Thr Gln Gly
        290             295             300

Phe Met Tyr Trp Asn Val Val Gln Thr Ile Gln Glu Val Glu Asn Val
305             310             315             320

Asp Leu Ser Glu Phe Met Arg Arg Ile Ser Gly Ser Glu Ile Val Phe
            325             330             335
```

-continued

```
Leu Phe Ser Leu Phe Gly Phe Val Trp Leu Leu Arg Lys His Lys Ser
        340             345                 350

Met Ile Met Ala Leu Pro Ile Leu Val Leu Gly Phe Leu Ala Leu Lys
        355             360                 365

Gly Gly Leu Arg Phe Thr Ile Tyr Ser Val Pro Val Met Ser Leu Gly
        370             375             380

Phe Gly Phe Leu Leu Ser Glu Phe Lys Ala Ile Met Val Lys Lys Tyr
385             390                 395                 400

Ser Gln Leu Thr Ser Asn Val Cys Ile Val Phe Ala Thr Ile Leu Thr
            405             410                 415

Leu Ala Pro Val Phe Ile His Ile Tyr Asn Tyr Lys Ala Pro Thr Val
        420             425                 430

Phe Ser Gln Asn Glu Ala Ser Leu Leu Asn Gln Leu Lys Asn Ile Ala
        435             440                 445

Asn Arg Glu Asp Tyr Val Val Thr Trp Trp Asp Tyr Gly Trp Pro Val
    450             455                 460

Arg Tyr Tyr Ser Asp Val Lys Thr Leu Val Asp Gly Gly Lys Met Leu
465             470                 475                 480

Gly Arg Asp Asn Phe Phe Pro Ser Phe Ala Leu Ser Lys Asp Glu Gln
            485             490                 495

Ala Ala Ala Asn Met Ala Arg Leu Ser Val Glu Tyr Thr Glu Lys Ser
        500             505                 510

Phe Tyr Ala Pro Gln Asn Asp Ile Leu Lys Arg Asp Ile Leu Gln Ala
        515             520                 525

Met Met Lys Asp Tyr Asn Gln Ser Asn Val Asp Leu Phe Leu Ala Ser
    530             535                 540

Leu Ser Lys Pro Asp Phe Lys Ile Asp Thr Pro Lys Thr Arg Asp Ile
545             550                 555                 560

Tyr Leu Tyr Met Pro Ala Arg Met Ser Arg Ile Phe Ser Thr Val Ala
            565             570                 575

Ser Phe Ser Phe Ile Asn Leu Asp Thr Gly Val Leu Asp Lys Pro Phe
            580             585                 590

Thr Phe Ser Thr Ala Tyr Pro Leu Asp Val Lys Asn Gly Glu Ile Tyr
            595             600                 605

Leu Ser Asn Gly Val Val Leu Ser Asp Asp Phe Arg Ser Phe Lys Ile
        610             615                 620

Gly Asp Asn Val Val Ser Val Asn Ser Ile Val Glu Ile Asn Ser Ile
625             630                 635                 640

Lys Gln Gly Glu Tyr Lys Ile Thr Pro Ile Asp Asp Lys Ala Gln Phe
            645             650                 655

Tyr Ile Phe Tyr Leu Lys Asp Ser Ala Ile Pro Tyr Ala Gln Phe Ile
            660             665                 670

Leu Met Asp Lys Thr Met Phe Asn Ser Ala Tyr Val Gln Met Phe Phe
            675             680                 685

Leu Gly Asn Tyr Asp Lys Asn Leu Phe Asp Leu Val Ile Asn Ser Arg
        690             695                 700

Asp Ala Lys Val Phe Lys Leu Lys Ile
705             710
```

<210> SEQ ID NO 6
<211> LENGTH: 713
<212> TYPE: PRT
<213> ORGANISM: Campylobacter jejuni -continued

<400> SEQUENCE: 6

```
Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
            35                  40                  45

Met Ile Ile Ser Asn Asp Gly Tyr Arg Phe Ala Glu Gly Ala Arg Asp
        50                  55                  60

Met Ile Ala Gly Phe His Gln Pro Asn Asp Leu Ser Arg Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
                100                 105                 110

Val Ile Pro Thr Ile Leu Leu Ala Asn Glu Tyr Lys Arg Pro Leu Met
                115                 120                 125

Gly Phe Val Ala Ala Leu Leu Ala Ser Ile Ala Asn Ser Tyr Tyr Asn
        130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Tyr Trp
                180                 185                 190

Trp Tyr Pro Ser Ser Tyr Thr Leu Asn Val Ala Leu Ile Gly Leu Phe
                195                 200                 205

Leu Ile Tyr Thr Leu Ile Phe His Arg Lys Glu Lys Ile Phe Tyr Ile
        210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
                260                 265                 270

Ile Phe Leu Ile Leu Ser Gly Gly Val Asp Pro Ile Leu Gln Gln Leu
                275                 280                 285

Lys Phe Tyr Ile Phe Arg Leu Asp Arg Ser Ala Leu Pro Thr Gln Gly
        290                 295                 300

Phe Met Tyr Trp Asn Val Val Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
                340                 345                 350

Met Ile Met Ala Leu Pro Ile Leu Val Leu Gly Phe Leu Ala Leu Lys
                355                 360                 365

Gly Gly Leu Arg Phe Thr Ile Tyr Ser Val Pro Val Met Ser Leu Gly
        370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415
```

-continued

```
Leu Ala Pro Val Phe Ile His Ile Tyr Asn Tyr Lys Ala Pro Thr Val
        420                 425                 430

Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Trp Pro Val
        450                 455                 460

Arg Tyr Tyr Ser Asp Val Lys Thr Leu Val Asp Gly Gly Lys Met Leu
465                 470                 475                 480

Gly Arg Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
        500                 505                 510

Phe Tyr Ala Pro Gln Asn Asp Ile Leu Lys Arg Asp Ile Leu Gln Ala
        515                 520                 525

Met Met Lys Asp Tyr Asn Gln Ser Asn Val Asp Leu Phe Leu Ala Ser
        530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Arg Ile Phe Ser Thr Val Ala
                565                 570                 575

Ser Phe Ser Phe Ile Asn Leu Asp Thr Gly Val Leu Asp Lys Pro Phe
                580                 585                 590

Thr Phe Ser Thr Ala Tyr Pro Leu Asp Val Lys Asn Gly Glu Ile Tyr
        595                 600                 605

Leu Ser Asn Gly Val Val Leu Ser Asp Asp Phe Arg Ser Phe Lys Ile
        610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
                660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
        690                 695                 700

Asp Ala Lys Val Phe Lys Leu Lys Ile
705                 710
```

```
<210> SEQ ID NO 7
<211> LENGTH: 713
<212> TYPE: PRT
<213> ORGANISM: Campylobacter jejuni

<400> SEQUENCE: 7
```

```
Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
        20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Arg Phe Ala Glu Gly Ala Arg Asp
        50                  55                  60

Met Ile Ala Gly Phe His Gln Pro Asn Asp Leu Ser Arg Tyr Gly Asp
```

-continued

```
65                    70                    75                    80

Ser Leu Ser Ala Leu Thr Tyr Trp Leu Tyr Lys Ile Thr Pro Phe Ser
                85                    90                    95

Phe Glu Ser Ile Ile Leu Tyr Met Ser Thr Phe Leu Ser Ser Leu Val
               100                   105                   110

Val Ile Pro Thr Ile Leu Leu Ala Asn Glu Tyr Lys Arg Pro Leu Met
               115                   120                   125

Gly Phe Val Ala Ala Leu Leu Ala Ser Ile Ala Asn Ser Tyr Tyr Asn
           130                   135                   140

Arg Thr Met Ser Gly Tyr Tyr Asp Thr Asp Met Leu Val Ile Val Leu
       145                   150                   155                   160

Pro Met Phe Ile Leu Phe Phe Met Val Arg Met Ile Leu Lys Lys Asp
                   165                   170                   175

Phe Phe Ser Leu Ile Ala Leu Pro Leu Phe Ile Gly Ile Tyr Tyr Trp
               180                   185                   190

Trp Tyr Pro Ser Ser Tyr Thr Leu Asn Val Ala Leu Ile Gly Leu Phe
               195                   200                   205

Leu Ile Tyr Thr Leu Ile Phe His Arg Lys Glu Lys Ile Phe Tyr Ile
       210                   215                   220

Ala Val Ile Leu Ser Ser Leu Thr Leu Ser Asn Ile Ala Trp Phe Tyr
225                   230                   235                   240

Gln Ser Ala Ile Ile Val Ile Leu Phe Ala Leu Phe Ala Leu Glu Gln
               245                   250                   255

Lys Arg Leu Asn Phe Met Ile Ile Gly Ile Leu Gly Ser Ala Thr Leu
               260                   265                   270

Ile Phe Leu Ile Leu Ser Gly Gly Val Asp Pro Ile Leu Gln Gln Leu
           275                   280                   285

Lys Phe Tyr Ile Phe Arg Leu Asp Arg Ser Ala Leu Pro Thr Gln Gly
       290                   295                   300

Phe Met Tyr Trp Asn Val Val Gln Thr Ile Gln Glu Val Glu Asn Val
305                   310                   315                   320

Asp Leu Ser Glu Phe Met Arg Arg Ile Ser Gly Ser Glu Ile Val Phe
               325                   330                   335

Leu Phe Ser Leu Phe Gly Phe Val Trp Leu Leu Arg Lys His Lys Ser
           340                   345                   350

Met Ile Met Ala Leu Pro Ile Leu Val Leu Gly Phe Leu Ala Leu Lys
           355                   360                   365

Gly Gly Leu Arg Phe Thr Ile Tyr Ser Val Pro Val Met Ser Leu Gly
       370                   375                   380

Phe Gly Phe Leu Leu Ser Glu Phe Lys Ala Ile Met Val Lys Lys Tyr
385                   390                   395                   400

Ser Gln Leu Thr Ser Asn Val Cys Ile Val Phe Ala Thr Ile Leu Thr
               405                   410                   415

Leu Ala Pro Val Phe Ile His Ile Tyr Asn Tyr Lys Ala Pro Thr Val
               420                   425                   430

Phe Ser Gln Asn Glu Ala Ser Leu Leu Asn Gln Leu Lys Asn Ile Ala
           435                   440                   445

Asn Arg Glu Asp Tyr Val Val Thr Trp Trp Asp Tyr Gly Trp Pro Val
       450                   455                   460

Arg Tyr Tyr Ser Asp Val Lys Thr Leu Val Asp Gly Gly Lys Met Leu
465                   470                   475                   480

Gly Arg Asp Asn Phe Phe Pro Ser Phe Ala Leu Ser Lys Asp Glu Gln
               485                   490                   495
```

-continued

```
Ala Ala Ala Asn Met Ala Arg Leu Ser Val Glu Tyr Thr Glu Lys Ser
        500             505             510

Phe Tyr Ala Pro Gln Asn Asp Ile Leu Lys Arg Asp Ile Leu Gln Ala
        515             520             525

Met Met Lys Asp Tyr Asn Gln Ser Asn Val Asp Leu Phe Leu Ala Ser
        530             535             540

Leu Ser Lys Pro Asp Phe Lys Ile Asp Thr Pro Lys Thr Arg Asp Ile
545             550             555             560

Tyr Leu Tyr Met Pro Ala Arg Met Ser Arg Ile Phe Ser Thr Val Ala
            565             570             575

Ser Phe Ser Phe Ile Asn Leu Asp Thr Gly Val Leu Asp Lys Pro Phe
            580             585             590

Thr Phe Ser Thr Ala Tyr Pro Leu Asp Val Lys Asn Gly Glu Ile Tyr
        595             600             605

Leu Ser Asn Gly Val Val Leu Ser Asp Asp Phe Arg Ser Phe Lys Ile
        610             615             620

Gly Asp Asn Val Val Ser Val Asn Ser Ile Val Glu Ile Asn Ser Ile
625             630             635             640

Lys Gln Gly Glu Tyr Lys Ile Thr Pro Ile Asp Asp Lys Ala Gln Phe
            645             650             655

Tyr Ile Phe Tyr Leu Lys Asp Ser Ala Ile Pro Tyr Ala Gln Phe Ile
            660             665             670

Leu Met Asp Lys Thr Met Phe Asn Ser Ala Tyr Val Gln Met Phe Phe
        675             680             685

Leu Gly Asn Tyr Asp Lys Asn Leu Phe Asp Leu Val Ile Asn Ser Arg
        690             695             700

Asp Ala Lys Val Phe Lys Leu Lys Ile
705             710

<210> SEQ ID NO 8
<211> LENGTH: 713
<212> TYPE: PRT
<213> ORGANISM: Campylobacter jejuni

<400> SEQUENCE: 8

Met Leu Lys Lys Glu Tyr Leu Lys Asn Pro Tyr Leu Val Leu Phe Ala
1               5               10              15

Met Ile Ile Leu Ala Tyr Val Phe Ser Val Phe Cys Arg Phe Tyr Trp
        20              25              30

Val Trp Trp Ala Ser Glu Phe Asn Glu Tyr Phe Phe Asn Asn Gln Leu
        35              40              45

Met Ile Ile Ser Asn Asp Gly Tyr Arg Phe Ala Glu Gly Ala Arg Asp
        50              55              60

Met Ile Ala Gly Phe His Gln Pro Asn Asp Leu Ser Arg Tyr Gly Asp
65              70              75              80

Ser Leu Ser Ala Leu Thr Tyr Trp Leu Tyr Lys Ile Thr Pro Phe Ser
            85              90              95

Phe Glu Ser Ile Ile Leu Tyr Met Ser Thr Phe Leu Ser Ser Leu Val
            100             105             110

Val Ile Pro Thr Ile Leu Leu Ala Asn Glu Tyr Lys Arg Pro Leu Met
        115             120             125

Gly Phe Val Ala Ala Leu Leu Ala Ser Ile Ala Asn Ser Tyr Tyr Asn
        130             135             140

Arg Thr Met Ser Gly Tyr Tyr Asp Thr Asp Met Leu Val Ile Val Leu
```

-continued

```
145                150                155                160

Pro Met Phe Ile Leu Phe Phe Met Val Arg Met Ile Leu Lys Lys Asp
               165                170                175

Phe Phe Ser Leu Ile Ala Leu Pro Leu Phe Val Gly Ile Tyr Tyr Trp
               180                185                190

Trp Tyr Pro Ser Ser Tyr Thr Leu Asn Val Ala Leu Ile Gly Leu Phe
           195                200                205

Leu Ile Tyr Thr Leu Ile Phe His Arg Lys Glu Lys Ile Phe Tyr Ile
       210                215                220

Ala Val Ile Leu Ser Ser Leu Thr Leu Ser Asn Ile Ala Trp Phe Tyr
225                230                235                240

Gln Ser Ala Ile Ile Val Ile Leu Phe Ala Leu Phe Ala Leu Glu Gln
               245                250                255

Lys Arg Leu Asn Phe Met Ile Ile Gly Ile Leu Gly Ser Ala Thr Leu
               260                265                270

Ile Phe Leu Ile Leu Ser Gly Gly Val Asp Pro Ile Leu Gln Gln Leu
           275                280                285

Lys Phe Tyr Ile Phe Arg Leu Asp Arg Ser Ala Leu Pro Thr Gln Gly
       290                295                300

Phe Met Tyr Trp Asn Val Val Gln Thr Ile Gln Glu Val Glu Asn Val
305                310                315                320

Asp Leu Ser Glu Phe Met Arg Arg Ile Ser Gly Ser Glu Ile Val Phe
               325                330                335

Leu Phe Ser Leu Phe Gly Phe Val Trp Leu Leu Arg Lys His Lys Ser
               340                345                350

Met Ile Met Ala Leu Pro Gln Leu Val Leu Gly Phe Leu Ala Leu Lys
           355                360                365

Gly Gly Leu Arg Phe Thr Ile Tyr Ser Val Pro Val Met Ser Leu Gly
       370                375                380

Phe Gly Phe Leu Leu Ser Glu Phe Lys Ala Ile Met Val Lys Lys Tyr
385                390                395                400

Ser Gln Leu Thr Ser Ile Val Cys Ile Val Phe Ala Thr Ile Leu Thr
               405                410                415

Leu Ala Pro Val Phe Ile His Ile Tyr Asn Tyr Lys Ala Pro Thr Val
               420                425                430

Phe Ser Gln Asn Glu Ala Ser Leu Leu Asn Gln Leu Lys Asn Ile Ala
           435                440                445

Asn Arg Glu Asp Tyr Val Val Thr Trp Trp Asp Tyr Gly Trp Pro Val
       450                455                460

Arg Tyr Tyr Ser Asp Val Lys Thr Leu Val Asp Gly Gly Lys Met Leu
465                470                475                480

Gly Arg Asp Asn Phe Phe Pro Ser Phe Ala Leu Ser Lys Asp Glu Gln
               485                490                495

Ala Ala Ala Asn Met Ala Arg Leu Ser Val Glu Tyr Thr Glu Lys Ser
           500                505                510

Phe Tyr Ala Pro Gln Asn Asp Ile Leu Lys Arg Asp Ile Leu Gln Ala
       515                520                525

Met Met Lys Asp Tyr Asn Gln Ser Asn Val Asp Leu Phe Leu Ala Ser
       530                535                540

Leu Ser Lys Pro Asp Phe Lys Ile Asp Thr Pro Lys Thr Arg Asp Ile
545                550                555                560

Tyr Leu Tyr Met Pro Ala Arg Met Ser Arg Ile Phe Ser Thr Val Ala
               565                570                575
```

-continued

```
Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
            595                 600                 605

Leu Ser Asn Gly Val Val Leu Ser Asp Asp Phe Arg Ser Phe Lys Ile
        610                 615                 620

Gly Asp Asn Val Val Ser Val Asn Ser Ile Val Glu Ile Asn Ser Ile
    625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
            675                 680                 685

Leu Gly Asn Tyr Asp Lys Asn Leu Phe Asp Leu Val Ile Asn Ser Arg
        690                 695                 700

Asp Ala Lys Val Phe Lys Leu Lys Ile
705                 710
```

```
<210> SEQ ID NO 9
<211> LENGTH: 722
<212> TYPE: PRT
<213> ORGANISM: Campylobacter jejuni

<400> SEQUENCE: 9
```

```
Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
            195                 200                 205

Leu Ile Tyr Thr Leu Ile Phe His Arg Lys Glu Lys Ile Phe Tyr Ile
        210                 215                 220

Ala Val Ile Leu Ser Ser Leu Thr Leu Ser Asn Ile Ala Trp Phe Tyr
```

-continued

```
225                230                235                240

Gln Ser Ala Ile Ile Val Ile Leu Phe Ala Leu Phe Ala Leu Glu Gln
               245                250                255

Lys Arg Leu Asn Phe Met Ile Ile Gly Ile Leu Gly Ser Ala Thr Leu
               260                265                270

Ile Phe Leu Ile Leu Ser Gly Gly Val Asp Pro Ile Leu Tyr Gln Leu
               275                280                285

Lys Phe Tyr Ile Phe Arg Ser Asp Glu Ser Ala Asn Leu Thr Gln Gly
               290                295                300

Phe Met Tyr Phe Asn Val Asn Gln Thr Ile Gln Glu Val Glu Asn Val
305                310                315                320

Asp Leu Ser Glu Phe Met Arg Arg Ile Ser Gly Ser Glu Ile Val Phe
               325                330                335

Leu Phe Ser Leu Phe Gly Phe Val Trp Leu Leu Arg Lys His Lys Ser
               340                345                350

Met Ile Met Ala Leu Pro Ile Leu Val Leu Gly Phe Leu Ala Leu Lys
               355                360                365

Gly Gly Leu Arg Phe Thr Ile Tyr Ser Val Pro Val Met Ala Leu Gly
               370                375                380

Phe Gly Phe Leu Leu Ser Glu Phe Lys Ala Ile Met Val Lys Lys Tyr
385                390                395                400

Ser Gln Leu Thr Ser Asn Val Cys Ile Val Phe Ala Thr Ile Leu Thr
               405                410                415

Leu Ala Pro Val Phe Ile His Ile Tyr Asn Tyr Lys Ala Pro Thr Val
               420                425                430

Phe Ser Gln Asn Glu Ala Ser Leu Leu Asn Gln Leu Lys Asn Ile Ala
               435                440                445

Asn Arg Glu Asp Tyr Val Val Thr Trp Trp Asp Tyr Gly Tyr Pro Val
               450                455                460

Arg Tyr Tyr Ser Asp Val Lys Thr Leu Val Asp Gly Gly Lys His Leu
465                470                475                480

Gly Lys Asp Asn Phe Phe Pro Ser Phe Ala Leu Ser Lys Asp Glu Gln
               485                490                495

Ala Ala Ala Asn Met Ala Arg Leu Ser Val Glu Tyr Thr Glu Lys Ser
               500                505                510

Phe Tyr Ala Pro Gln Asn Asp Ile Leu Lys Thr Asp Ile Leu Gln Ala
               515                520                525

Met Met Lys Asp Tyr Asn Gln Ser Asn Val Asp Leu Phe Leu Ala Ser
               530                535                540

Leu Ser Lys Pro Asp Phe Lys Ile Asp Thr Pro Lys Thr Arg Asp Ile
545                550                555                560

Tyr Leu Tyr Met Pro Ala Arg Met Ser Leu Ile Phe Ser Thr Val Ala
               565                570                575

Ser Phe Ser Phe Ile Asn Leu Asp Thr Gly Val Leu Asp Lys Pro Phe
               580                585                590

Thr Phe Ser Thr Ala Tyr Pro Leu Asp Val Lys Asn Gly Glu Ile Tyr
               595                600                605

Leu Ser Asn Gly Val Val Leu Ser Asp Asp Phe Arg Ser Phe Lys Ile
               610                615                620

Gly Asp Asn Val Val Ser Val Asn Ser Ile Val Glu Ile Asn Ser Ile
625                630                635                640

Lys Gln Gly Glu Tyr Lys Ile Thr Pro Ile Asp Asp Lys Ala Gln Phe
               645                650                655
```

```
Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
            675                 680                 685

Leu Gly Asn Tyr Asp Lys Asn Leu Phe Asp Leu Val Ile Asn Ser Arg
            690                 695                 700

Asp Ala Lys Val Phe Lys Leu Lys Ile Tyr Pro Tyr Asp Val Pro Asp
705                 710                 715                 720

Tyr Ala

<210> SEQ ID NO 10
<211> LENGTH: 712
<212> TYPE: PRT
<213> ORGANISM: Campylobacter lari

<400> SEQUENCE: 10

Met Lys Leu Gln Gln Asn Phe Thr Asp Asn Asn Ser Ile Lys Tyr Thr
1               5                   10                  15

Cys Ile Leu Ile Leu Ile Ala Phe Ala Phe Ser Val Leu Cys Arg Leu
            20                  25                  30

Tyr Trp Val Ala Trp Ala Ser Glu Phe Tyr Glu Phe Phe Phe Asn Asp
            35                  40                  45

Gln Leu Met Ile Thr Thr Asn Asp Gly Tyr Ala Phe Ala Glu Gly Ala
            50                  55                  60

Arg Asp Met Ile Ala Gly Phe His Gln Pro Asn Asp Leu Ser Tyr Phe
65                  70                  75                  80

Gly Ser Ser Leu Ser Thr Leu Thr Tyr Trp Leu Tyr Ser Ile Leu Pro
            85                  90                  95

Phe Ser Phe Glu Ser Ile Ile Leu Tyr Met Ser Ala Phe Phe Ala Ser
            100                 105                 110

Leu Ile Val Val Pro Ile Ile Leu Ile Ala Arg Glu Tyr Lys Leu Thr
            115                 120                 125

Thr Tyr Gly Phe Ile Ala Ala Leu Leu Gly Ser Ile Ala Asn Ser Tyr
            130                 135                 140

Tyr Asn Arg Thr Met Ser Gly Tyr Tyr Asp Thr Asp Met Leu Val Leu
145                 150                 155                 160

Val Leu Pro Met Leu Ile Leu Leu Thr Phe Ile Arg Leu Thr Ile Asn
            165                 170                 175

Lys Asp Ile Phe Thr Leu Leu Leu Ser Pro Val Phe Ile Met Ile Tyr
            180                 185                 190

Leu Trp Trp Tyr Pro Ser Ser Tyr Ser Leu Asn Phe Ala Met Ile Gly
            195                 200                 205

Leu Phe Gly Leu Tyr Thr Leu Val Phe His Arg Lys Glu Lys Ile Phe
            210                 215                 220

Tyr Leu Thr Ile Ala Leu Met Ile Ile Ala Leu Ser Met Leu Ala Trp
225                 230                 235                 240

Gln Tyr Lys Leu Ala Leu Ile Val Leu Leu Phe Ala Ile Phe Ala Phe
            245                 250                 255

Lys Glu Glu Lys Ile Asn Phe Tyr Met Ile Trp Ala Leu Ile Phe Ile
            260                 265                 270

Ser Ile Leu Ile Leu His Leu Ser Gly Gly Leu Asp Pro Val Leu Tyr
            275                 280                 285

Gln Leu Lys Phe Tyr Val Phe Lys Ala Ser Asp Val Gln Asn Leu Lys
            290                 295                 300
```

-continued

```
Asp Ala Ala Phe Met Tyr Phe Asn Val Asn Glu Thr Ile Met Glu Val
305                 310                 315                 320

Asn Thr Ile Asp Pro Glu Val Phe Met Gln Arg Ile Ser Ser Ser Val
                325                 330                 335

Leu Val Phe Ile Leu Ser Phe Ile Gly Phe Ile Leu Leu Cys Lys Asp
                340                 345                 350

His Lys Ser Met Leu Leu Ala Leu Pro Met Leu Ala Leu Gly Phe Met
                355                 360                 365

Ala Leu Arg Ala Gly Leu Arg Phe Thr Ile Tyr Ala Val Pro Val Met
                370                 375                 380

Ala Leu Gly Phe Gly Tyr Phe Leu Tyr Ala Phe Phe Asn Phe Leu Glu
385                 390                 395                 400

Lys Lys Gln Ile Lys Leu Ser Leu Arg Asn Lys Asn Ile Leu Leu Ile
                405                 410                 415

Leu Ile Ala Phe Phe Ser Ile Ser Pro Ala Leu Met His Ile Tyr Tyr
                420                 425                 430

Tyr Lys Ser Ser Thr Val Phe Thr Ser Tyr Glu Ala Ser Ile Leu Asn
                435                 440                 445

Asp Leu Lys Asn Lys Ala Gln Arg Glu Asp Tyr Val Val Ala Trp Trp
    450                 455                 460

Asp Tyr Gly Tyr Pro Ile Arg Tyr Tyr Ser Asp Val Lys Thr Leu Ile
465                 470                 475                 480

Asp Gly Gly Lys His Leu Gly Lys Asp Asn Phe Phe Ser Ser Phe Val
                485                 490                 495

Leu Ser Lys Glu Gln Ile Pro Ala Ala Asn Met Ala Arg Leu Ser Val
                500                 505                 510

Glu Tyr Thr Glu Lys Ser Phe Lys Glu Asn Tyr Pro Asp Val Leu Lys
                515                 520                 525

Ala Met Val Lys Asp Tyr Asn Lys Thr Ser Ala Lys Asp Phe Leu Glu
    530                 535                 540

Ser Leu Asn Asp Lys Asp Phe Lys Phe Asp Thr Asn Lys Thr Arg Asp
545                 550                 555                 560

Val Tyr Ile Tyr Met Pro Tyr Arg Met Leu Arg Ile Met Pro Val Val
                565                 570                 575

Ala Gln Phe Ala Asn Thr Asn Pro Asp Asn Gly Glu Gln Glu Lys Ser
                580                 585                 590

Leu Phe Phe Ser Gln Ala Asn Ala Ile Ala Gln Asp Lys Thr Thr Gly
                595                 600                 605

Ser Val Met Leu Asp Asn Gly Val Glu Ile Ile Asn Asp Phe Arg Ala
    610                 615                 620

Leu Lys Val Glu Gly Ala Ser Ile Pro Leu Lys Ala Phe Val Asp Ile
625                 630                 635                 640

Glu Ser Ile Thr Asn Gly Lys Phe Tyr Tyr Asn Glu Ile Asp Ser Lys
                645                 650                 655

Ala Gln Ile Tyr Leu Leu Phe Leu Arg Glu Tyr Lys Ser Phe Val Ile
                660                 665                 670

Leu Asp Glu Ser Leu Tyr Asn Ser Ser Tyr Ile Gln Met Phe Leu Leu
                675                 680                 685

Asn Gln Tyr Asp Gln Asp Leu Phe Glu Gln Ile Thr Asn Asp Thr Arg
    690                 695                 700

Ala Lys Ile Tyr Arg Leu Lys Arg
705                 710
```

-continued

```
<210> SEQ ID NO 11
<211> LENGTH: 713
<212> TYPE: PRT
<213> ORGANISM: Campylobacter jejuni

<400> SEQUENCE: 11

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser His Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
            165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
            195                 200                 205

Leu Ile Tyr Thr Leu Ile Phe His Arg Lys Glu Lys Ile Phe Tyr Ile
        210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
        290                 295                 300

Phe Met Tyr Phe Asn Val Val Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
    370                 375                 380
```

-continued

```
Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
                420                 425                 430

Phe Ser Gln Asn Glu Ala Ser Leu Leu Asn Gln Leu Lys Asn Ile Ala
                435                 440                 445

Asn Arg Glu Asp Tyr Val Val Thr Trp Trp Asp Tyr Gly Tyr Pro Val
        450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
                500                 505                 510

Phe Tyr Ala Pro Gln Asn Asp Ile Leu Lys Thr Asp Ile Leu Gln Ala
                515                 520                 525

Met Met Lys Asp Tyr Asn Gln Ser Asn Val Asp Leu Phe Leu Ala Ser
        530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
                580                 585                 590

Thr Phe Ser Thr Ala Tyr Pro Leu Asp Val Lys Asn Gly Glu Ile Tyr
                595                 600                 605

Leu Ser Asn Gly Val Val Leu Ser Asp Asp Phe Arg Ser Phe Lys Ile
        610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
                660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
        690                 695                 700

Asp Ala Lys Val Phe Lys Leu Lys Ile
705                 710
```

```
<210> SEQ ID NO 12
<211> LENGTH: 714
<212> TYPE: PRT
<213> ORGANISM: Campylobacter coli

<400> SEQUENCE: 12
```

```
Met Leu Lys Lys Glu Tyr Phe Lys Asn Pro Thr Phe Ile Leu Leu Ala
1               5                   10                  15

Phe Ile Ile Leu Ala Tyr Val Phe Ser Val Leu Cys Arg Phe Tyr Trp
                20                  25                  30

Ile Phe Trp Ala Ser Glu Phe Asn Glu Tyr Phe Phe Asn Asn Glu Leu
```

-continued

```
              35                    40                    45

Met Ile Ile Ser Asn Asp Gly Tyr Ala Phe Ala Glu Gly Ala Arg Asp
    50                    55                    60

Met Ile Ala Gly Phe His Gln Pro Asn Asp Leu Ser Tyr Tyr Gly Ser
65                70                    75                    80

Ser Leu Ser Thr Leu Thr Tyr Trp Phe Tyr Lys Ile Thr Pro Phe Ser
                  85                    90                    95

Leu Glu Ser Ile Phe Ile Tyr Ile Ser Thr Phe Leu Ser Ser Leu Val
              100                   105                   110

Val Ile Pro Leu Ile Leu Ile Ala Asn Glu Tyr Lys Arg Pro Leu Met
              115                   120                   125

Gly Phe Val Ala Ala Leu Leu Ala Ser Ile Ala Asn Ser Tyr Tyr Asn
              130                   135                   140

Arg Thr Met Ser Gly Tyr Tyr Asp Thr Asp Met Leu Val Ile Val Leu
145                   150                   155                   160

Ala Met Met Ile Val Phe Phe Met Ile Arg Leu Ile Leu Lys Lys Asp
              165                   170                   175

Leu Leu Ser Leu Ile Thr Leu Pro Leu Phe Val Gly Ile Tyr Leu Trp
              180                   185                   190

Trp Tyr Pro Ser Ser Tyr Thr Leu Asn Val Ala Leu Leu Gly Leu Phe
              195                   200                   205

Phe Ile Tyr Thr Leu Val Phe His Ile Lys Glu Lys Thr Leu Tyr Met
              210                   215                   220

Ala Ile Ile Leu Ala Ser Ile Thr Leu Ser Asn Ile Ala Trp Phe Tyr
225                   230                   235                   240

Gln Ser Ala Ile Ile Val Ile Leu Phe Ser Leu Phe Val Leu Gln Asn
                  245                   250                   255

Lys Arg Phe Ser Phe Ala Leu Leu Gly Ile Leu Gly Leu Ala Thr Leu
              260                   265                   270

Val Phe Leu Ile Leu Ser Gly Gly Ile Asp Pro Ile Leu Tyr Gln Leu
              275                   280                   285

Lys Phe Tyr Ile Phe Arg Ser Asp Glu Ser Ala Asn Leu Ala Gln Gly
    290                   295                   300

Phe Met Tyr Phe Asn Val Asn Gln Thr Ile Gln Glu Val Glu Ser Ile
305                   310                   315                   320

Asp Leu Ser Ile Phe Met Gln Arg Ile Ser Gly Ser Glu Leu Val Phe
              325                   330                   335

Phe Val Ser Leu Ile Gly Phe Ile Phe Leu Val Arg Lys His Lys Ser
              340                   345                   350

Met Ile Leu Ala Leu Pro Met Leu Ala Leu Gly Phe Leu Ala Leu Lys
              355                   360                   365

Ser Gly Leu Arg Phe Thr Ile Tyr Ala Val Pro Val Leu Ala Leu Gly
    370                   375                   380

Phe Gly Phe Leu Met Ser Leu Leu Gln Glu Arg Lys Gln Lys Asn Asn
385                   390                   395                   400

Asn Thr Tyr Trp Trp Ala Asn Ile Gly Val Phe Ile Phe Thr Phe Leu
                  405                   410                   415

Ser Leu Ile Pro Met Phe Tyr His Ile Asn Asn Tyr Lys Ala Pro Thr
              420                   425                   430

Val Phe Ser Gln Asn Glu Ala Thr Lys Leu Asp Glu Leu Lys Lys Ile
              435                   440                   445

Ala Gln Arg Glu Asp Tyr Val Val Thr Trp Trp Asp Tyr Gly Tyr Pro
    450                   455                   460
```

-continued

```
Ile Arg Tyr Tyr Ser Asp Val Lys Thr Leu Ala Asp Gly Gly Lys His
465             470              475             480

Leu Gly Lys Asp Asn Phe Phe Pro Ser Phe Val Leu Ser Lys Asp Gln
            485              490             495

Val Ala Ala Ala Asn Met Ala Arg Leu Ser Val Glu Tyr Thr Glu Lys
            500              505             510

Ser Phe Tyr Ala Pro Leu Asn Asp Ile Leu Lys Asn Asp Leu Leu Gln
            515              520             525

Ala Met Met Lys Asp Tyr Asn Gln Asn Asn Val Asp Leu Phe Leu Ala
            530              535             540

Ser Leu Ser Lys Pro Asp Phe Lys Ile Asn Met Pro Lys Thr Arg Asp
545             550              555             560

Val Tyr Ile Tyr Met Pro Ala Arg Met Ser Leu Ile Phe Ser Thr Val
                565              570             575

Ala Ser Phe Ser Phe Val Asp Leu Glu Thr Gly Glu Ile Asn Lys Pro
                580              585             590

Phe Thr Phe Ser Ala Ala Tyr Pro Leu Asp Val Lys Asn Gly Glu Ile
                595              600             605

Tyr Leu Ser Asn Gly Ile Ala Leu Ser Asp Asp Phe Arg Ser Phe Lys
            610              615             620

Ile Asn Asn Ser Thr Ile Ser Val Asn Ser Ile Ile Glu Ile Asn Ser
625             630              635             640

Ile Lys Gln Gly Glu Tyr Lys Ile Thr Pro Ile Asp Asp Met Ala Gln
                645              650             655

Phe Tyr Ile Phe Tyr Leu Lys Asp Ser Thr Ile Pro Tyr Ala Gln Phe
                660              665             670

Ile Leu Met Asp Lys Thr Met Phe Asn Ser Ala Tyr Val Gln Met Phe
                675              680             685

Phe Leu Gly Asn Tyr Asp Lys Asn Leu Tyr Asp Leu Val Ile Asn Ala
            690              695             700

Arg Asp Ala Lys Val Phe Lys Leu Lys Ile
705                 710
```

```
<210> SEQ ID NO 13
<211> LENGTH: 711
<212> TYPE: PRT
<213> ORGANISM: Campylobacter coli

<400> SEQUENCE: 13
```

```
Met Leu Lys Lys Glu Tyr Phe Lys Asn Pro Thr Phe Ile Leu Leu Thr
1               5               10              15

Leu Ile Ile Leu Ala Tyr Ala Phe Ser Val Leu Cys Arg Phe Tyr Trp
            20              25              30

Val Phe Trp Ala Ser Glu Phe Asn Glu Tyr Phe Phe Asn Asn Glu Leu
            35              40              45

Met Ile Ile Ser Asn Asp Gly Tyr Ala Phe Ala Glu Gly Ala Arg Asp
            50              55              60

Met Ile Ala Gly Phe His Gln Pro Asn Asp Leu Ser Tyr Tyr Gly Ser
65              70              75              80

Ser Leu Ser Thr Leu Thr Tyr Trp Phe Tyr Lys Ile Thr Pro Phe Ser
                85              90              95

Leu Glu Ser Ile Phe Ile Tyr Ile Ser Thr Phe Leu Ser Ser Leu Val
            100             105             110

Val Val Pro Leu Ile Leu Ile Ala Asn Glu Tyr Lys Arg Pro Leu Met
```

```
                115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Ala Met Met Ile Val Phe Phe Met Ile Arg Leu Ile Leu Arg Lys Asp
                165                 170                 175

Leu Leu Ser Leu Ile Ala Leu Pro Leu Phe Val Gly Ile Tyr Leu Trp
                180                 185                 190

Trp Tyr Pro Ser Ser Tyr Thr Leu Asn Val Ala Leu Leu Gly Leu Leu
                195                 200                 205

Phe Ile Tyr Thr Leu Val Phe His Ile Lys Glu Lys Thr Leu Tyr Met
    210                 215                 220

Ala Ile Ile Leu Ala Ser Ile Thr Leu Ser Asn Ile Ala Trp Phe Tyr
225                 230                 235                 240

Gln Ser Ala Ile Ile Val Ile Leu Phe Ser Leu Phe Val Leu Gln Asn
                245                 250                 255

Lys Arg Phe Ser Phe Ala Leu Leu Gly Phe Leu Gly Leu Ala Thr Leu
                260                 265                 270

Val Phe Leu Ile Leu Ser Gly Gly Val Asp Pro Ile Leu Tyr Gln Leu
                275                 280                 285

Lys Phe Tyr Ile Phe Arg Ser Asp Glu Ser Ala Asn Leu Ala Gln Gly
    290                 295                 300

Phe Met Tyr Phe Asn Val Asn Gln Thr Ile Gln Glu Val Glu Ser Ile
305                 310                 315                 320

Asp Leu Ser Ile Phe Met Lys Arg Ile Ser Gly Ser Glu Leu Val Phe
                325                 330                 335

Phe Ile Ser Leu Ile Gly Phe Ile Phe Leu Val Arg Lys His Lys Ser
                340                 345                 350

Met Ile Leu Ala Leu Pro Met Leu Ala Leu Gly Phe Leu Ala Leu Lys
                355                 360                 365

Gly Gly Leu Arg Phe Thr Ile Tyr Ala Val Pro Val Leu Ala Leu Gly
    370                 375                 380

Phe Gly Phe Leu Met Ser Leu Leu Gln Glu Arg Lys Trp Lys Asn Lys
385                 390                 395                 400

Asn Ile Tyr Trp Ala Ser Val Ser Ile Phe Thr Phe Leu Ser Leu Leu
                405                 410                 415

Pro Met Phe Tyr His Ile Ile Asn Tyr Lys Ala Pro Thr Val Phe Ser
                420                 425                 430

Gln Asn Glu Ala Ser Lys Leu Asp Glu Leu Lys Lys Ile Ala Gln Arg
    435                 440                 445

Glu Asp Tyr Val Val Ala Trp Trp Asp Tyr Gly Tyr Pro Ile Arg Tyr
    450                 455                 460

Tyr Ser Asp Val Lys Thr Leu Ala Asp Gly Gly Lys His Leu Gly Lys
465                 470                 475                 480

Asp Asn Phe Phe Pro Ser Phe Ile Leu Ser Lys Asp Gln Thr Ala Ala
                485                 490                 495

Ala Asn Met Ala Arg Leu Ser Val Glu Tyr Thr Glu Lys Ser Phe Tyr
                500                 505                 510

Ala Pro Ser Asn Asp Ile Leu Lys Asn Asp Leu Leu Lys Ala Met Met
                515                 520                 525

Lys Asp Tyr Lys Gln Asn Asn Val Asp Leu Phe Leu Ala Ser Leu Ser
    530                 535                 540
```

-continued

```
Lys Pro Asp Phe Lys Ile Asn Thr Pro Lys Thr Arg Asp Val Tyr Ile
545                 550                 555                 560

Tyr Met Pro Ala Arg Met Ser Leu Ile Phe Ser Thr Val Ala Ser Phe
                565                 570                 575

Ser Phe Val Asp Leu Asp Thr Gly Lys Ile Asp Lys Pro Phe Thr Phe
                580                 585                 590

Ser Ala Ala Tyr Pro Leu Asp Val Lys Asn Gly Glu Ile Tyr Leu Ser
            595                 600                 605

Asn Gly Ile Val Leu Ser Asp Asp Phe Arg Ser Phe Lys Ile Asn His
        610                 615                 620

Asn Thr Ile Pro Val Asn Ser Ile Ile Glu Val Ser Ser Ile Lys Gln
625                 630                 635                 640

Gly Glu Tyr Lys Ile Thr Pro Ile Asp Asp Thr Ala Gln Phe Tyr Ile
                645                 650                 655

Leu Tyr Leu Lys Asp Ser Thr Ile Pro Tyr Ala Gln Phe Ile Leu Met
                660                 665                 670

Asp Lys Ala Met Phe Asn Ser Ala Tyr Val Gln Met Phe Phe Leu Gly
            675                 680                 685

Asn Tyr Asp Lys Asn Leu Tyr Asp Leu Val Ile Asn Thr Arg Asp Thr
        690                 695                 700

Lys Val Phe Lys Leu Lys Ile
705                 710
```

<210> SEQ ID NO 14
<211> LENGTH: 714
<212> TYPE: PRT
<213> ORGANISM: Campylobacter coli

<400> SEQUENCE: 14

```
Met Leu Lys Lys Glu Tyr Phe Lys Asn Pro Thr Phe Ile Leu Leu Ala
1               5                   10                  15

Phe Ile Ile Leu Ala Tyr Val Phe Ser Val Leu Cys Arg Phe Tyr Trp
                20                  25                  30

Val Phe Trp Ala Ser Glu Phe Asn Glu Tyr Phe Phe Asn Asn Glu Leu
            35                  40                  45

Met Ile Ile Ser Asn Asp Gly Tyr Ala Phe Ala Glu Gly Ala Arg Asp
        50                  55                  60

Met Ile Ala Gly Phe His Gln Pro Asn Asp Leu Ser Tyr Tyr Gly Ser
65                  70                  75                  80

Ser Leu Ser Thr Leu Thr Tyr Trp Phe Tyr Lys Ile Thr Pro Phe Ser
                85                  90                  95

Leu Glu Ser Ile Phe Ile Tyr Ile Ser Thr Phe Leu Ser Ser Leu Val
                100                 105                 110

Val Ile Pro Leu Ile Leu Ile Ala Asn Glu Tyr Lys Arg Pro Leu Met
            115                 120                 125

Gly Phe Val Ala Ala Leu Leu Ala Ser Ile Ala Asn Ser Tyr Tyr Asn
        130                 135                 140

Arg Thr Met Ser Gly Tyr Tyr Asp Thr Asp Met Leu Val Ile Val Leu
145                 150                 155                 160

Ala Met Met Ile Val Phe Phe Met Ile Arg Leu Ile Leu Lys Lys Asp
                165                 170                 175

Leu Leu Ser Leu Ile Ala Leu Pro Leu Phe Val Gly Ile Tyr Leu Trp
            180                 185                 190

Trp Tyr Pro Ser Ser Tyr Thr Leu Asn Val Ala Leu Leu Gly Leu Phe
```

-continued

```
            195                  200                  205
Phe Ile Tyr Thr Leu Val Phe His Ile Lys Glu Lys Thr Leu Tyr Met
    210                  215                  220

Ala Ile Ile Leu Ala Ser Ile Thr Leu Ser Asn Ile Ala Trp Phe Tyr
225                  230                  235                  240

Gln Ser Ala Ile Ile Val Ile Leu Phe Ser Leu Phe Val Leu Gln Asn
                    245                  250                  255

Lys Arg Phe Ser Phe Ala Leu Leu Gly Ile Leu Gly Leu Ala Thr Leu
                260                  265                  270

Val Phe Leu Ile Leu Ser Gly Gly Ile Asp Pro Ile Leu Tyr Gln Leu
                275                  280                  285

Lys Phe Tyr Ile Phe Arg Ser Asp Glu Ser Ala Asn Leu Ala Gln Gly
    290                  295                  300

Phe Met Tyr Phe Asn Val Asn Gln Thr Ile Gln Glu Val Glu Ser Ile
305                  310                  315                  320

Asp Leu Ser Ile Phe Met Gln Arg Ile Ser Gly Ser Glu Leu Val Phe
                325                  330                  335

Phe Val Ser Leu Ile Gly Phe Ile Phe Leu Val Arg Lys His Lys Ser
                340                  345                  350

Met Ile Leu Ala Leu Pro Met Leu Ala Leu Gly Phe Leu Ala Leu Lys
                355                  360                  365

Ser Gly Leu Arg Phe Thr Ile Tyr Ala Val Pro Val Leu Ala Leu Gly
    370                  375                  380

Phe Gly Phe Leu Met Ser Leu Leu Gln Glu Arg Lys Gln Lys Asn Asn
385                  390                  395                  400

Asn Thr Tyr Trp Trp Ala Asn Ile Gly Val Phe Ile Phe Thr Phe Leu
                405                  410                  415

Ser Leu Ile Pro Met Phe Tyr His Ile Asn Asn Tyr Lys Ala Pro Thr
                420                  425                  430

Val Phe Ser Gln Asn Glu Ala Thr Lys Leu Asp Glu Leu Lys Lys Ile
                435                  440                  445

Ala Gln Arg Glu Asp Tyr Val Val Ala Trp Trp Asp Tyr Gly Tyr Pro
    450                  455                  460

Ile Arg Tyr Tyr Ser Asp Val Lys Thr Leu Ala Asp Gly Gly Lys His
465                  470                  475                  480

Leu Gly Lys Asp Asn Phe Phe Pro Ser Phe Val Leu Ser Lys Asp Gln
                485                  490                  495

Val Ala Ala Ala Asn Met Ala Arg Leu Ser Val Glu Tyr Thr Glu Lys
                500                  505                  510

Ser Phe Tyr Ala Pro Leu Asn Asp Ile Leu Lys Asn Asp Leu Leu Gln
    515                  520                  525

Ala Met Met Lys Asp Tyr Asn Gln Asn Asn Val Asp Leu Phe Leu Ala
    530                  535                  540

Leu Leu Ser Lys Pro Asp Phe Lys Ile Asn Thr Pro Lys Thr Arg Asp
545                  550                  555                  560

Val Tyr Ile Tyr Met Pro Ala Arg Met Ser Leu Ile Phe Ser Thr Val
                565                  570                  575

Ala Ser Phe Ser Phe Val Asp Leu Gly Thr Gly Glu Ile Asn Lys Pro
                580                  585                  590

Phe Thr Phe Ser Ala Ala Tyr Pro Leu Asp Val Lys Asn Gly Glu Ile
                595                  600                  605

Tyr Leu Ser Asn Gly Ile Val Leu Ser Asp Asp Phe Arg Ser Phe Lys
    610                  615                  620
```

-continued

```
Ile Asn Asn Ser Thr Ile Ser Val Asn Ser Ile Ile Glu Ile Asn Ser
625             630             635             640

Ile Lys Gln Gly Glu Tyr Lys Ile Thr Pro Ile Asp Asp Thr Ala Gln
                645             650             655

Phe Tyr Ile Phe Tyr Leu Lys Asp Ser Thr Ile Pro Tyr Ala Gln Phe
            660             665             670

Ile Leu Met Asp Lys Thr Met Phe Asn Ser Ala Tyr Val Gln Met Phe
        675             680             685

Phe Leu Gly Asn Tyr Asp Lys Asn Leu Tyr Asp Leu Val Ile Asn Ala
    690             695             700

Arg Asp Ala Lys Val Phe Lys Leu Lys Phe
705             710
```

```
<210> SEQ ID NO 15
<211> LENGTH: 5
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa can be Asp or Glu
<220> FEATURE:
<221> NAME/KEY: MISC_FEATURE
<222> LOCATION: (2)..(2)
<223> OTHER INFORMATION: Xaa can be any naturally occuring amino acid
      except proline
<220> FEATURE:
<221> NAME/KEY: MISC_FEATURE
<222> LOCATION: (4)..(4)
<223> OTHER INFORMATION: Xaa can be any naturally occuring amino acid
      except proline
<220> FEATURE:
<221> NAME/KEY: MISC_FEATURE
<222> LOCATION: (5)..(5)
<223> OTHER INFORMATION: Xaa can be Ser or Thr

<400> SEQUENCE: 15

Xaa Xaa Asn Xaa Xaa
1               5
```

MUTATED PglB OLIGOSACCHARYL TRANSFERASE ENZYMES

CROSS-REFERENCE TO RELATED APPLICATIONS

This application is filed pursuant to 35 U.S.C. § 371 as a United States National Phase Application of International Application No. PCT/EP2020/072102 filed Aug. 6, 2020 which claims priority from U.S. Provisional No. 62/884,791 filed Aug. 9, 2019 and U.S. Provisional No. 62/931,265 filed Nov. 6, 2019.

FIELD OF THE INVENTION

The present invention relates to improved PglB oligosaccharyl transferases and their use in the glycosylation of proteins and/or the production of carrier proteins conjugated to saccharide chains. The invention also includes polynucleotides encoding the improved PglB oligosaccharyl transferases and host cells comprising said polynucleotides.

BACKGROUND OF THE INVENTION

Glycoconjugate vaccines are widely recognized for their ability to prevent many life-threatening bacterial infections. Glycoconjugate vaccines are generally considered efficacious and safe and have been used in humans for over 30 years. Conventional glycovaccine production often involves the chemical modification of immunogenic carrier proteins with polysaccharide antigens of pathogenic bacteria. However, more recently, biotechnological processes for producing glycoconjugate vaccines have emerged that are expected to reduce production costs and to further increase the homogeneity and possibly the potency and safety of glyco-conjugate vaccine preparations.

In eukaryotic cells, N-linked glycosylation is a key post-translational protein modification mechanism involving several enzymes. In prokaryotic cells N-linked glycosylation is catalyzed by certain bacterial N-oligosaccharyltransferases (N-OSTs). The protein glycosylation gene cluster of *Campylobacter jejuni* (*C. jejuni*) includes the pglB gene, which encodes a membrane-bound N-OST (PglB$_{Cj}$). PglB can be expressed in standard bacterial hosts, such as *Escherichia coli* (*E. coli*), and can glycosylate co-expressed periplasmic proteins that carry at least one surface-exposed D/E-Z$_1$-N-Z$_2$-S/T (Z$_1$ and Z$_2 \neq$P) glycosylation motif. PglB can transfer bacterial polysaccharide antigens to certain *C. jejuni* proteins as well as to immunogenic carrier proteins of other organisms containing engineered glycosylation sites. PglB can transfer oligosaccharides and, to a certain degree, O-antigen lipopolysaccharide structures of Gram-negative bacteria and capsular antigen polysaccharides of Gram-positive bacteria. However, the efficiency of the oligosaccharyl transferase activity of PglB can vary depending on the nature of the saccharide being covalently bonded to a protein containing the required consensus sequence. There is therefore a need for improved PglB proteins which are capable of catalyzing the efficient transfer of saccharides with a different structure to those transferred in *C. jejuni*, to a protein containing the required glycosylation motif.

The present disclosure provides engineered PglB oligosaccharyltransferases which have been modified to improve the efficiency of PglB when transferring a range of saccharides which are not transferred to a protein in a *C. jejuni* cell.

Accordingly, there is provided a PglB oligosaccharyl-transferase (OST) polypeptide comprising an amino acid sequence that is at least 80%, 85%, 90%, 95%, 96%, 97%, 98%, or 99% identical to the amino acid sequence set out in SEQ ID NO: 1 or 2, or a functional fragment thereof, wherein the PglB oligosaccharyltransferase polypeptide amino acid sequence includes the feature that: at least one residue selected from the group consisting of amino acid 57, 63, 94, 101, 176, 191, 193, 233, 234, 286, 301, 319, 397, 402, 435, 446, 462, 479, 523, 532, 605, 610, 645, 676 and 695 is substituted to a different amino acid to that found at that position in SEQ ID NO:1 or 2. In a preferred embodiment, the amino acid sequence is at least 90% identical to SEQ ID NO:2.

In a second embodiment there is provided a polynucleotide encoding a mutated PglB oligosaccharyltransferase polypeptide of the invention.

In a third embodiment there is provided a composition or host cell (for example a prokaryotic host cell or an *E. coli* host cell) comprising at least one PglB oligosaccharyltrans-ferase of the invention or a polynucleotide encoding at least one PglB OST of the invention.

In a fourth embodiment there is provided process for preparing a glycosylated protein, comprising the steps of:
- (a) culturing a host cell of the invention, comprising the PglB of the invention and/or a polynucleotide encoding the PglB of the invention, under conditions suitable for the production of proteins; and
- (b) isolating the glycosylated protein from the host cell.

In a fifth embodiment there is provided an in vitro process for preparing a glycosylated protein, comprising the steps of;
- i) mixing together:
  - a) a PglB oligosaccharyltransferase of the invention;
  - b) a protein comprising at least one glycosylation consensus sequence comprising the amino acid sequence Asp/Glu-Z$_1$-Asn-Z$_2$-Ser/Thr wherein Z$_1$ and Z$_2$ may be any natural amino acid except Pro; and
  - c) a saccharide chain on a lipid carrier recognised by the PglB;
- ii) incubating under conditions suitable for the enzymatic activity of PglB to transfer the saccharide chain to the at least one glycosylation consensus sequence of the protein to achieve a glycosylated protein; and
- iii) isolating the glycosylated protein.

In a sixth embodiment there is provided a glycosylated protein that is made by the process of the invention.

In a seventh embodiment there is provided a use of the PglB oligosaccharyltransferase or functional fragment thereof of the invention in the production of a glycosylated protein in which a saccharide is attached to an N residue of a glycosylation consensus sequence, comprising the amino acid sequence Asp/Glu-Z$_1$-Asn-Z$_2$-Ser/Thr wherein Z$_1$ and Z$_2$ may be any natural amino acid except Pro, of a protein to form the glycosylated protein.

BRIEF DESCRIPTION OF THE FIGURES

FIG. 7—Alignment of amino acid sequences of PglB OST sequences from *Campylobacter coli* strains showing that EFM37568 is somewhat divergent, while EIA90085 and CDG57218 are more similar.

DETAILED DESCRIPTION OF THE INVENTION

Figure 1:
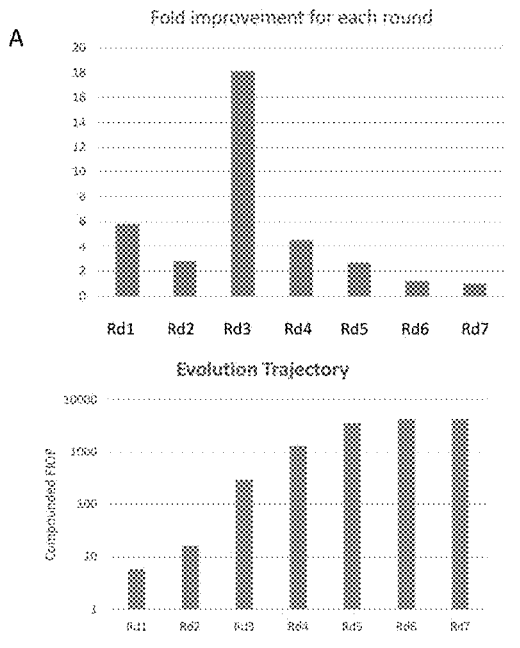
FIG. 1—Mutations in PglB result in higher oligosaccharyltransferase activity when transferring the capsular saccharide of *S. pneumoniae* serotype 8 to a protein. Panel A shows the compounded fold increase of production when PglB from round, 1, 2, 3, 4, 5, 6 and 7 are used to transfer the capsular saccharide of *S. pneumoniae* to an EPA carrier protein. Panel B shows a western blot and a Coomassie stained gel demonstrating the increase in EPA glycosylated with *S. pneumoniae* serotype 8 saccharide after different rounds of mutation. Panel C shows the Coomassie stained gel and western blots probed with an anti-*S. pneumoniae* serotype 8 antibody, demonstrating the increased production of conjugate containing *S. pneumoniae* serotype 8 saccharide following bioconjugation using point mutated PglB$_{Cj}$.
Figure 1:
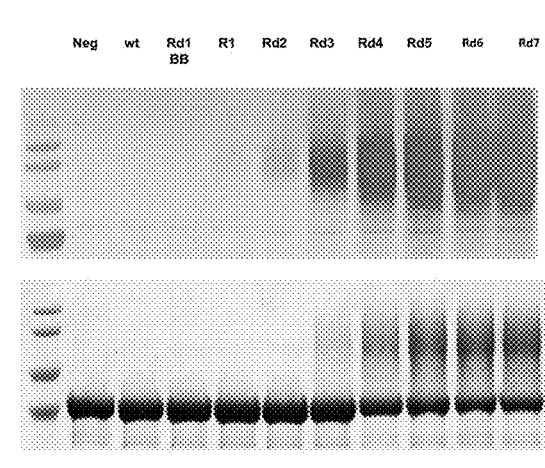
Figure 1C:
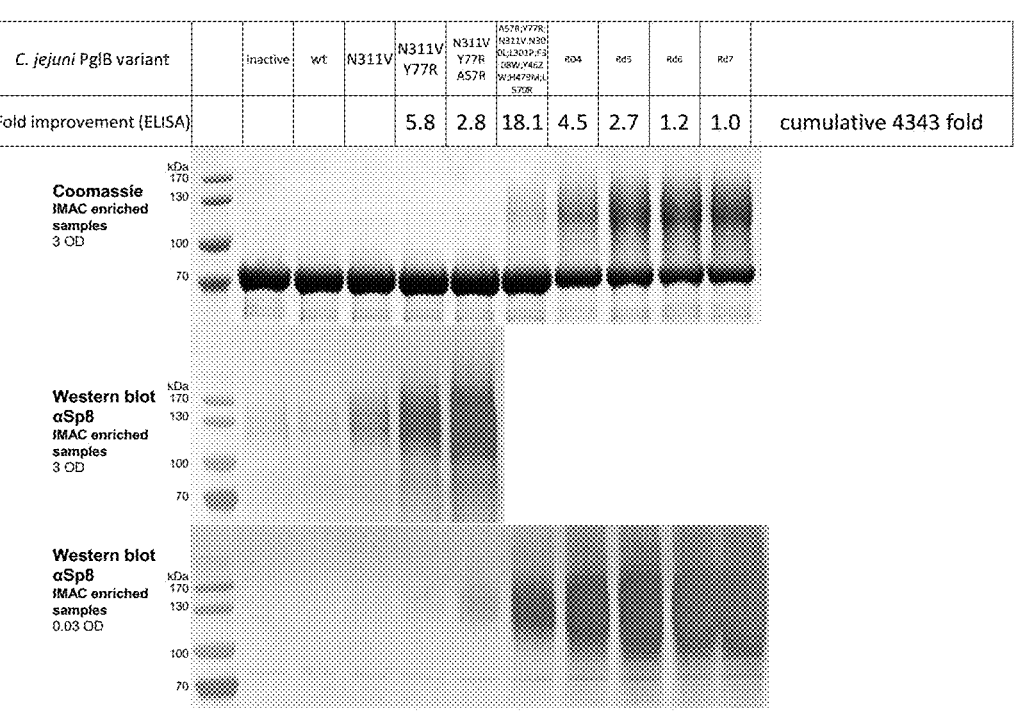
Figure 2:
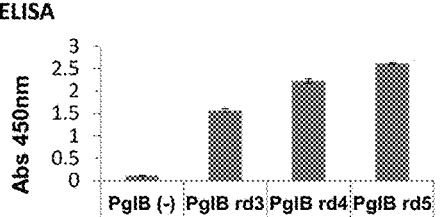
FIG. 2—The mutated PglBs also have increased activity for transfer of *S. pneumoniae* serotype 22F to a protein. Panel A shows ELISA results showing increased activity of the round 3, 4 and 5 PglBs in transferring the capsular saccharide of *S. pneumoniae* serotype 22F to a protein. Panel B shows western blot results of the increase in the production of EPA glycosylated with a serotype 22F capsular saccharide from the PglBs of round 3, 4 and 5.
Figure 2:
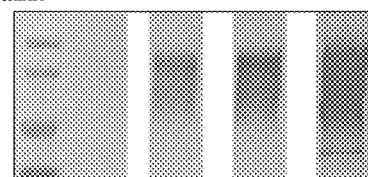

The present disclosure provides highly efficient PglB oligosaccharyltransferases capable of catalyzing the addition of saccharide to a protein containing at least one glycosylation consensus sequence of D/E-Z$_1$-N-Z$_2$-S/T (Z$_1$ and Z$_2$≠P). Such highly efficient PglB oligosaccharyltransferases are achieved by engineering the PglB. For example, through the selection of advantageous point mutations, either singly or in combination, which result in increased production of N-glycosylated protein.

Assays to confirm the activity of the PglB OSTs described herein are well known to skilled artisans (e.g., ELISA, Western Blot) and include the assays described in Examples 2 and 3. In some embodiments, the PglB OST is an engineered PglB which is optionally expressed in a host cell, optionally a heterologous host cell (i.e. a host cell which is not a *Campylobacter* cell).

The oligosaccharides and polysaccharides can include any oligosaccharide or polysaccharide described herein.

The carrier proteins can comprise any carrier protein described herein.

In some embodiments, the PglB OST comprises modifications (for example amino acids substitutions, or nucleotide substitutions in the polynucleotide encoding PglB) in, e.g., two or more, three or more, four or more, five or more, six or more, seven or more, eight or more, nine or more, or ten or more amino acids, for example 2-30, 3-25, 4-20, 5-20, 6-20, 7-20 or 10-20 amino acid substitution. In an embodiment, substitutions are at positions corresponding to the following residues of SEQ ID NO:1:

57; 77; 57 and 77; 311 and 77; 462 and 479 (mutations at both these positions synergise to increase activity of PglB); 57, 77 and 311; 57 and 462; 57, 462 and 479; 57, 462, 479, 77 and 311; 57, 462, 479, 300, 301, 308 and 570; 57, 462, 479, 300, 301, 308, 570 and 77; 57, 462, 479, 300, 301, 308, 570, 77 and 311.

In an embodiment, the following substitutions are present at positions corresponding to the following residues of SEQ ID NO:1 (where/denotes or):

A57R/T; Y77R; A57R/T and Y77R; A57R and Y77R; N311V and Y77R; Y462W and H479M (synergizing mutations); A57R/T, Y77R and N311V; A57R, Y77R and N311V; A57R/T and Y462P/C/W/T/N; A57R/T and Y462W/T/N; A57R and Y462W; Y462P/C/W/T/N and H479M (synergizing mutations); A57R/T, Y462P/C/W/T/N and H479M; A57R/T, Y462W/T/N and H479M; A57R, Y462W and H479M; A57R/T, Y462P/C/W/T/N, H479M, Y77R and N311V; A57R/T, Y462W/T/N, H479M, Y77R and N311V; A57R, Y462W, H479M, Y77R and N311V; A57R/T, Y462P/C/W/T/N, H479M, L301P/G/F and L570R/V; A57R, Y462W, H479M, L301P and L570R; A57R/T, Y462P/C/W/T/N, H479M, N300L, L301P/G/F, F308W/F and L570R/V; A57R, Y462W, H479M, N300L, L301P, F308W and L570R; A57R/T, Y462P/C/W/T/N, H479M, L301P/G/F, L570R/V and Y77R; A57R, Y462W, H479M, L301P, L570R and Y77R; A57R/T, Y462P/C/W/T/N, H479M, N300L, L301P/G/F, F308W/F, L570R/V and Y77R; A57R, Y462W, H479M, N300L, L301P, F308W, L570R and Y77R; A57R/T, Y462P/C/W/T/N, H479M, L301P/G/F, L570R/V, Y77R and N311V; A57R, Y462W, H479M, L301P, L570R, Y77R and N311V; A57R/T, Y462P/C/W/T/N, H479M, N300L, L301P/G/F, F308W/F, L570R/V, Y77R and N311V; A57R, Y462W, H479M, N300L, L301P, F308W, L570R, Y77R and N311V; A57R, Y462W, H479M, N300L, L301P, F308W, L570R, Y77R, S80D and N311V.

In some embodiments, a single point mutation in the engineered PglB can increase the efficiency of glycosylation of a carrier protein with a polysaccharide leading to an increase in comparative yield of glycosylated protein. An increase in comparative yield can be determined by dividing the yield of glycosylated protein produced by an engineered PglB OST containing a particular amino acid substitution with the yield of glycosylated protein produced by a corresponding PglB OST not containing that amino acid substitution. In an embodiment, the introduction of a single point mutation in the engineered PglB can increase the comparative yield by between about 1.1-fold and about 10-fold, by between about 1.2-fold and about 7-fold, by between about 1.3-fold and about 5-fold, by between about 1.5-fold and about 2.5-fold or by between about 1.5-fold and about 6-fold compared to the rate of a corresponding PglB lacking that particular point mutation. The positive effect of the single point mutations can multiply when combined as multiple point-mutations in a PglB. In some embodiments, the engineered PglB can contain at least 2, 3, 4, 5, 6, 7, 8, 9, 10, 11, 12, 13, 14, 15, 16, 17, 18, 19 or 20 amino acid substitutions that increase the comparative yield of glycosylated protein by more than 2-fold, more than 5-fold, more than 10-fold, more than 50-fold, more than 100-fold, more than 200-fold, more than 500-fold, more than 700-fold, more than 1,000-fold, more than 2,000-fold, more than 3,000-fold, more than 4,000-fold, more than 5,000-fold, more than 6,000-fold, more than 7,000-fold, more than 8,000-fold, more than 10,000-fold, compared to the yield obtained using the corresponding PglB in which the combination of point mutations have not been introduced (the original PglB).

Figure 5:
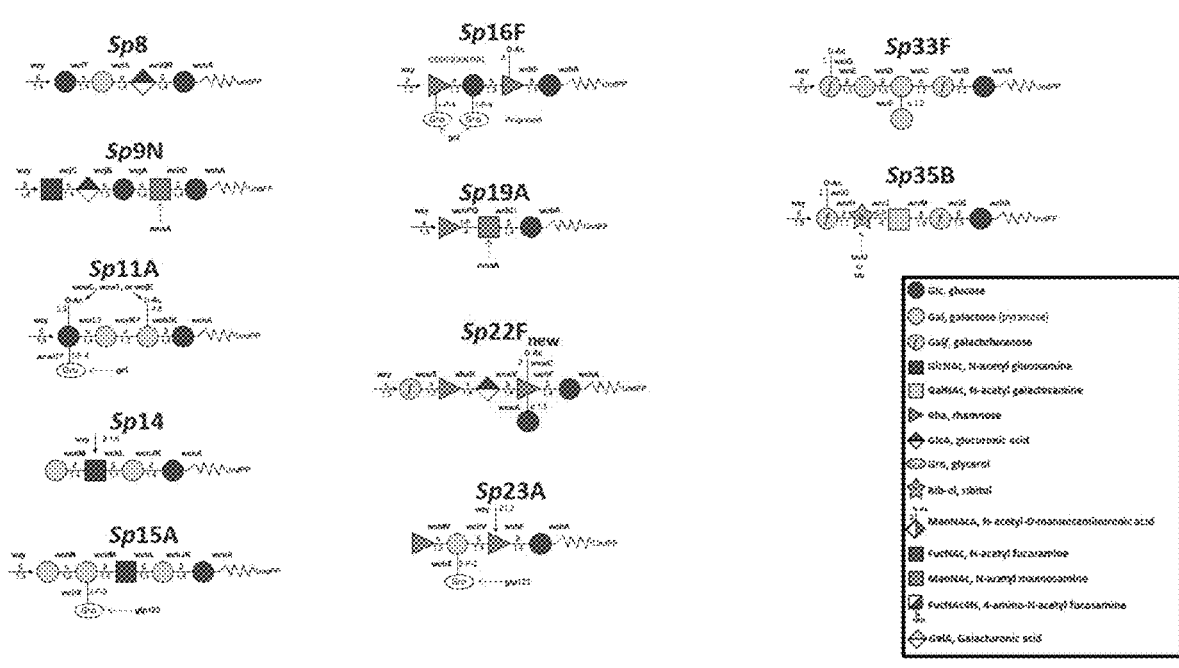
FIG. 5—Structure of *S. pneumoniae* capsular polysaccharide repeat units. Darks circles indicate glucose residues, light circles indicate galactose residues, light circles with "f" inside indicate galactofuranose, dark squares indicate N-acetyl glucosamine, light squares indicate N-acetyl galactosamine, triangles indicate rhamnose, horizontally split diamonds with dark top indicate glucuronic acid, ovals indicate glycerol, stars indicate ribitol, dark squares indicate N-acetyl fucosamine, medium squares indicate N-acetyl mannosamine, diagonally split squares indicate 4-amino-N-acetyl fucosamine and horizontally split diamonds indicate galacturonic acid.
Figure 6:
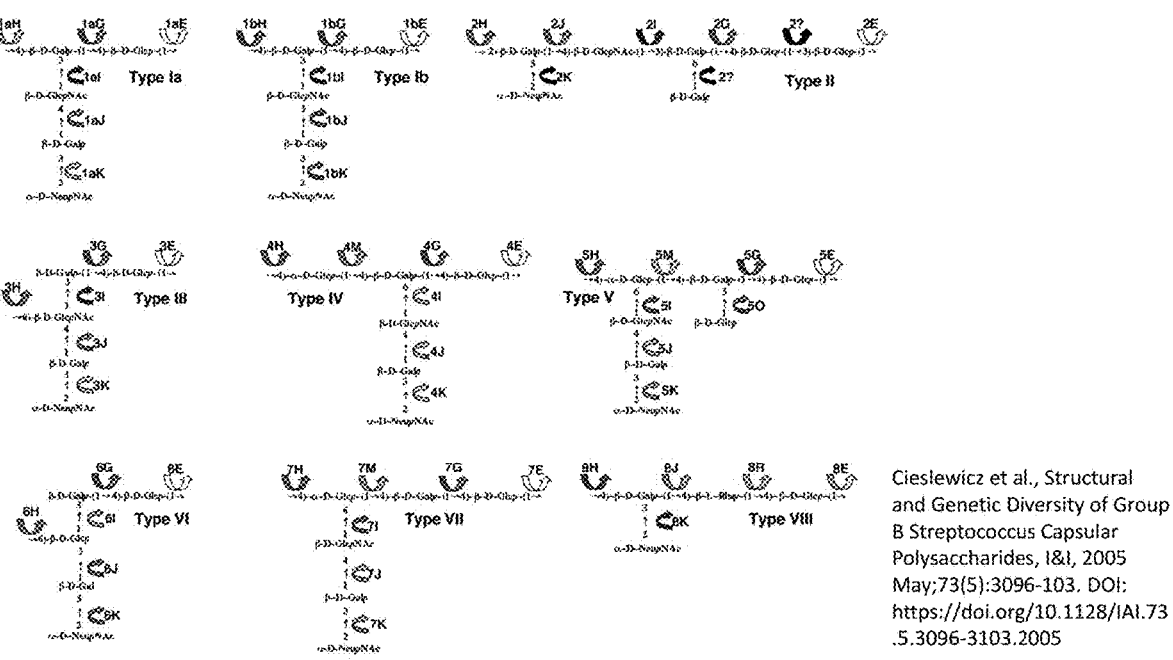
FIG. 6—Structure of Group B streptococcus capsular saccharide repeat units.

In some embodiments, the yield of protein glycosylation of the engineered PglB and the unmutated form of the engineered PglB can be compared by comparing the engineered PglB's and the original PglB's glycosylation yield of a protein with a polysaccharide or oligosaccharide lacking an N-acetyl sugar at the reducing end. For example a sugar with a glucose at the reducing end, for example a *Streptococcus pneumoniae* capsular polysaccharide or a Group B streptococcus capsular saccharide, for example those depicted in FIGS. 5 and 6. In an embodiment, the polysaccharide or oligosaccharide lacking an N-acetyl sugar at the reducing end is the capsular saccharide of *S. pneumoniae* serotype 8.

In some embodiments, the engineered PglB's glycosylation yield of a protein with a polysaccharide or oligosaccharide lacking an N-acetyl sugar at the reducing end is compared to an unmutated PglB's yield of a glycosylated protein with a polysaccharide or oligosaccharide having an N-acetyl sugar at the reducing end. For example a sugar with a glucose at the reducing end, for example a *Streptococcus pneumoniae* capsular polysaccharide or a Group B streptococcus capsular saccharide, for example those depicted in FIGS. 5 and 6. In an embodiment, the polysaccharide or oligosaccharide lacking an N-acetyl sugar at the reducing end is the capsular saccharide of *S. pneumoniae* serotype 8.

In some embodiments, the engineered PglB's glycosylation yield of a protein glycosylated with a *S. pneumoniae* serotype 8 capsular saccharide is increased by at least 1.1-fold, 1.2-fold, 1.3-fold, 1.5-fold, 1.7-fold, 2-fold, 2.5-fold, 3-fold, 5-fold, 10-fold, 100-fold, 500-fold or 1,000-fold relative to an unmutated PglB.

In some embodiments, the engineered PglB can increase the in vivo or in vitro yield of glycosylation of a protein with a *S. pneumoniae* serotype 8 capsular saccharide by between about 1.2-fold and about 5,000-fold, by between about 1.5-fold and about 2,000-fold, by between about 2-fold and about 1,000-fold, by between about 2-fold and about 20-fold or by between about 20-fold and about 2,000-fold compared to the yield achieved with an unmutated form of the engineered PglB.

In some embodiments, the engineered PglB can yield an in vivo glycosylation level or an in vitro glycosylation level of the protein of between about 1% to about 70%, of between about 3% to about 65%, of between about 5% to about 60%, of between about 5% to about 55%, of between about 10% to about 50%, of between about 15% to about 45%, of between about 20% to about 40%, or of between about 25% to about 35%. In some embodiments, the engineered PglB can yield an in vivo glycosylation level or an in vitro glycosylation level of the carrier protein of at least 1%, at least 3%, at least 5%, at least 10%, at least 15%, at least 20%, at least 25%, at least 30%, at least 35%, at least 40%, at least 45%, at least 50%, at least 55%, at least 60%, at least 65%, or at least 70%.

The engineered PglB can be from any organism having a PglB. In some embodiments, the engineered PglB is from a prokaryotic organism. In some embodiments, the engineered PglB is from *Campylobacter jejuni* (*C. jejuni*), *Campylobacter coli* (*C. coli*), *Campylobacter lari* (*C. lari*), *Campylobacter upsaliensis* (*C. upsaliensis*), *Campylobacter curvus* (*C. curvus*), *Campylobacter concisus* (*C. concisus*), *Campylobacter hominis* (*C. hominis*), *Campylobacter gracilis* (*C. gracilis*), *Campylobacter showae* (*C. showae*), *Sulfurimonas autotrophica* (*S. autotrophica*), *Sulfurimonas denitrificans* (*S. denitrificans*), *Sulfurospirillum deleyianum* (*S. deleyianum*), *Sulfuricurvum kujiense* (*S. kujiense*), *Nautilia profundicola* (*N. profundicola*), *Sulfuvorum* sp. NBC37-1, *Wolinella succinogenes* (*W. succinogenes*), *Caminibacter mediatlanticus* (*C. mediatlanticus*), *Nitratiruptor* sp. SB155-2, *Helicobacter pullorum* (*H. pullorum*), *Helicobacter Canadensis* (*H. Canadensis*), *Helicobacter winghamensis* (*Helicobacter winghamensis*), *Desulfurobacterium thermolithotr* (*D. thermolithotr*), *Desulfomicrobium baculatum* (*D. baculatum*), *Desulfovibrio vulgaris* (*D. vulgaris*), *Desulfovibrio alkaliphilus* (*D. Desulfohalobium retbaense* (*D. retbaense*), *Deferribacter desulfuricans* (*D. desulfuricans*), *Desulfovibrio salexigenes* (*D. salexigenes*), *Desulfovibrio piger* (*D. salexigenes*), *Desulfovibrio aespoeensis* (*D. aespoeensis*), *Cand. Puniceispirillum marinum*, *Calditerrivibrio nitroreducens* (*C. nitroreducens*) or *Methanothermus fervidus* (*M. fervidus*).

The point mutations identified herein are typically those found in the sequence of PglB from *C. jejuni* (for example PglB from *C. jejuni* of SEQ ID NO:1). A further aspect of the invention is a PglB from any of the species identified above containing the corresponding mutation to those disclosed for *C. jejuni* PglB of SEQ ID NO:1.

In some embodiments, the PglB OST polypeptide is an engineered PglB, an engineered PglB homologue or an engineered version of a naturally occurring PglB variant. PglB$_{Cj}$ homologues can comprise naturally occurring PglB$_{Cj}$ homologues, and non-naturally occurring PglB$_{Cj}$ homologues. PglB$_{Cj}$ homologues can comprise proteins having at least 70%, at least 75%, at least 80%, at least 85%, at least 90%, at least 95%, at least 96%, at least 97%, at least 98% or at least 99% sequence identity to a PglB$_{Cj}$ of SEQ ID NO:1. The degree of sequence identity may be determined using by the homology alignment algorithm of Needleman and Wunsch, the ClustalW program or the BLASTP algorithm. An algorithm using global alignment (Needleman and Wunsch) is preferred.

In some embodiments, the engineered PglB is an engineered PglB$_{Cl}$, an engineered PglB$_{Cl}$ homologue or an engineered version of a naturally occurring PglB$_{Cl}$ variant. PglB$_{Cl}$ homologues can comprise naturally occurring PglB$_{Cl}$ homologues, and non-naturally occurring PglB$_{Cl}$ homologues. PglB$_{Cl}$ homologues can comprise proteins having at least 70%, at least 75%, at least 80%, at least 85%, at least 90%, at least 95%, at least 96%, at least 97%, at least 98% or at least 99% sequence identity to a PglB$_{Cl}$ of SEQ ID NO:2. The degree of sequence identity may be determined by the homology alignment algorithm of Needleman and Wunsch, the ClustalW program or a BLASTP algorithm. An algorithm using global alignment (Needleman and Wunsch) is preferred.

In some embodiments, the engineered PglB comprises a PglB fragment, e.g., a PglB$_{Cj}$ fragment. In some embodiments, the PglB fragment comprises at least 100, at least 150, at least 200, at least 250, at least 300, at least 350, at least 400, at least 450, at least 500, at least 550, at least 600, or at least 650 contiguous amino acids of a full-length PglB for example of SEQ ID NO:1.

PglB$_{Cj}$ Modifications

In some embodiments, the engineered PglB OSTs described herein are modified wild-type N-OSTs, e.g., wild-type PglB$_{Cj}$. In some embodiments, the wild-type PglB$_{Cj}$ is a wild-type PglB$_{Cj}$ of SEQ ID NO:9, or of a naturally occurring variant thereof:

```
MLKKEYLKNP YLVLFAMIIL AYVFSVFCRF YWVWWASEFN

EYFFNNQLMI ISNDGYAFAE GARDMIAGFH QPNDLSYYGS

SLSALTYWLY KITPFSFESI ILYMSTFLSS LVVIPTILLA

NEYKRPLMGF VAALLASIAN SYYNRTMSGY YDTDMLVIVL

PMFILFFMVR MILKKDFFSL IALPLFIGIY LWWYPSSYTL

NVALIGLFLI YTLIFHRKEK IFYIAVILSS LTLSNIAWFY

QSAIIVILFA LFALEQKRLN FMIIGILGSA TLIFLILSGG

VDPILYQLKF YIFRSDESAN LTQGFMYFNV NQTIQEVENV

DLSEFMRRIS GSEIVFLFSL FGFVWLLRKH KSMIMALPIL

VLGFLALKGG LRFTIYSVPV MALGFGFLLS EFKAIMVKKY

SQLTSNVCIV FATILTLAPV FIHIYNYKAP TVFSQNEASL

LNQLKNIANR EDYVVTWWDY GYPVRYYSDV KTLVDGGKHL

GKDNFFPSFA LSKDEQAAAN MARLSVEYTE KSFYAPQNDI

LKTDILQAMM KDYNQSNVDL FLASLSKPDF KIDTPKTRDI

YLYMPARMSL IFSTVASFSF INLDTGVLDK PFTFSTAYPL

DVKNGEIYLS LGVVLSDDFR SFKIGDNVVS YNSIVEINSI

KQGEYKITPI DDKAQFYIFY LKDSAIPYAQ FILMDKTMFN

SAVYQMFFLG NYDKNLFDLV INSRDAKVFK LKIYPYDVPD

YA
```

In some embodiments, one or more of amino acids X57, X63, X94, X101, X172, X176, X191, X193, X233, X234, X255, X286, X295, X301, X319, X397, X402, X425, X435, X446, X462, X479, X523, X532, X601, X605, X606, X610, X645, X676 and X695 of SEQ ID NO:1, or any combination thereof, are modified. In an embodiment, one or more of X57, X301, X319, X462, X479 and X523, or any combination thereof are modified, for example by substitution. In an embodiment one or more of X57, X462 and X479 are modified. In an embodiment X57 is modified. In an embodiment, X462 and X479 are modified. In an embodiment X57, X462 and X479 are substituted. In an embodiment the A57R substitution is made. In an embodiment A57R, Y462W and H479M substitutions are made.

(a) PglB$_{Cl}$ Modifications

In some embodiments, the modified PglB OSTs described herein are modified wild-type PglB OSTs, e.g., wild-type PglB$_{Cl}$ (PglB of *Campylobacter lari*). In some embodiments, the wild-type PglB$_{Cj}$ is a wild-type PglB$_{Cl}$ of SEQ ID NO:10, or of a naturally occurring variant thereof:

```
MKLQQNETDN NSIKYTCILI LIAFAFSVLC RLYWVAWASE

FYEFFFNDQL NITTMDGYAF AEGARDMIAG FHQPNDLSYF
```

-continued
```
GSSLSTLTYW LYSILPFSFE SIILYMSAFF ASLIVVPIIL

IAREYKLTTY GFIAALLGSI ANSYYNRTMS GYYDTDMLVL

VLPMLILLTF IRLTINKDIF TLLLSPVFIM IYLWWYPSSY

SLNFAMIGLF GLYTLVFHRK EKIFYLTIAL MIIALSMLAW

QYKLALIVLL FAIFAFKEEK INFYMIWALI FISILILHLS

GGLDPVLYQL KFYVFKASDV QNLKDAAFMY FNVNETIMEV

NTIDPEVFMQ RISSSVLVFI LSFIGFILLC KDHKSMLLAL

PMLALGFMAL RAGLRFTIYA VPVMALGFGY FLYAFFNFLE

KKQIKLSLRN KNILLILIAF FSISPALMHI YYYKSSTVFT

SYEASILNDL KNKAQREDYV VAWWDYGYPI RYYSDVKTLI

DGGHLKGKDN FFSSFVLSKE QIPAANMARL SVEYTEKSFK

ENYPDVLKAM VKDYNKTSAK DFLESLNDKD FKFDTNKTRD

VYIYMPYRML RIMPVVAQFA NTNPDNGEQE KSLFFSQANA

IAQDKTTGSV MLDNGVEIIN DFRALKVEGA SIPLKAFVDI

ESITNGKFYY NEIDSKAQIY LLFLREYKSF VILDESLYNS

SYIQMFLLNQ YDQDLFEQIT NDTRAKIYRL KD
```

In another embodiment, provided herein is an engineered PglB$_{Cl}$ comprising an N314V substitution and a Y79R substitution. In a further embodiment, there is provided an engineered PglB$_{Cl}$ comprising a A59R mutation. In a further embodiment, there is provided an engineered PglB$_{Cl}$ comprising a Y468W and a H485M mutation. In a further embodiment, there is provided an engineered PglB$_{Cl}$ comprising a A59R, a Y468W and a H485M substitution. In a further embodiment, there is provided an engineered PglB$_{Cl}$ comprising a N314V, a Y79R, a A59R, a Y468W and a H485M substitution.

*Campylobacter coli* PglBs

A further aspect of the invention is native PglBs particularly from *Campylobacter coli* which have been found to have greater activity for the transfer of certain saccharides to a carrier protein containing the Asp/Glu-Z$_1$-Asn-Z$_2$-Ser/Thr (wherein Z$_1$ and Z$_2$ may be any natural amino acid except Pro) glycosylation consensus sequence. In the case of PglB from *C. coli* strain EFM37568 (SEQ ID NO:12) is has been found that the OST activity is higher than that of native *C. jejuni* PglB (SEQ ID NO:1) for the transfer of at least *S. flexneri* 2a, 3a and 6, plus *E. coli* O18.

PglB from *C. coli* strain CDG57218 (SEQ ID NO:13) was tested for its activity in transferring *E. coli* O18 saccharide to a protein containing a glycosylation consensus sequence. This OST activity was the same between PglB of *C. jejuni* and PglB of SEQ ID NO:13.

Figure 7:
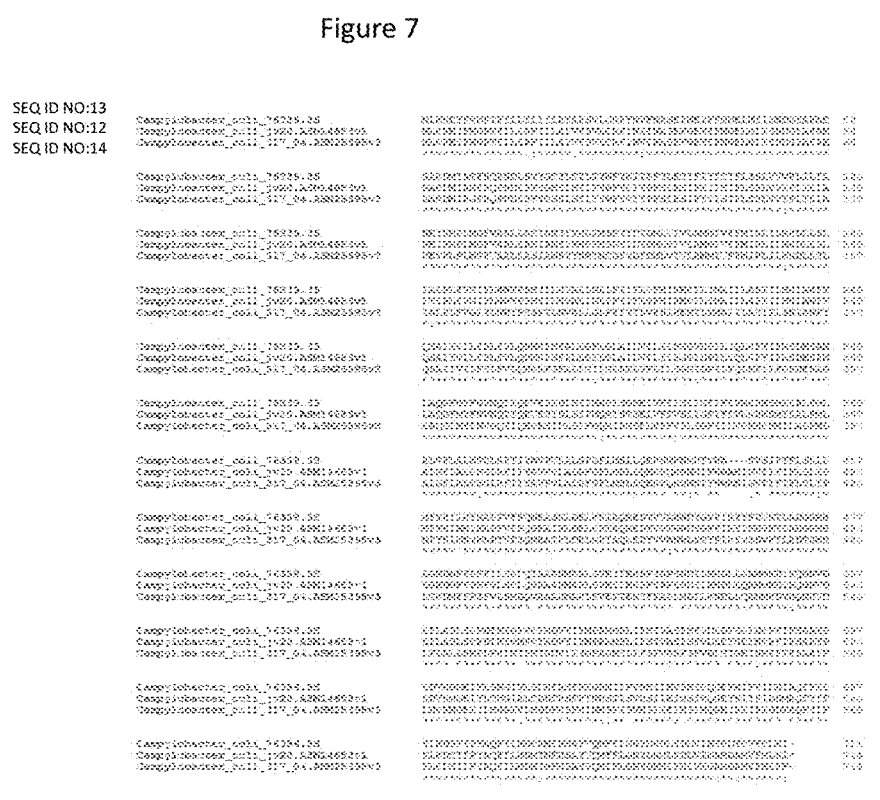

PglB from *C. coli* strain EIA90085 (SEQ ID NO:14) was tested for its activity in transferring *E. coli* O18 saccharide to a protein containing a glycosylation consensus sequence. This OST activity was the slightly greater than that of PglB of *C. jejuni*. We conclude that wild type PglBs from several strains of *C. coli* are equivalent or superior to PglB from *C. jejuni* for catalyzing the transfer of saccharide to a protein containing the glycosylation consensus sequence for PglB. The sequences of three stains of *C. coli* PglB are shown in FIG. 7 and the strain EFM37568 PglB sequence is slightly divergent from the amino acid sequence of the further two PglBs tested. The *C. coli* EFM37568 PglB gave particularly good results.

A further embodiment of the invention provides a use of a PglB oligosaccharyltransferase (OST) or functional fragment thereof of from *Campylobacter coli* (PglB$_{C.coli}$) in the production of a glycosylated protein in which a saccharide is attached to an N residue of a glycosylation consensus sequence, comprising the amino acid sequence Asp/Glu-Z$_1$-Asn-Z$_2$-Ser/Thr wherein Z$_1$ and Z$_2$ may be any natural amino acid except Pro. In an embodiment, the use is of a *C. coli* PglB having an amino acid sequence that is at least 80%, 85%, 90%, 95%, 97%, 99% or 100% identical to SEQ ID NO:12, 13 or 14. Optionally, the *C. coli* PglB has an amino acid sequence that is at least 80%, 85%, 90%, 95%, 97%, 99% or 100% identical to SEQ ID NO:12.

A further embodiment of the invention discloses the introduction of the amino acid substitutions described herein into a *C. coli* PglB. In an embodiment, the *C. coli* PglB contains at least one residue selected from the group consisting of amino acid X57, X63, X94, X101, X172, X176, X191, X193, X233, X234, X255, X286, X295, X301, X319, X397, X402, X426, X436, X447, X463, X480, X524, X533, X602, X606, X607, X611, X646, X677 and X696 is substituted to a different amino acid to that found at that position in SEQ ID NO:12. In an embodiment, there is provided a PglB$_{C.coli}$ oligosaccharyltransferase polypeptide or functional fragment containing a substitution at any one of the residues corresponding to amino acids X57, X463 and X480 of SEQ ID NO:12; optionally the substitution are at least one of A57R, Y463W and H480M. In an embodiment the PglB *C. coli* contains at least one amino acid substitutions at residue(s) X57, X77, X311, X462 and/or X480. In an embodiment, the amino acid substitutions are at 1, 2, 3, 4 or 5 of these positions. In an embodiment the substitutions are at least one amino acid substitutions at residue(s) A57R, Y77R, N311V, Y463W and/or H480M. In an embodiment, one, two, three, four or five of these mutations are introduced into the amino acid sequence of *C. coli* PglB, optionally having the sequence of SEQ ID NO:12.

Oligosaccharides and Polysaccharides

The oligosaccharides that can be linked to a protein by the engineered PglB OSTs provided herein can have from about 2 to about 100 monosaccharide units, e.g., 2, 4, 6, 8, 10, 15, 20, 25, 30, 40, 50, 60, 70, 80, 90 or 100 or from 4 to 90, 6 to 80, 8 to 70, 10 to 60, 15 to 50, 20 to 40 or 25 to 40 monosaccharide units. The polysaccharides that can be linked to a protein by the engineered PglB OSTs provided herein can have more than 100 monosaccharide units, e.g., at least 101, 110, 150, 200, 300, 400, 500, 600, 700, 800, 900, 1,000 monosaccharide units or more. For example, from 100 to 500, from 100 to 300 or from 100 to 200 monosaccharide units.

The proteins or PglB OSTs can comprise any PglB OST or any protein disclosed herein.

In some embodiments, the sugar at the reducing end of the oligosaccharide or polysaccharide is a pentose, hexose, or heptose. In some embodiments, the sugar at the reducing end of the oligosaccharide or polysaccharide is an aldopentose or a ketopentose. In some embodiments, the pentose is a D-arabinose, a D-lyxose, a D-ribose, a D-xylose, a D-ribulose, or a D-Xylulose. In some embodiments, the sugar at the reducing end of the oligosaccharide or polysaccharide is an aldohexose or a ketohexose. In some embodiments, the hexose is, e.g., a D-allose, D-altrose, D-glucose, D-mannose, D-gulose, D-idose, D-galactose, D-talose, D-psicose, D-fructose, D-sorbose or D-tagatose. In some embodiments, the sugar at the reducing end of the oligosaccharide or polysaccharide is a deoxy or a di-deoxy sugar, such as, e.g., a rhamnose, a fucose, or an abequose. In some embodiments, the sugar at the reducing end of the oligosaccharide or polysaccharide is an aldoheptose or a ketoheptose. In some embodiments, the heptose is a mannoheptulose. In a preferred embodiment, the sugar at the reducing end of the oligosaccharide of polysaccharide is glucose.

The oligosaccharides and polysaccharides that can be linked to a N residue of a protein by the engineered PglB OSTs provided herein can be those normally found in any organism, e.g., a prokaryotic organism or a eukaryotic organism. In some embodiments, the oligosaccharide or polysaccharide is from a pathogenic organism, e.g., a human pathogen or an animal pathogen (e.g., a farm animal or a pet). In some embodiments, the oligosaccharide or polysaccharide is from a bacterial organism. In some embodiments, the oligosaccharide or polysaccharide can be from *E. coli*, *Shigella sonnei*, *Shigella flexneri*, *Shigella dysenteriae*, *Salmonella* sp (e.g., *S. enterica* subsp. Enterica, *S. enterica* subsp. Salamae, *S. enterica* subsp. arizonae, *S. enterica* subsp. Diarizonae, *S. enterica* subsp. Houtenae, *S. bongori*, and *S. enterica* subsp. Indica, *Pseudomonas* sp (*P. aeruginosa*), *Klebsiella* sp. (e.g., *K. pneumonia*), *Acinetobacter*, *Chlamydia trachomatis*, *Vibrio cholera*, *Listeria* sp., e.g., *L. monocytogenes*, *Legionella pneumophila*, *Bordetella parapertussis*, *Burkholderia mallei* and *pseudomallei*, *Francisella tularensis*, *Campylobacter* sp. (*C. jejuni*); *Clostridium difficile*, *Staphylococcus aureus*, *Streptococcus pneumoniae*, *Streptococcus pyogenes*, *E. coli*, *Streptococcus agalacticae*, *Neisseria meningitidis*, *Candida albicans*, *Haemophilus influenza*, *Enterococcus faecalis*, *Borrelia burgdorferi*, *Neisseria gonorrhoea*, *Haemophilus influenza*, *Leishmania major*.

In some embodiments, the oligosaccharide or polysaccharide comprises an antigen, e.g., an epitope that is immunogenic in a human or an animal (e.g., a farm animal or a pet). In some embodiments, the oligosaccharide or the polysaccharide comprises an O antigen of *E. coli* (e.g., O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, O187), *Shigella flexneri* O1A, O1B, O2A, O3A, O6, *Shigella sonnei* O antigen, *Shigella dysenteriae* O1, *Salmonella* sp (*S. enterica* subsp. Enterica, *S. enterica* subsp. Salamae, *S. enterica* subsp. arizonae, *S. enterica* subsp. diarizonae, *S. enterica* subsp. houtenae, *S. bongori*, or *S. enterica* subsp. indica antigens and O types 1-67, as detailed in [44], *Pseudomonas* sp. (*P. aeruginosa* O serotypes 1-20 [45]), *Klebsiella* sp. (e.g., *K. pneumonia* serotypes O1, O2 (and subserotypes), O3, O4, O5, O6, O7, O8, O9, O10, O11, O12, [46]), Acinetobacter O antigens (e.g., *A. baumannii* O antigens identified in [47]), *Chlamydia trachomatis* O antigens (serotypes A, B, C, D, E, F, G, H, I J, K, L1, L2, L3), *Vibrio cholera* O antigens O1 to 155, *Listeria* sp., in particular *L.*

*monocytogenes* type 1, 2, 3, 4 and subserotypes thereof, *Legionella pneumophila* serotypes 1 to 15 O antigens, *Bordetella parapertussis* O antigens, *Burkholderia mallei* and *pseudomallei* O antigens, *Francisella tularensis, Campylobacter* sp. (*C. jejuni*); Capsular polysaccharides of *Clostridium difficile* (serotypes A, G, H, K, S1, S4, D, Cd-5, K Toma et al. 1988, and *C. perfringens* serotypes A, B, C, D or E), *Staphylococcus aureus* capsular saccharides from serotype 5 or serotype 8, *Streptococcus pneumoniae* capsular saccharides from serotype 1, 2, 3, 4, 5, 6A, 6B, 6C, 7F, 8, 9A, 9L, 9N, 9V, 10A, 11A, 12F, 14, 15A, 15B, 16F, 18C, 19A, 19F, 22F, 23F, 33F, 35B, *Streptococcus pyogenes* (group B streptococcus capsular serotype polysaccharides from serotype Ia, Ib, II, III, IV, V, VI, VII, or VIII), *Streptococcus agalactiae* (group A streptococcal capsular polysaccharides), *Neisseria meningitidis* (serogroups A, B, C, W, Y, X), *Candida albicans, Haemophilus influenza, Enterococcus faecalis* capsular polysaccharides type I-V; and other surface polysaccharide structures, e.g., the *Borrelia burgdorferi* glycolipids, *Neisseria meningitidis* pilin O glycan and lipooligosaccharide (LOS), *Haemophilus influenza* LOS, *Leishmania major* lipophosphoglycan, tumor associated carbohydrate antigens (malaria glycosyl phosphatidylinositol, *Mycobacterium tuberculosis* arabinomannan.

In some embodiments, the oligosaccharide or polysaccharide is a *Staphylococcus aureus* (*S. aureus*) or a *Salmonella enterica* sv. (*S. enterica* sv.) polysaccharide. In some embodiments, the polysaccharide is a *S. aureus* CP5 or CP8 or a *S. enterica* sv. *Typhimurium* LT2 polysaccharide.

In some embodiments, the oligosaccharide or polysaccharide comprises an N-acetyl sugar at the reducing end. In some embodiments, the oligosaccharide or polysaccharide comprising the N-acetyl sugar at the reducing end can comprise, e.g., an O antigen of *E. coli* (e.g., O1, O2, O3, O4, O5, O6, O7, O8, O9, O10, O11, O12, O13, O14, O15, O16, O17, O18, O19, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, O187), a capsular polysaccharide of *Staphylococcus aureus* (*S. aureus*) (e.g., CP5 or CP8), a capsular polysaccharide of *Francisella tularensis* Schu4, a capsular polysaccharide of *S. pneumoniae* capsules (e.g., CP1, 4, 5, 12, 25, 38, 44, 45 or 46), a *Neisseria meningitidis* pilin O glycan, a *Burkholderia mallei* and *pseudomallei* O antigen, a *Bordetella parapertussis* O antigen, a *Legionella pneumophila* serotypes 1 to 15 O antigen, a *Listeria* sp. O antigen, in particular an O antigen of *L. monocytogenes* type 1, 2, 3, 4, an O antigen of *Pseudomonas* sp. (*P. aeruginosa* O serotypes 1-20), an O antigen of *Klebsiella* sp. (e.g., *K. pneumonia* serotypes O1, O2 (and subserotypes), O3, O4, O5, O6, O7, O8, O9, O10, O11, O12), an O antigen of *Shigella* sp. (e.g., *S. dysenteriae, S.*

*sonnei, S. flexneri, S. boydii*), an Acinetobacter O antigen (e.g., *A. baumannii O antigens, or an O antigen of Listeria* sp.

N-acetyl sugars can comprise an amino-acetyl (N-acetyl) substituent at one or more carbon atoms of the sugar. For example, an N-acetyl sugar can comprise an N-acetyl substituent at the C2-atom of a monosaccharide unit, such as a glucose unit (N-acetylglucosamine).

In some embodiments, the oligosaccharide or polysaccharide comprises a sugar at the reducing end that is not N-acetylated. In some embodiments, the oligosaccharide or polysaccharide comprising the non-N-acetylated sugar at the reducing end can comprise, e.g., *E. coli* 020, an antigen of *Salmonella* sp (e.g., *S. enterica* subsp. *Enterica, S. enterica* subsp. Salamae, *S. enterica* subsp. *arizonae, S. enterica* subsp. *diarizonae, S. enterica* subsp. *houtenae, S. bongori,* or *S. enterica* subsp. *Indica* or *S. typhi*), an O antigen of type 1-67, a capsular polysaccharide of group A Streptococcus (*S. pyrogenes*), group B Streptococcus, and of *S. pneumoniae* CPS serotypes (encoding wchA, wcjG, or wcjH in their capsular gene clusters, i.e. all serotypes except CP1, 4, 5, 12, 25, 38, 44, 45, 46), or a *Salmonella enterica* sv. (*S. enterica* sv.) O antigen.

In some embodiments, the oligosaccharide or polysaccharide comprises a *S. aureus* CP5 or CP8 or a *S. enterica* sv. *Typhimurium* LT2 polysaccharide, a *Vibrio cholera* O antigen (e.g., O1 to 155), or a *Listeria* sp. O antigen (e.g., *L. monocytogenes* type 1, 2, 3, 4).

In some embodiments, the oligosaccharide or polysaccharide comprises a D-N-acetylfucosamine (D-FucNAc) residue at its reducing end, such as, e.g., capsular polysaccharides of *S. aureus* serotypes 5, 8 or *P. aeruginosa O antigen serotypes* O2, O5, O11, O16.

In some embodiments, the oligosaccharide or polysaccharide comprises a 4-amino-d-N-acetylfucosamine (D-FucNAc4N) residue at its reducing end, such as, e.g., certain oligosaccharides or polysaccharides from *S. pneumoniae*, like serotype 1, *Shigella sonnei* O antigen, or *Plesiomonas shigelloides* O17.

In some embodiments, the oligosaccharide or polysaccharide comprises a D-N-acetylquinosamine (D-QuiNAc) residue at its reducing end, such as, e.g., like *P. aeruginosa O antigen serotypes* 06, 01, or *Francisella tularensis* serotype Schu4.

In some embodiments, the oligosaccharide or polysaccharide comprises a galactose residue at its reducing end, such as, e.g., *S. enterica* LT2.

In some embodiments, the oligosaccharide or polysaccharide comprises a *S. pneumoniae* capsular polysaccharide serotype 5, *E. coli* O1, O2, *Cronobacter sakazakii* O5, i.e., poly- and oligosaccharide with a reducing end D-GlcNAc linked to 1-4 to a L-Rhamnose in beta configuration.

Proteins

The protein to be glycosylated by an engineered PglB OST of the invention is a protein containing at least one N residue situated in a glycosylation consensus sequence D/E-$Z_1$-N-$Z_2$-S/T ($Z_1$ and $Z_2 \neq$P). In some embodiments, the protein is a carrier protein. The activity of engineered PglB OST is capable of covalently bonding a saccharide immunogen to the carrier protein. The carrier protein provides T-cell epitopes which allow the attached saccharide immunogen to generate a T-dependent immune response. In some embodiments, the protein is a biopharmaceutical protein, to which the engineered PglB OST of the invention adds at least one saccharide to achieve correct glycosylation or correct folding or increased stability of the biopharmaceutical protein. In an embodiment, the biopharmaceutical protein is a monoclonal antibody, a fragment of a monoclonal antibody capable of binding to an antigen. In an embodiment, the biopharmaceutical protein is a erythropoietin, growth hormone, human insulin, Factor VIII, Factor IX, tissue plasminogen activator, glucagon, gonadotrophin, colony stimulating factor, interferon α, p or y, an interleukin e.g. interleukin 2, or tumour necrosis factor.

Carrier proteins can be linked to oligosaccharides or polysaccharides by the engineered PglB OSTs provided herein.

The carrier protein can be any natural carrier protein (from the same organism as the PglB OST) or any heterologous carrier protein (from a different organism than the PglB OST). In some embodiments, the carrier protein is an immunogen. Carrier proteins can be full-length proteins or fragments thereof. Exemplary carrier proteins comprise, without limitation, exotoxin A of *P. aeruginosa* (EPA), CRM197, diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, and *C. jejuni* natural glycoproteins. In some embodiments, the carrier protein is exotoxin A of *P. aeruginosa* (EPA).

In some embodiments, the carrier proteins N-glycosylated by an engineered PglB OST described herein are modified, e.g., modified in such a way that the protein is less toxic and or more susceptible to glycosylation, etc. In some embodiments, the carrier proteins are modified such that the number of glycosylation sites in the carrier proteins is maximized in a manner that allows for lower concentrations of the protein to be administered, e.g., in an immunogenic composition, in its bioconjugate form. Accordingly in certain embodiments, the carrier proteins described herein are modified to comprise 1, 2, 3, 4, 5, 6, 7, 8, 9, 10, or more glycosylation sites than would normally be associated with the carrier protein (e.g., relative to the number of glycosylation sites associated with the carrier protein in its native/natural, e.g., "wild-type" state). In some embodiments, introduction of glycosylation sites is accomplished by insertion of glycosylation consensus sequences (e.g., (i) the consensus sequence Asn-Z-Ser (Thr), wherein Z are independently selected from any amino acid except Pro; or (ii) the consensus sequence D/E-$Z_1$-N-$Z_2$-S/T, wherein $Z_1$ and $Z_2$ are independently selected from any amino acid except Pro) anywhere in the primary structure of the protein. Introduction of such glycosylation sites can be accomplished by, e.g., adding new amino acids to the primary structure of the protein (the glycosylation sites are added, in full or in part), or by modifying existing amino acids in the protein in order to generate the glycosylation sites (amino acids are not added to the protein, but selected amino acids of the protein are mutated so as to form glycosylation sites). Those of skill in the art will recognize that the amino acid sequence of a protein can be readily modified using approaches known in the art, e.g., engineered approaches that comprise modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In certain embodiments, the classical 5 amino acid glycosylation consensus sequence may be extended by lysine residues for more efficient glycosylation, and thus the inserted consensus sequence may encode 5, 6, or 7 amino acids that should be inserted or that replace acceptor protein amino acids.

The PglB OSTs can comprise any N-OST disclosed herein.

In some embodiments, the carrier proteins comprise a "tag," a sequence of amino acids that allows for the isolation and/or identification of the carrier protein. For example, adding a tag to a carrier protein described herein can be useful in the purification of that protein and, hence, the purification of conjugate vaccines comprising the tagged carrier protein. Exemplary tags that can be used herein comprise, without limitation, histidine (HIS) tags (e.g., hexa histidine-tag, or 6×His-Tag), FLAG-TAG, and HA tags. In certain embodiments, the tags used herein are removable, e.g., removal by chemical agents or by enzymatic means, once they are no longer needed, e.g., after the protein has been purified.

Nucleic Acids

In another aspect, provided herein are polynucleotides encoding a mutated PglB oligosaccharyltransferase from any *Campylobacter* species including *C. jejuni*, *C. lari* and *C. coli*, as provided herein.

In some embodiments, the nucleic acids encode a engineered $PglB_{Cj}$ wherein one or more of amino acids 57, 63, 94, 101, 176, 191, 193, 233, 234, 286, 301, 319, 397, 402, 435, 446, 462, 479, 523, 532, 605, 610, 645, 676, or 695 is/are modified.

In an embodiment, there is provided a polynucleotide encoding a PglB oligosaccharyltransferase in which the amino acid corresponding to 311 of SEQ ID NO:1 is substituted, for example by a valine residue (N311V). In an embodiment, the 311 substitution is supplemented with a substitution of the amino acid corresponding to 77 in SEQ ID NO:1, for example by a arginine residue (Y77R). In an embodiment the polynucleotide encoding PglB OST has a substation at the amino acid corresponding to 57 in SEQ ID NO:1, for example by an arginine residue (A57R). The 57 substitution is either in combination with 311 and 77 substitutions or is independently substituted. In an embodiment, the polynucleotide encodes a PglB OST with N311V, Y77R and A57R substitutions.

In an embodiment, there is provided a polynucleotide encoding a PglB OST containing substitutions at residue 462 or 479 or 462 and 479 of SEQ ID NO:1, for example, Y462W or H479M or Y462W and H479M. These mutations are optionally combined with mutations corresponding to residues 311, 77 and/or 57 of SEQ ID NO:1, for example N311V, Y77R and A57R. In an embodiment there are provided nucleic acids encoding PglB OST with mutations at 57, 462 and 479, for example A57R, Y462W and H479M. In an embodiment, there is provided a polynucleotide encoding a PglB OST with substitutions at residues corresponding to 77, 57, 462 and 479 of SEQ ID NO:1, for example Y77R, A57R, Y462W and H479M.

In some embodiments, the polynucleotide of the invention encodes a PglB OST which comprises modifications (for example amino acids substitutions, or nucleotide substitutions in the polynucleotide encoding PglB) in, e.g., two or more, three or more, four or more, five or more, six or more, seven or more, eight or more, nine or more, or ten or more amino acids, for example 2-30, 3-25, 4-20, 5-20, 6-20, 7-20 or 10-20 amino acid substitution. In an embodiment, substitutions are at positions encoding the following residues of SEQ ID NO:1:

57; 77; 57 and 77; 311 and 77; 57, 77 and 311; 57 and 462; 57, 462 and 479; 57, 462, 479, 77 and 311; 57, 462, 479, 300, 301, 308 and 570; 57, 462, 479, 300, 301, 308, 570 and 77; 57, 462, 479, 300, 301, 308, 570, 77 and 311.

In an embodiment, the following substitutions are present at positions encoding the following residues of SEQ ID NO:1 (where/denotes or):

A57R/T; Y77R; A57R/T and Y77R; A57R and Y77R; N311V and Y77R; A57R/T, Y77R and N311V; A57R, Y77R and N311V; A57R/T and Y462P/C/W/T/N; A57R/T and Y462W/T/N; A57R and Y462W; A57R/T, Y462P/C/W/T/N and H479M; A57R/T, Y462W/T/N and H479M; A57R, Y462W and H479M; A57R/T, Y462P/C/W/T/N, H479M, Y77R and N311V; A57R/T, Y462W/T/N, H479M, Y77R and N311V; A57R, Y462W, H479M, Y77R and N311V; A57R/T, Y462P/C/W/T/N, H479M, L301P/G/F and L570R/V; A57R, Y462W, H479M, L301P and L570R; A57R/T, Y462P/C/W/T/N, H479M, N300L, L301P/G/F, F308W/F and L570R/V; A57R, Y462W, H479M, N300L, L301P, F308W and L570R; A57R/T, Y462P/C/W/T/N, H479M, L301P/G/F, L570R/V and Y77R; A57R, Y462W, H479M, L301P, L570R and Y77R; A57R/T, Y462P/C/W/T/N, H479M, N300L, L301P/G/F, F308W/F, L570R/V and Y77R; A57R, Y462W, H479M, N300L, L301P, F308W, L570R and Y77R; A57R/T, Y462P/C/W/T/N, H479M, L301P/G/F, L570R/V, Y77R and N311V; A57R, Y462W, H479M, L301P, L570R, Y77R and N311V; A57R/T, Y462P/C/W/T/N, H479M, N300L, L301P/G/F, F308W/F, L570R/V, Y77R and N311V; A57R, Y462W, H479M, N300L, L301P, F308W, L570R, Y77R and N311V.

Host Cells

In another aspect, provided herein is a host cell comprising a mutated PglB OST or a wild-type or mutated *C. coli* PglB OST provided herein. In an embodiment, the host cell is a heterologous host cell (e.g. not *Campylobacter*). In an embodiment, the host cell is *E. coli*. In some embodiments, the host cell comprises two or more engineered PglB OSTs provided herein (e.g., 2, 3, 4, 5, 6, 7, 8, 9, 10 or more engineered PglB OSTs).

In another aspect, provided herein is a host cell comprising a nucleic acid provided herein (e.g., encoding an engineered PglB OST provided herein). In some embodiments, the host cell comprises two or more nucleic acids provided herein (e.g., 2, 3, 4, 5, 6, 7, 8, 9, 10 or more nucleic acids).

In some embodiments, the host cell comprises one or more further enzymes useful for bioconjugate production or protein N-glycosylation (e.g., a glycosyltransferase). In some embodiments, at least one of the further enzymes useful for bioconjugate production is a recombinant enzyme. In some embodiments, the host cell comprises two or more further enzymes useful for bioconjugate production (e.g., 2, 3, 4, 5, 6, 7, 8, 9, 10 or more further enzymes).

In some embodiments, the host cell is a prokaryotic cell. In some embodiments, the host cell is an *E. coli* cell. In some embodiments, the host cell comprises an engineered PglB OST provided herein. In some embodiments, the host cell comprises a protein containing at least one glycosylation consensus sequence and an engineered N-OST provided herein. In some embodiments, the host cell comprises a protein containing at least one glycosylation consensus sequence, an engineered PglB OST provided herein, and a recombinant glycosyltransferase. In some embodiments, the engineered PglB OST is an engineered *C. jejuni* PglB.

In certain embodiments, the host cells used to produce the bioconjugates described herein are engineered to comprise heterologous nucleic acids, e.g., heterologous nucleic acids that encode one or more proteins containing at least one glycosylation consensus sequence and/or heterologous nucleic acids that encode one or more proteins, e.g., genes encoding one or more enzymes. In some embodiments, heterologous nucleic acids that encode proteins involved in glycosylation pathways (e.g., prokaryotic and/or eukaryotic glycosylation pathways) are introduced into the host cells described herein. Such nucleic acids can encode proteins including, without limitation, oligosaccharyl transferases and/or glycosyltransferases. Heterologous nucleic acids (e.g., nucleic acids that encode proteins containing at least one glycosylation consensus sequence and/or nucleic acids that encode other proteins, e.g., proteins involved in glycosylation) can be introduced into the host cells described herein using any methods known to those of skill in the art, e.g., electroporation, chemical transformation by heat shock, natural transformation, phage transduction, and conjugation. In some embodiments, heterologous nucleic acids are introduced into the host cells described herein using a plasmid, e.g., the heterologous nucleic acids are expressed in the host cells by a plasmid (e.g., an expression vector). In some embodiments, heterologous nucleic acids are introduced into the host cells described herein using the method of insertion described in International Patent application Publication No. WO 2014/057109.

In certain embodiments, additional modifications can be introduced (e.g., using recombinant techniques) into the host cells described herein. For example, host cell nucleic acids (e.g., genes) that encode proteins that form part of a possibly competing or interfering glycosylation pathway (e.g., compete or interfere with one or more heterologous genes involved in glycosylation that are recombinantly introduced into the host cell) can be deleted or modified in the host cell background (genome) in a manner that makes them inactive/dysfunctional (i.e., the host cell nucleic acids that are deleted/modified do not encode a functional protein or do not encode a protein whatsoever). In certain embodiments, when nucleic acids are deleted from the genome of the host cells provided herein, they are replaced by a desirable sequence, e.g., a sequence that is useful for glycoprotein production.

Exemplary genes that can be deleted in host cells (and, in some cases, replaced with other desired nucleic acid sequences) include genes of host cells involved in glycolipid biosynthesis, such as waaL (see, e.g., Feldman et al., 2005, PNAS USA 102:3016-3021), the lipid A core biosynthesis cluster (waa), galactose cluster (gal), arabinose cluster (ara), colonic acid cluster (wca), capsular polysaccharide cluster, metabolic enzymes involved in nucleotide activated sugar biosynthesis, enterobacterial common antigen cluster (wec), and prophage O antigen modification clusters like the gtrABS cluster.

The host cells described herein can produce the N-glycosylated carrier proteins described herein. In some embodiments, the N-glycosylated carrier proteins produced by the host cells described herein are antigens, e.g., viral or bacterial antigens that can be used in vaccines. In some embodiments, the N-glycosylated carrier proteins produced by the host cells described herein can be any protein containing a glycosylation consensus sequence described herein, wherein said proteins are modified by the host cells described herein so as to possess one or more beneficial characteristics, e.g., the protein is N-glycosylated.

Certain of the Examples below describe application of methods described herein in Gram-negative *E. coli* host cells; however, any host cells known to those of skill in the art could be used as to produce N-glycosylated carrier proteins, including archea, prokaryotic host cells other than *E. coli*, and eukaryotic host cells.

Exemplary prokaryotic host cells that can be used in accordance with the methods described herein comprise, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species.

In certain embodiments, the host cells described herein comprise a genome into which one or more DNA sequences has been introduced, wherein the DNA sequences encode a protein or comprise an operon/gene cluster involved in the N-glycosylation of proteins. For example, in some embodiments, a host cell described herein comprises a genome into which one or more of the following has been inserted: DNA encoding an engineered PglB OST, DNA encoding a gly-cosyltransferase, DNA encoding a protein containing at least one glycosylation sequence, DNA comprising an rib gene cluster, DNA comprising a capsular polysaccharide gene cluster, and/or DNA encoding an epimerase.

The host cells can include engineered PglB OSTs or *C. coli* PglB OSTs provided herein or nucleic acids encoding the engineered PglB OSTs or *C. coli* PglB OSTs provided herein, whereby the engineered PglB OSTs can be from any organism having N-OSTs, including a prokaryotic organism. In some embodiments, the PglB OST protein or PglB OST encoding nucleic acid is from the genus *Campylobacter* (e.g., the pglB gene from *C. jejuni*).

The host cells described herein can comprise a glycosyl-transferase known in the art or a nucleic acid sequence encoding a glycosyltransferases known in the art. In some embodiments, the glycosyltransferase is a glycosyltransfer-ase described in International Patent Application Publication No. WO 2011/138361, the disclosure of which is incorpo-rated by reference herein in its entirety. In some embodi-ments, the glycosyltransferase is from a Gram-positive bac-terium, e.g., the glycosyltransferase is from *S. pneumoniae*, for example from *S. pneumoniae* serotype 1, 2, 3, 4, 5, 6A, 6B, 6C, 7F, 8, 9A, 9L, 9N, 9V, 10A, 11A, 12F, 14, 15A, 15B, 16F, 18C, 19A, 19F, 22F, 23F, 33F, 35B (preferably from serotype 8), or from *Streptococcus pyogenes* (group B streptococcus capsular serotype polysaccharides from sero-type Ia, Ib, II, III, IV, V, VI, VII, or VIII). In some embodiments, the glycosyltransferase is capsular polysac-charide 5 from *S. aureus*. In some embodiments, the glyco-syltransferase is capsular polysaccharide 8 from *S. aureus*. In some embodiments, the glycosyltransferase is from a Gram-negative bacterium, e.g., *E. coli* or *Shigella flexneri* or *Shigella sonnei*.

The host cells described herein can comprise or produce a protein containing at least one glycosylation consensus site or comprise a nucleic acid sequence encoding a protein containing at least one glycosylation consensus sequence known in the art. The proteins produced by the host cells described herein comprise at least one N-glycosylation consensus sequence, e.g., either the consensus sequence (i) Asn-Z-Ser(Thr), wherein Z is are independently selected from any amino acid except Pro; or (ii) D/E-$Z_1$-N-$Z_2$-S/T, wherein $Z_1$ and $Z_2$ are independently selected from any amino acid except Pro. Accordingly, the host cell can comprise DNA sequences encoding an N-glycosylation con-sensus sequence. The host cell can include any protein known in the art, including these described herein. In some embodiments, the protein is a carrier protein such as an Exotoxin A of *P. aeruginosa* (EPA), including EPA that has been modified to comprise at least one N-glycosylation consensus sequence. In some embodiments, the protein is the carrier protein is cholera toxin B. In some embodiments, the carrier protein is AcrA. In some embodiments, the carrier protein is H1A. In some embodiments, the carrier protein is ClfA. In some embodiments, the carrier protein is CRM197.

Bioconjugates

The bioconjugates described herein are conjugates between a protein (e.g., any carrier protein described herein) and an oligosaccharide or a polysaccharide (e.g., any oligo-saccharide or polysaccharide described herein) prepared in a host cell, wherein host cell machinery links the oligosac-charide or polysaccharide to the protein (e.g., N-links). In some embodiments, the oligosaccharide or polysaccharide is an antigen (e.g., any antigen described herein). Glycocon-jugates can include bioconjugates, as well as sugar antigen (e.g., oligo- and polysaccharides)-protein conjugates pre-pared by other means, e.g., by chemical linkage of the protein and sugar antigen.

The engineered PglB OSTs or *C. coli* PglB OSTs described herein can be introduced into a cell (e.g. a Gram negative bacterial cell) to produce host cells that produce bioconjugates comprising an N-glycosylated carrier protein. In some embodiments, provided herein are bioconjugates including a carrier protein N-glycosylated with an antigen (e.g., an oligosaccharide or a polysaccharide) described herein. In some embodiments, the carrier protein is EPA. The bioconjugates described herein can, for example and without limitation, comprise any carrier protein described herein. The bioconjugates described herein can, for example and without limitation, comprise any oligosaccharide or polysaccharide described herein.

In an embodiment, the heterologous glycosylated carrier protein is *Streptococcus pneumoniae* serotype 12F-EPA, *Streptococcus pneumoniae* serotype 8-EPA, *S. pneumoniae* serotype 19A-EPA, *S. pneumoniae* serotype 22F-EPA, *S. pneumoniae* serotype 23A-EPA, or *S. pneumoniae* serotype 35B-EPA. In an embodiment, the heterologous glycosylated carrier protein is a *S. pneumoniae* capsular saccharide or Group B streptococcus capsular saccharide attached to a carrier protein, for example EPA, CRM197, DT or TT.

In an embodiment, the heterologous glycosylated carrier protein is *S. aureus* capsular polysaccharide type 5 conju-gated to EPA, CRM197, DT, TT or a staphylococcal protein such as ClfA or Hla, or a *S. aureus* capsular polysaccharide type 8 conjugated to EPA, CRM197, DT, TT or a staphy-lococcal protein such as ClfA or Hla or *S. sonnei*-EPA.

In some embodiments, provided herein is a bioconjugate including EPA and one or more different oligosaccharides or polysaccharides described herein.

In some embodiments, provided herein is a bioconjugate including carrier protein conjugated to one or more of *E. coli* O1, O2, O4, O6, O7, O8, O11, O15, O16, O17, O18, O20, O22, O25, O73, O75, and/or O83. In some embodiments, the carrier protein is EPA.

In some embodiments, provided herein is a bioconjugate including a carrier protein conjugated to one or more dif-ferent *P. aeruginosa* polysaccharides. In some embodiments, the carrier protein is EPA.

In some embodiments, provided herein is a bioconjugate comprising a carrier protein conjugated to one or more different *K. pneumonia* polysaccharides. In a specific embodiment, the carrier protein is EPA.

Methods for Producing a Bioconjugate

In some embodiments, the engineered PglB OSTs and *C. coli* PglBs provided herein can be used to produce a bio-conjugate provided herein, such as a glycoconjugate. In some embodiments, the engineered PglB OSTs and *C. coli* PglBs provided herein can be used to produce conjugate vaccines, i.e. vaccines that contain an oligosaccharide or polysaccharide and a protein antigen of the pathogen that the vaccine is designed against.

In another aspect, provided herein is a method of producing a bioconjugate including culturing a host cell provided herein, in a cell culture medium. In some embodiments, the host cell comprises a nucleic acid encoding an engineered PglB OST or *C. coli* PglB provided herein. In some embodiments, the host cell comprises a nucleic acid encoding a carrier protein described herein. In some embodiments, the carrier protein has one or more N-glycosylation consensus sequence. In some embodiments, the host cell comprises a nucleic acid encoding a glycosyltransferase.

In some embodiments, the bioconjugate is an N-glycosylated carrier protein. The N-glycosylated carrier protein can comprise an oligosaccharide or polysaccharide component including any oligosaccharide or polysaccharide described herein. The N-glycosylated carrier protein can comprise any carrier protein described herein. In some embodiments, the bioconjugate is a natural *C. jejuni* N-glycosylated polypeptide (including a *C. jejuni* oligosaccharide or polysaccharide component and a *C. jejuni* carrier protein). In some embodiments, the bioconjugate is a heterologous *C. jejuni* glycosylated polypeptide (including a polysaccharide component and/or a carrier protein that is not from *C. jejuni*). In some embodiments, the glycosylated polypeptide does not have an N-acetyl sugar at its reducing end. In some embodiments, the glycosylated polypeptide has a glucose or galactose at its reducing end.

In some embodiments, the methods further comprise purifying the bioconjugate from the host cell culture. Methods for purifying bioconjugates, such as N-glycosylated carrier proteins, from host cell cultures are known in the art. See, e.g., Jan-Christer Janson, *Protein Purification: Principles, High Resolution Methods, and Applications*. Wiley; 3 edition (Mar. 22, 2011).

Analytical Methods

Various methods can be used to analyze the structural compositions and sugar chain lengths of the bioconjugates or N-glycosylated carrier proteins described herein.

In one embodiment, hydrazinolysis can be used to analyze glycans. First, polysaccharides are released from their protein carriers by incubation with hydrazine according to the manufacturer's instructions (Ludger Liberate Hydrazinolysis Glycan Release Kit, Oxfordshire, UK). The nucleophile hydrazine attacks the glycosidic bond between the polysaccharide and the carrier protein and allows release of the attached glycans. N-acetyl groups are lost during this treatment and have to be reconstituted by re-N-acetylation. The free glycans are purified on carbon columns and subsequently labeled at the reducing end with the fluorophor 2-amino benzamide (Bigge J C, Patel T P, Bruce J A, Goulding P N, Charles S M, Parekh R B. Nonselective and efficient fluorescent labeling of glycans using 2-amino benzamide and anthranilic acid. *Anal Biochem.* 1995 Sep. 20; 230(2):229-38). The labeled polysaccharides are separated on a GlycoSep-N column (GL Sciences) according to the HPLC protocol of Royle et al. (Royle L, Mattu T S, Hart E, Langridge J I, Merry A H, Murphy N, Harvey D J, Dwek R A, Rudd P M. An analytical and structural database provides a strategy for sequencing 0-glycans from microgram quantities of glycoproteins. *Anal Biochem.* 2002 May 1; 304(1): 70-90). The resulting fluorescence chromatogram indicates the polysaccharide length and number of repeating units. Structural information can be gathered by collecting individual peaks and subsequently performing MS/MS analysis. Thereby the monosaccharide composition and sequence of the repeating unit could be confirmed and additionally in homogeneity of the polysaccharide composition could be identified. Specific peaks of low molecular weight can be analyzed by MALDI-MS/MS and the result is used to confirm the glycan sequence. Each peak corresponds to a polymer consisting of a certain number of repeat units and fragments thereof. The chromatogram thus allows to measure the polymer length distribution. The elution time is an indication for polymer length, fluorescence intensity correlates with molar abundance for the respective polymer.

In another embodiment, SDS-PAGE or capillary gel electrophoresis can be used to assess glycans and glycoconjugates. Polymer length for the O antigen glycans which are synthesized here is defined by the number of repeat units that are linearly assembled. This means that the typical ladder like pattern is a consequence of different repeat unit numbers that compose the glycan. Thus, two bands next to each other in SDS PAGE or other techniques that separate by size differ by only a single repeat unit. These discrete differences are exploited when analyzing glycoproteins for glycan size: The unglycosylated carrier protein and the glycoconjugate with different polymer chain lengths separate according to their electrophoretic mobilities. The first detectable repeating unit number ($n_1$) and the average repeating unit number ($n_{average}$) present on a glycoconjugate are measured. These parameters can be used to demonstrate batch to batch consistency or polysaccharide stability.

In another embodiment, high mass MS and size exclusion HPLC could be applied to measure the size of the complete glycoconjugates.

In another embodiment, an anthrone-sulfuric acid assay can be used to measure polysaccharide yields (Leyva A, Quintana A, Sanchez M, Rodriguez E N, Cremata J, Sanchez J C. Rapid and sensitive anthrone-sulfuric acid assay in microplate format to quantify carbohydrate in biopharmaceutical products: method development and validation. *Biologicals.* 2008 March; 36(2):134-41. Epub 2007 Nov. 26).

Change in Glycosylation Site Usage

To show that the site usage in a specific protein is changed glycosylation site usage can be quantified. Methods to do so are listed below.

Glycopeptide LC-MS/MS: glycoconjugates are digested with protease(s), and the peptides are separated by a suitable chromatographic method (C18, Hydrophilic interaction HPLC HILIC, GlycoSepN columns, SE HPLC, AE HPLC), and the different peptides are identified using MS/MS. This method can be used with or without previous sugar chain shortening by chemical (smith degradation) or enzymatic methods. Quantification of glycopeptide peaks using UV detection at 215 to 280 nm allow relative determination of glycosylation site usage.

Size exclusion HPLC: Higher glycosylation site usage is reflected by an earlier elution time from a SE HPLC column. See also (a).

Homogeneity

Glycoconjugate homogeneity (the homogeneity of the attached sugar residues) can be assessed using methods that measure glycan length and hydrodynamic radius.

Benefits

The engineered PglB OSTs and *C. coli* PglBs provided herein and methods provided herein of using the engineered PglB OST or *C. coli* PglB provided herein are of particular commercial importance and relevance, as they allow for rapid, high-yield, large-scale and low-cost fermentation of highly homogeneous preparations of glycosylated proteins (including for example glycoconjugate preparation or conjugate vaccine preparations). The engineered PglB OSTs and

*C. coli* PglBs provided herein enable an economically viable production of commercially and therapeutically valuable glycosylated proteins, such as conjugate vaccines. In addition, the engineered PglB OSTs and *C. coli* PglBs of the invention provide more efficient N-glycosylation of proteins, particularly in cases where the glycan is not naturally transferred by wild type PglB. For example where the oligosaccharide to be transferred to the N residue of the protein does not have a GlcNAc residue at the reducing terminus, for example where the reducing terminus of the oligosaccharide is a glucose residue. The reproducibility and robustness of biotechnological bioconjugate production methods using the engineered PglB OSTs provided herein, is expected to contribute to a reduction of production costs. The homogeneity of especially biotherapeutic conjugate vaccines is generally believed to affect the clinical safety of drug products.

Abbreviations and Definitions

For the purposes of the descriptions herein, the abbreviations used for the genetically encoded amino acids are conventional and are as follows in Table 1:

TABLE 1

| AMINO ACID | THREE-LETTER | ONE-LETTER |
|---|---|---|
| ALANINE | ALA | A |
| ARGININE | ARG | R |
| ASPARAGINE | ASN | N |
| ASPARTATE | ASP | D |
| CYSTEINE | CYS | C |
| GLUTAMATE | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

When the three-letter abbreviations are used, unless specifically preceded by an "L" or a "D" or clear from the context in which the abbreviation is used, the amino acid may be in either the L- or D-configuration about α-carbon (Cα). For example, whereas "Ala" designates alanine without specifying the configuration about the α carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When peptide sequences are presented as a string of one-letter or three-letter abbreviations (or mixtures thereof), the sequences are presented in the N→C direction in accordance with convention.

The technical and scientific terms used in the descriptions herein will have the meanings commonly understood by one of ordinary skill in the art, unless specifically defined otherwise. Accordingly, the following terms are intended to have the following meanings. All U.S patents and published U.S. patent applications, including all sequences disclosed within such patents and patent applications, referred to herein are expressly incorporated by reference.

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically, encoded acidic amino acids include L-Glu (E) and L-Asp (D).

"Amino acid" or "residue" as used in context of the polypeptides disclosed herein refers to the specific monomer at a sequence position (e.g., P5 indicates that the "amino acid" or "residue" at position 5 of SEQ ID NO: 2 is a proline.)

"Amino acid difference" or "residue difference" refers to a change in the residue at a specified position of a polypeptide sequence when compared to a reference sequence. The polypeptide sequence position at which a particular amino acid or amino acid change ("residue difference") is present is sometimes described herein as "Xn", or "position n", where n refers to the residue position with respect to the reference sequence.

For example, a residue difference at position X8, where the reference sequence has a serine, refers to a change of the residue at position X8 to any residue other than serine. As disclosed herein, an enzyme can include one or more residue differences relative to a reference sequence, where multiple residue differences typically are indicated by a list of the specified positions where changes are made relative to the reference sequence (e.g., "one or more residue differences as compared to SEQ ID NO: 1 at the following residue positions: X27, X30, X35, X37, X57, X75, X103, X185, X207, X208, X271, X286, or X296.").

A specific substitution mutation, which is a replacement of the specific residue in a reference sequence with a different specified residue may be denoted by the conventional notation "X(number)X', where X is the single letter identifier of the residue in the reference sequence, "number" is the residue position in the reference sequence, and X' is the single letter identifier of the residue substitution in the engineered sequence.

"Aliphatic amino acid or residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Aromatic amino acid or residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Basic amino acid or residue" refers to a hydrophilic amino acid or residue having a side chain exhibiting a pKa value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Codon-optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the PglB oligosaccharyltransferase enzymes may be codon-optimized for optimal production from the host organism selected for expression.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Conservative" amino acid substitutions or mutations refer to the interchangeability of residues having similar side chains, and thus typically involves substitution of the amino acid in the polypeptide with amino acids within the same or similar defined class of amino acids. However, as used herein, in some embodiments, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. Table 2 below shows exemplary conservative substitutions.

TABLE 2

| Residue | Possible Conservative Mutations |
|---|---|
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| P | none |
| N, Q, S, T | Other polar |
| H, Y, W, F | Other aromatic (H, Y, W, F) |
| C | None |

"Constrained amino acid or residue" refers to an amino acid or residue that has a constrained geometry. Herein, constrained residues include L-Pro (P) and L-His (H). Histidine has a constrained geometry because it has a relatively small imidazole ring. Proline has a constrained geometry, because it also has a five-membered ring.

"Control sequence" is defined herein to include all components, which are necessary or advantageous for the expression of a polynucleotide and/or polypeptide of the present disclosure. Each control sequence may be native or foreign to the polynucleotide of interest. Such control sequences include, but are not limited to, a leader, polyadenylation sequence, propeptide sequence, promoter, signal peptide sequence, and transcription terminator.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence of the non-reference sequence. For example, a given amino acid sequence, such as that of an engineered PglB oligosaccharyltransferase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Cysteine" or L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, up to 20% of the total number of amino acids, or up to 30% of the total number of amino acids making up the polypeptide while retaining enzymatic activity and/or retaining the improved properties of an engineered PglB oligosaccharyltransferase enzyme. Deletions can be directed to the internal portions and/or terminal portions of the polypeptide. In various embodiments, the deletion can comprise a continuous segment or can be discontinuous.

"Derived from" as used herein in the context of engineered enzymes identifies the originating enzyme, and/or the gene encoding such enzyme, upon which the engineering was based. For example, the engineered oligosaccharyltransferase enzyme of SEQ ID NO: 4 was obtained by mutating the PglB oligosaccharyltransferase of SEQ ID NO:

2. Thus, this engineered PglB oligosaccharyltransferase enzyme of SEQ ID NO: 4 is "derived from" the polypeptide of SEQ ID NO: 2

An "engineered PglB oligosaccharyltransferase", as used herein, refers to a PglB oligosaccharyltransferase-type protein which has been systematically modified, through the insertion of new amino acids into its reference sequence, the deletion of amino acids present in its reference sequence, or the mutation of amino acids in its reference sequence into alternate amino acids, either through a process of random mutagenesis followed by selection of mutants having a particular property or through the intentional introduction of particular amino acid changes into the protein sequence.

"Fragment", as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99%, or more, of the full-length PglB oligosaccharyltransferase polypeptide, for example, the polypeptide of SEQ ID NO: 4.

A "functional fragment" or a "biologically active fragment", used interchangeably, herein refers to a polypeptide that has an amino-terminal and/or carboxy-terminal deletion(s) and/or internal deletions, but where the remaining amino acid sequence is identical to the corresponding positions in the sequence to which it is being compared and that retains substantially all of the activity of the full-length polypeptide. A functional fragment contains at least 100, 200, 300, 400 or 500 contiguous amino acids "Heterologous" polynucleotide refers to any polynucleotide that is introduced into a host cell by laboratory techniques, and includes polynucleotides that are removed from a host cell, subjected to laboratory manipulation, and then reintroduced into a host cell.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably, about 75% identity, about 85% identity to the target DNA, or with greater than about 90% identity to target-polynucleotide. Exemplary moderately stringent conditions are conditions equivalent to hybridization in 50% formamide, 5×Denhart's solution, 5×saline-sodium phosphate-EDTA (SSPE), 0.2% sodium dodecyl sulfate (SDS) at 42° C., followed by washing in 0.2×SSPE, 0.2% SDS, at 42° C. "High stringency hybridization" refers generally to conditions that are about 10° C. or less from the thermal melting temperature Tm as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C.

Other high stringency hybridization conditions, as well as moderately stringent conditions, are described in the references cited above.

"Hydrophilic amino acid or residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R)."Hydrophobic amino acid or residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically, encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Hydroxyl-containing amino acid or residue" refers to an amino acid containing a hydroxyl (—OH) moiety. Genetically-encoded hydroxyl-containing amino acids include L-Ser (S) L-Thr (T) and L-Tyr (Y).

"Improved enzyme property" refers to any enzyme property made better or more desirable for a particular purpose as compared to that property found in a reference enzyme. For the engineered PglB oligosaccharyltransferase polypeptides described herein, the comparison is generally made to a reference PglB oligosaccharyltransferase enzyme which does not contain the particular mutation which improves enzyme efficiency, although in some embodiments, the reference PglB oligosaccharyltransferase can be another improved engineered PglB oligosaccharyltransferase. Enzyme properties for which improvement can be made include, but are not limited to, enzymatic activity (which can be expressed in terms of yield of N-glycosylated protein), thermal stability, solvent stability, pH activity profile, coenzyme requirements, refractoriness to inhibitors (e.g., product inhibition), stereospecificity, and suppression of acid side-product production.

"Insertion" refers to modification of the polypeptide by addition of one or more amino acids to the reference polypeptide. In some embodiments, the improved engineered PglB oligosaccharyltransferase enzymes comprise insertions of one or more amino acids to the naturally occurring PglB oligosaccharyltransferase polypeptide as well as insertions of one or more amino acids to other improved PglB oligosaccharyltransferase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved PglB oligosaccharyltransferase enzymes may be present within a cell, present in the cellular medium, or prepared in various forms, such as lysates or isolated preparations. As such, in some embodiments, the improved PglB oligosaccharyltransferase enzyme can be an isolated polypeptide.

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects: (a) the structure of the peptide backbone in the area of the substitution (e.g., proline for glycine); (b) the charge or hydrophobicity; or (c) the bulk of the side chain.

"Non-polar amino acid" or "Non-polar residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see, e.g., Altschul, et al., 1990, *J. Mol. Biol.* 215: 403-410 and Altschul, et al., 1977, *Nucleic Acids Res.* 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul, et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Natl Acad Sci USA* 89:10915).

Numerous other algorithms are available that function similarly to BLAST in providing percent identity for two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel, et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison WI), using default parameters provided. The ClustalW program is also suitable for determining identity.

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Preferred, optimal, high codon usage bias codons" refers, interchangeably, to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; Codon W, John Peden, University of Nottingham; McInerney, J. O, 1998, *Bioinformatics* 14:372-73; Stenico, et al., 1994, *Nucleic Acids Res.* 222437-46; Wright, F., 1990, Gene 87:23-29). Codon usage tables are available for a growing list of organisms (see for, example, Wada, et al., 1992, *Nucleic Acids Res.* 20:2111-2118; Nakamura, et al., 2000, *Nucl. Acids Res.* 28:292; Duret, et al., supra; Henaut and Danchin, "*Escherichia coli* and *Salmonella,*" 1996, Neidhardt, et al., Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (EST), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E.

C., 1996, *Methods Enzymol.* 266:259-281; Tiwari, et al., 1997, *Comput. Appl. Biosci.* 13:263-270).

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Reference sequence" refers to a defined sequence to which another (e.g., altered) sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Because two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity.

The term, "reference sequence", is not intended to be limited to wild-type sequences, and can include engineered or altered sequences. For example, in some embodiments, a "reference sequence" can be a previously engineered or altered amino acid sequence. For instance, a "reference sequence based on SEQ ID NO: 2 having a glycine residue at position X12" refers to a reference sequence corresponding to SEQ ID NO: 2 with a glycine residue at X12 (the un-altered version of SEQ ID NO: 2 has an aspartate at X12).

"Small amino acid" or "small residue" refers to an amino acid or residue having a side chain that is composed of a total of three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Substantial identity" refers to a polynucleotide or polypeptide sequence that has at least 80, 81, 82, 83, 84, 85, 86, 87, 88, 89, 90, 91, 92, 93, 94, 95, 96, 97, 98, 99, or more percent sequence identity, as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure PglB oligosaccharyltransferase composition will comprise about 60% or more, about 70% or more, about 80% or more, about 90% or more, about 95% or more, about 96% or more, about 97% or more, about 98% or more or about 99% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species and elemental ion species are not considered to be macromolecular species. In some embodiments, the isolated improved PglB oligosaccharyltransferase polypeptide is a substantially pure polypeptide composition.

The invention is further disclosed in the following paragraphs:

1. A PglB oligosaccharyltransferase (OST) polypeptide comprising an amino acid sequence that is at least 80%, 85%, 90%, 95%, 96%, 97%, 98%, or 99% identical to the amino acid sequence set out in SEQ ID NO:1 or 2 or a functional fragment thereof, wherein the PglB oligosaccharyltransferase polypeptide amino acid sequence includes the feature that: at least one residue selected from the group consisting of amino acid X57, X63, X94, X101, X172, X176, X191, X193, X233, X234, X255, X286, X295, X301, X319, X397, X402, X425, X435, X446, X462, X479, X523, X532, X601, X605, X606, X610, X645, X676 and X695 is substituted to a different amino acid to that found at that position in SEQ ID NO:1.

2. The PglB oligosaccharyltransferase polypeptide or functional fragment thereof of paragraph 1, wherein the amino acid sequence comprises at least one feature selected from the list consisting of:

the residue corresponding to X57 is a hydrophilic residue;

the residue corresponding to X63 is chosen from a polar residue and a hydrophobic residue;

the residue corresponding to X94 is a polar residue;

the residue corresponding to X101 is chosen from an acidic residue, a non-polar residue, a hydrophilic residue, constrained residue, and an aromatic residue;

the residue corresponding to X172 is an acidic residue;

the residue corresponding to X176 is chosen from a non-polar residue and an acidic residue;

the residue corresponding to X191 is chosen from a hydrophilic residue and an aromatic residue;

the residue corresponding to X193 is chosen from a non-polar residue, hydrophilic residue, and aromatic residue;

the residue corresponding to X233 is an aliphatic residue:

the residue corresponding to X234 is chosen from a small residue, hydrophilic residue, and aromatic residue;

the residue corresponding to X255 is a hydrophilic residue;

the residue corresponding to X286 is chosen from a hydrophobic residue and a polar residue;

the residue corresponding to X295 is acidic or aliphatic;

the residue corresponding to X301 is chosen from a constrained residue, a non-polar residue and an aromatic residue;

the residue corresponding to X319 is chosen from a hydrophilic residue and an aliphatic residue;

the residue corresponding to X397 is chosen from a hydrophilic residue and a hydrophobic residue;

the residue corresponding to X402 is a hydrophilic residue;

the residue corresponding to X425 is a polar residue;

the residue corresponding to X435 is chosen from hydrophilic residue and a hydrophobic residue;

the residue corresponding to X446 is a non-polar residue;

the residue corresponding to X462 is chosen from an aromatic residue, a constrained residue and a small residue;

the residue corresponding to X479 is a hydrophobic residue;

the residue corresponding to X523 is a basic residue;

the residue corresponding to X532 is a hydrophilic residue;

the residue corresponding to X601 is a hydrophobic residue;

the residue corresponding to X605 is an acidic residue;

the residue corresponding to X606 is a constrained residue;

the residue corresponding to X610 is a chosen from a hydrophilic residue and a hydrophobic residue;

the residue corresponding to X645 is chosen from an aliphatic residue and a hydrophilic residue;

the residue corresponding to X676 is chosen from an aromatic residue, a hydrophilic residue, and a non-polar residue;

the residue corresponding to X695 is chosen from a polar residue and an aliphatic residue.

3. The PglB oligosaccharyltransferase polypeptide or functional fragment thereof of paragraph 1 or 2, wherein the amino acid sequence comprises at least one feature selected from the group consisting of: residue X57 is chosen from T and R; residue X63 is chosen from L and Q; residue X94 is N; residue X101 is chosen from W, E, H, P, R, M, and G; residue X172 is E; residue X176 is chosen from E and G; residue X191 is chosen from H, D, R, and Y; residue X193 is chosen from T, H, G, and F; X233 is V; residue X234 is chosen from H, C, and W; residue X255 is H; residue X286 is chosen from A, Q, and L; residue X295 is E or L; residue X301 is chosen from P, G, and F; residue X319 is chosen from A, Q, L, and T; residue X397 is chosen from N, L, and Q; residue X402 is chosen from R and H; residue X425 is S; residue X435 is chosen from A, L, F, H, and R; residue X446 is G; residue X462 is chosen from P, C, W, T, and N; residue X479 is M; residue X523 is R; residue X532 is H; residue X601 is G; residue X605 is D; residue X606 is P; residue X610 is chosen from P, L, R, D, and A; residue X645 is chosen from L, S, and H; residue X676 is chosen from Q, W, and G; and residue X695 is chosen from I and Q.

4. The PglB oligosaccharyltransferase polypeptide or functional fragment thereof of any one of paragraphs 1-3, wherein the amino acid sequence comprises at least one feature selected from the list consisting of: the residue corresponding to amino acid 57 of SEQ ID NO: 1 is mutated to R; the residue corresponding to amino acid 101 of SEQ ID NO:1 is mutated to M; the residue corresponding to amino acid 191 of SEQ ID NO:1 is mutated to H, D, R or Y (preferably to Y); the residue corresponding to amino acid 462 of SEQ ID NO:1 is mutated to P or W; the residue corresponding to amino acid 479 of SEQ ID NO:1 is mutated to M and the residue corresponding to amino acid 676 of SEQ ID NO:1 is mutated to W.

5. The PglB oligosaccharyltransferase polypeptide or functional fragment thereof of any one of paragraphs 1-4, wherein the residue corresponding to amino acid 57 of SEQ ID NO:1 is mutated to R or K or T, preferably to R or T, more preferably to R.

6. The PglB oligosaccharyltransferase polypeptide or functional fragment thereof of paragraph 5, wherein the residue corresponding to amino acid 57 of SEQ ID NO:1 is mutated to R.

7. The PglB oligosaccharyltransferase polypeptide of functional fragment thereof of any one of paragraphs 1-6 wherein the PglB oligosaccharyltransferase polypeptide amino acid sequence includes the feature that: at least one residue selected from the group consisting of amino acid X78, X84, A155, X293, X300, X301, X306, X308, X462, X464, X479, X523 and X570 is substituted to a different amino acid to that found at that position in SEQ ID NO:1.

8. The PglB OST polypeptide of functional fragment thereof of paragraph 7 wherein the amino acid sequence includes at least one feature chosen from the group consisting of:

the residue corresponding to X78 is a hydroxyl-containing residue;

the residue corresponding to X84 is an aromatic residue;

the residue corresponding to X155 is a polar residue;

the residue corresponding to X293 is a small residue;

the residue corresponding to X300 is an aliphatic residue;

the residue corresponding to X301 is chosen from a constrained residue and a non-polar residue;

the residue corresponding to X306 is a hydrophilic residue;

the residue corresponding to X308 is an aromatic residue;

the residue corresponding to X462 is chosen from an aromatic residue and a polar residue;

the residue corresponding to X464 is an aliphatic residue;

the residue corresponding to X479 is a hydrophobic residue;

the residue corresponding to X523 is a basic residue; and the residue corresponding to X570 is chosen from a basic residue and a aliphatic residue.

9. The PglB OST polypeptide of functional fragment thereof of any one of paragraphs 7-8 wherein the amino acid sequence includes at least one feature selected from the group consisting of: X78 is mutated to T; X84 is mutated to W; X155 is mutated to Q; X293 is mutated to C; X300 is mutated to L; X301 is mutated to P or G; X306 is mutated to H; X308 is mutated to W; X462 is mutated to W, N or T; X464 is mutated to L; X479 is mutated to M; X523 is mutated to R; X570 is mutated to R or V.

10. The PglB OST of any one of paragraphs 7-9 wherein the amino acid sequence includes at least one feature selected from the list consisting of: amino acid X300 is mutated to L; amino acid X301 is mutated to P, amino acid X308 is mutated to W, amino acid X462 is mutated to W, amino acid X479 is mutated to M and amino acid X570 is mutated to R.

11. The PglB OST of any one of paragraphs 7-10 wherein the amino acid sequence includes at least one feature selected from the list consisting of: the residue corresponding to amino acid X301 of SEQ ID NO:1 is mutated to P; the residue corresponding to amino acid X462 of SEQ ID NO:1 is mutated to N or W and the residue corresponding to amino acid X479 of SEQ ID NO:1 is mutated to M.

12. The PglB OST of any one of paragraphs 7-11 wherein the amino acid sequence contains a mutation at the residue corresponding to amino acid X479 of SEQ ID NO:1 to M.

13. The PglB of any one of paragraphs 7-12 wherein the amino acid sequence contains a mutation at the residue corresponding to amino acid X462 of SEQ ID NO:1.

14. The PglB of any one of paragraph 7-13 wherein the amino acid sequence contains a mutation at the residue corresponding to amino acid X462 of SEQ ID NO:1 to W and a mutation at the residue corresponding to amino acid X479 of SEQ ID NO:1 to M.

15. The PglB OST of any one of paragraphs 7-14 containing at least, 2, 3, 4, 5 or 6 of the features of the amino acid corresponding to X300 of SEQ ID NO:1 is mutated to L; the amino acid corresponding to X301 of SEQ ID NO:1 is mutated to P, the amino acid corresponding to X308 of SEQ ID NO:1 is mutated to W, the amino acid corresponding to X462 of SEQ ID NO:1 is mutated to W, the amino acid corresponding to X479 of SEQ ID NO:1 is mutated to M and the amino acid corresponding to X570 of SEQ ID NO:1 is mutated to R.

16. The PglB OST of paragraph 15 wherein amino acid X300 is mutated to L; amino acid X301 is mutated to P, amino acid X308 is mutated to W, amino acid X462 is mutated to W, amino acid X479 is mutated to M and amino acid X570 is mutated to R.

17. The PglB OST of any one of paragraphs 1-16 wherein the amino acid sequence comprises at least one residue difference as compared to the amino acid sequence set forth in SEQ ID NO: 1 in at least one residue position selected from the group consisting of: amino acids X12, X51, X104, X130, X176, X177, X186, X191, X218, X234, X286, X295, X306, X308, X319, X382, X482, and X523.

18. The PglB OST of paragraph 17 wherein the amino acid sequence includes at least one feature chosen from:
the residue corresponding to amino acid X12 is a hydroxyl-containing residue;
the residue corresponding to amino acid X51 is an aliphatic residue;
the residue corresponding to amino acid X104 is an aliphatic residue;
the residue corresponding to amino acid X130 is an aliphatic residue;
the residue corresponding to amino acid X176 is an acidic residue;
the residue corresponding to amino acid X177 is an aliphatic residue;
the residue corresponding to amino acid X186 is an aliphatic residue;
the residue corresponding to amino acid X191 is an aromatic residue;

the residue corresponding to amino acid X218 is a small residue;
the residue corresponding to amino acid X234 is chosen from an aromatic residue and a small residue;
the residue corresponding to amino acid X286 is chosen from a polar residue and an aliphatic residue;
the residue corresponding to amino acid X295 is an aliphatic residue;
the residue corresponding to amino acid X306 is a hydrophilic residue;
the residue corresponding to amino acid X308 is an aromatic residue;
the residue corresponding to amino acid X319 is chosen from an aliphatic residue and a polar residue;
the residue corresponding to amino acid X382 is a small residue;
the residue corresponding to amino acid X482 is a basic residue;
the residue corresponding to amino acid X523 is a basic residue.

19. The PglB OST or functional fragment thereof of paragraph 17 or 18 wherein the amino acid sequence includes at least one feature chosen from the group consisting of: residue X12 is S; residue X51 is L; residue X104 is L; residue X130 is L; residue X176 is E; residue X177 is V; residue X186 is L; residue X191 is Y; residue X218 is A; residue X234 is chosen from C and W; residue X286 is chosen from Q and L; residue X295 is L or E; residue X306 is H; residue X308 is F; residue X319 is chosen from L and Q; residue X382 is S; residue X482 is R; and residue X523 is R.

20. The PglB OST or functional fragment thereof of paragraph any one of paragraphs 17-19 wherein the amino acid sequence includes at least one feature selected from the group consisting of: the residue corresponding to amino acid X218 of SEQ ID NO:1 is A and the residue corresponding to amino acid X382 of SEQ ID NO:1 is S.

21. The PglB oligosaccharyltransferase polypeptide or functional fragment thereof of any one of paragraph 17-20, wherein the wherein the amino acid sequence includes the following features: amino acid X191 is Y; amino acid X286 is Q; amino acid X295 is L or E; amino acid X382 is S; amino acid X482 is R; amino acid X523 is R.

22. The PglB oligosaccharyltransferase polypeptide or functional fragment thereof of any one of paragraphs 1-21, wherein the amino acid sequence comprises a residue difference as compared to the amino acid sequence set forth in SEQ ID NO: 1 in at least one residue position selected from: amino acid X21, amino acid X27, amino acid X42, amino acid X44, amino acid X53, amino acid X80, amino acid X97, amino acid X297, amino acid X317, amino acid X341, amino acid X383, amino acid X388, amino acid X410, amino acid X421, amino acid X480, and amino acid X486.

23. The PglB oligosaccharyltransferase polypeptide or functional fragment thereof of Paragraph 22, wherein the amino acid sequence includes at least one feature chosen from the group consisting of:
the residue corresponding to amino acid X21 is chosen from a hydroxyl-containing residue and an aliphatic residue;
the residue corresponding to amino acid X27 is a chosen from a hydroxyl-containing residue and a hydrophobic residue;

the residue corresponding to amino acid X42 is chosen from an aromatic residue and a small residue;

the residue corresponding to amino acid X44 is chosen from a hydrophobic residue and a hydrophilic residue;

the residue corresponding to amino acid X52 is chosen from a hydrophilic residue and an aliphatic residue;

the residue corresponding to amino acid X80 is a small residue;

the residue corresponding to amino acid X97 is an aliphatic residue;

the residue corresponding to amino acid X297 is chosen from a basic residue and a hydroxyl-containing residue;

the residue corresponding to amino acid X317 is a small residue;

the residue corresponding to amino acid X341 is an aliphatic residue;

the residue corresponding to amino acid X421 is a non-polar residue;

the residue corresponding to amino acid X480 is chosen from a hydrophilic residue and a hydrophobic residue; and the residue corresponding to amino acid X486 is a small residue, a hydrophilic residue, and an aliphatic residue.

24. The PglB oligosaccharyltransferase polypeptide or functional fragment thereof of paragraph 22 or 23, wherein the amino acid sequence includes at least one feature chosen from the group consisting of: amino acid X21 is chosen from S and L; amino acid X27 is chosen from M, S, A and W; amino acid X42 is chosen from W and C; amino acid X44 is chosen from M and H; amino acid X53 is chosen from S, I and H; amino acid X80 is chosen from A and D; amino acid X97 is I; amino acid X297 is chosen from K, R S and Y; amino acid X317 is chosen from S and A; amino acid X341 is L; amino acid X383 is M; amino acid X388 is chosen from M and I; amino acid X410 is I; amino acid X421 is G; amino acid X480 is chosen from W, N, Q, I, T, and M; and amino acid X486 is chosen from C, N, L, H, and V.

25. The PglB oligosaccharyltransferase polypeptide or functional fragment thereof of any one of paragraphs 22-24, wherein the wherein the amino acid sequence includes the following features: X297 is R.

26. The PglB oligosaccharyltransferase polypeptide or functional fragment thereof of any one of paragraphs 1-25, wherein the amino acid sequence contains at least one further point mutation at a residue corresponding to amino acid X300, X301, X308, X462, X479 or X570 of SEQ ID NO:1.

27. The PglB oligosaccharyltransferase polypeptide or functional fragment thereof of paragraph 26, wherein the residue corresponding to amino acid X462 of SEQ ID NO:1 is mutated from Y to W.

28. The PglB oligosaccharyltransferase polypeptide or functional fragment thereof of paragraph 26-27, wherein the residue corresponding to amino acid X479 of SEQ ID NO:1 is mutated from H to M.

29. The PglB oligosaccharyltransferase polypeptide or functional fragment thereof of any one of paragraphs 26-28, wherein the residue corresponding to amino acid X300 of SEQ ID NO:1 is mutated from N to L.

30. The PglB oligosaccharyltransferase polypeptide or functional fragment thereof of any one of paragraphs 26-29, wherein residue corresponding to amino acid X301 of SEQ ID NO:1 is mutated from L to P.

31. The PglB oligosaccharyltransferase polypeptide or functional fragment thereof of any one of paragraphs 26-30 wherein residue corresponding to amino acid X308 of SEQ ID NO:1 is mutated from F to W.

32. The PglB oligosaccharyltransferase polypeptide or functional fragment thereof of any one of paragraphs 26-31 wherein residue corresponding to amino acid X570 of SEQ ID NO:1 is mutated from L to R.

33. The PglB oligosaccharyltransferase polypeptide or functional fragment thereof of any one of paragraphs 26-32, wherein the residue corresponding to amino acid X191 of SEQ ID NO:1 is mutated from L to Y.

34. The PglB oligosaccharyltransferase polypeptide or functional fragment thereof of any one of paragraphs 26-33, wherein the residue corresponding to amino acid X286 of SEQ ID NO:1 is mutated from Y to Q.

35. The PglB oligosaccharyltransferase polypeptide or functional fragment thereof of any one of paragraphs 26-34, wherein the residue corresponding to amino acid X295 of SEQ ID NO:1 is mutated from S to L or E.

36. The PglB oligosaccharyltransferase polypeptide or functional fragment thereof of any one of paragraphs 26-35, wherein the residue corresponding to amino acid X382 of SEQ ID NO:1 is mutated from A to S.

37. The PglB oligosaccharyltransferase polypeptide or functional fragment thereof of any one of paragraphs 26-36, wherein the residue corresponding to amino acid X482 of SEQ ID NO:1 is mutated from K to R.

38. The PglB oligosaccharyltransferase polypeptide or functional fragment thereof of any one of paragraphs 26-37, wherein the residue corresponding to amino acid X523 of SEQ ID NO:1 is mutated from T to R.

39. The PglB oligosaccharyltransferase or functional fragment thereof of any one of paragraphs 26-38, wherein the residue corresponding to amino acid X297 of SEQ ID NO:1 is mutated from E to R.

40. The PglB oligosaccharyltransferase or functional fragment thereof of any one of paragraphs 26-39, wherein the residue corresponding to amino acid X80 of SEQ ID NO:1 is mutated from S to D.

41. The PglB oligosaccharyltransferase polypeptide or functional fragment thereof of any one of paragraphs 26-40, wherein the residue corresponding to amino acid X187 of SEQ ID NO:1 is mutated from I to V.

42. The PglB oligosaccharyltransferase polypeptide or functional fragment thereof of any one of paragraphs 26-41, wherein the residue corresponding to amino acid X359 of SEQ ID NO:1 is mutated from I to Q.

43. The PglB oligosaccharyltransferase polypeptide or functional fragment thereof of any one of paragraphs 26-42, wherein the residue corresponding to amino acid X406 of SEQ ID NO:1 is mutated from N to I.

44. The PglB oligosaccharyltransferase polypeptide or functional fragment thereof of any one of paragraphs 1-43, wherein the residue corresponding to amino acid X77 of SEQ ID NO:1 is R and the residue corresponding to amino acid X311 of SEQ ID NO: 1 is V.

45. The PglB oligosaccharyltransferase polypeptide or functional fragment thereof of paragraph 1, having the amino acid sequence as set forth in any one of SEQ ID NOs: 2, 3, 4, 5, 6, 7 or 8.

46. The PglB oligosaccharyltransferase polypeptide or functional fragment thereof of any one of paragraphs 1-44, wherein the residues corresponding to amino acids X57, X462 and X479 of SEQ ID NO:1 are substituted with a different amino acid to that found at that position in SEQ ID NO:1; optionally to A57R, Y462W and H479M.

47. The PglB oligosaccharyltransferase polypeptide or functional fragment thereof of any one of paragraphs 1-46, wherein the residues corresponding to amino acids X57, X300, X301, X308, X462, X479 and X570 of SEQ ID NO:1 are substituted with a different amino acid to that found at that position in SEQ ID NO:1; optionally to A57R, N300L, L301P, F308W, Y462W, H479M, and L570R.

48. The PglB oligosaccharyltransferase polypeptide of any one of paragraphs 1-47 wherein the PglB oligosaccharyltransferase polypeptide is full length, optionally with a length of 712, 713 or 714 amino acids 49. The PglB oligosaccharyltransferase polypeptide of any one of paragraphs 1-48 wherein the PglB oligosaccharyltransferase is from *C. jejuni*.

50. The PglB oligosaccharyltransferase polypeptide of any one of paragraphs 1-48 wherein the PglB oligosaccharyltransferase is from *C. lari*.

51. The PglB oligosaccharyltransferase polypeptide of any one of paragraphs 1-48 wherein the PglB oligosaccharyltransferase is from *C. coli*.

52. The PglB oligosaccharyl transferase polypeptide of any one of paragraphs 1-49 composition wherein the PglB oligosaccharyltransferase is engineered.

53 A PglB from *Campylobacter coli* (PglB$_{C.\ coli}$) wherein the residue corresponding to amino acid X57 of SEQ ID NO:12 is substituted with a different amino acid to that found at that position in SEQ ID NO:12; optionally to A57R.

54. The PglB from *Campylobacter coli* (PglB$_{C.\ coli}$) of paragraph 53 wherein the residue corresponding to amino acid X463 of SEQ ID NO:12 is substituted with a different amino acid to that found at that position in SEQ ID NO:12; optionally to Y463W.

55. The PglB from *Campylobacter coli* (PglB$_{C.\ coli}$) of paragraph 53 or 54 wherein the residue corresponding to amino acid X480 of SEQ ID NO:12 is substituted with a different amino acid to that found at that position in SEQ ID NO:12; optionally to H480M.

56. The PglB from *Campylobacter coli* (PglB$_{C.\ coli}$) of any one of paragraphs 53-55 wherein the residue corresponding to amino acid X311 of SEQ ID NO:12 is substituted with a different amino acid to that found at that position in SEQ ID NO:12; optionally to N311V 57. The PblB from *Campylobacter coli* (PglB$_{C.\ coli}$) of any one of paragraphs 53-56 wherein the residue corresponding to amino acid X77 of SEQ ID NO:12 is substituted with a different amino acid to that found at that position in SEQ ID NO:12; optionally to Y77R.

58. A polynucleotide encoding a mutated PglB oligosaccharyltransferase polypeptide as found in any one of the preceding paragraphs.

59. A composition or host cell (for example a prokaryotic host cell or an *E. coli* host cell) comprising at least one PglB oligosaccharyltransferase of any one of paragraphs 1-57 or the polynucleotide of paragraph 58.

60. The composition or host cell of paragraph 59 wherein the at least one PglB oligosaccharyltransferase is engineered.

61. A host cell comprising the polynucleotide encoding a mutated PglB oligosaccharyltransferase of paragraph 58 or a PglB from *C. coli* having an amino acid sequence at least 85%, 90%, 95%, 97%, 98%, 99% or 100% identical to SEQ ID NO: 12, 13 or 14.

62. The host cell of paragraph 61 which is a prokaryotic host cell, optionally an *E. coli* host cell.

63. The host cell of paragraph 61 or 62 wherein the polynucleotide encoding PglB is integrated into the host cell genome or is expressed from a plasmid.

64. The host cell of paragraph 61, 62 or 63 comprising a further polynucleotide encoding a protein containing at least one glycosylation site comprising the amino acid sequence Asp/Glu-$Z_1$-Asn-$Z_2$-Ser/Thr wherein $Z_1$ and $Z_2$ may be any natural amino acid except Pro.

65. The host cell of any one of paragraphs 61-64 wherein the protein containing at least one glycosylation site is selected from the group consisting of exotoxin A of *P. aeruginosa* (EPA), CRM197, diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, and *C. jejuni* natural glycoproteins.

66. The host cell of paragraph 65 wherein the protein containing at least one glycosylation site is exoprotein A of *P. aeruginosa* (EPA).

67. The host cell of any one of paragraphs 61-66 wherein the protein containing at least one glycosylation site contains 2, 3 or 4 glycosylation sites.

68. The host cell of any one of paragraphs 61-67 comprising at least one polynucleotide encoding glycosyltransferase(s) required for the assembly of a specific oligosaccharide on an undecaprenyl lipid carrier.

69. The host cell of any one of paragraphs 61-68 wherein the specific oligosaccharide is an antigen, for example a bacterial O antigen or a bacterial capsular saccharide antigen.

70. The host cell of paragraph 69 wherein the specific oligosaccharide comprises an *E. coli* O-antigen, a *Salmonella* sp O-antigen, a *Pseudomonas* sp. O-antigen, a *Klebsiella* sp. O-antigen, an acinetobacter O antigen, a *Chlamydia trachomatis* antigen, a *Vibrio cholera* antigen, a *Listeria* sp. antigen, a *Legionella pneumophila* serotypes 1 to 15 antigen, a *Bordetella parapertussis* antigen, a *Burkholderia mallei* or *pseudomallei* antigen, a *Francisella tularensis* antigen, a *Campylobacter* sp. antigen; a *Clostridium difficile* antigen, a *Streptococcus* agalacficae antigen, a a *Neisseria meningitidis* antigen, a *Candida albicans* antigen, a *Haemophilus* influenza antigen, a *Enterococcus faecalis* antigen, a *Borrelia burgdorferi* antigen, a *Staphylococcus aureus* capsular saccharide antigen, a, *Haemophilus* influenza antigen, a *Leishmania major* antigen, a *Shigella* sp., or a *Streptococcus pneumoniae* capsular saccharide antigen (e.g. serotypes CP1, CP2, CP3, CP4, CPS, CP6 (A and B), CP7 (A,B,C), CP8, CP9 (A,L,N,V), CP10 (A,B,C,F), CP11 (A, B, C, D, F), CP12(A,B,F), CP13, CP14 CP15(A,B,C,F), CP16(A,F), CP17(A,F), CP18 (A,B,C,F), CP19(A,B,C,F), CP20, CP21, CP22(A,F), CP23(A,B,F), CP24(A,B,F), CP25(A,F), CP26, CP27, CP28(A,F), CP29, CP31, CP32(A,F), CP33(A, B, C, D, F), CPS34, CP35(A, B, C, D, F), CP36, CP37, CP38, CP39, CP40, CP41(A,F), CP42, CP43, CP44, CP45, CP46, CP47(A,F), CPS48).

71. The host cell of any one of paragraphs 61-70 wherein the specific oligosaccharide comprises a residue that is not GlcNAc at the reducing end of the oligosaccharide.

72. The host cell of any one of paragraphs 61-71 wherein the specific oligosaccharide comprises a glucose residue at the reducing terminus.

73. A process for preparing a glycosylated protein, comprising the steps of:
   (a) culturing the host cell of any one of paragraphs 61-72 under conditions suitable for the production of proteins; and
   (b) isolating the glycosylated protein from the host cell.

74. An in vitro process for preparing a glycosylated protein, comprising the steps of;
i) mixing together:
   a) the PglB oligosaccharyltransferase of any one of paragraphs 1-57;
   b) a protein comprising at least one glycosylation consensus sequence comprising the amino acid sequence Asp/Glu-$Z_1$-Asn-$Z_2$-Ser/Thr wherein $Z_1$ and $Z_2$ may be any natural amino acid except Pro; and
   c) a saccharide chain on a lipid carrier recognised by the PglB;
ii) incubating under conditions suitable for the enzymatic activity of PglB to transfer the saccharide chain to the at least one glycosylation consensus sequence of the protein to achieve a glycosylated protein; and
iii) isolating the glycosylated protein.

75. A glycosylated protein that is made by the process of paragraph 73 or 74.

76. A use of the PglB oligosaccharyltransferase or functional fragment thereof of any one of paragraphs 1-57 in the production of a glycosylated protein in which a saccharide is attached to an N residue of a glycosylation consensus sequence, comprising the amino acid sequence Asp/Glu-$Z_1$-Asn-$Z_2$-Ser/Thr wherein $Z_1$ and $Z_2$ may be any natural amino acid except Pro, of a protein.

77. The use of paragraph 76 wherein the sugar residue of the saccharide which is covalently attached to the N residue of the glycosylation sequence is not an N-acetyl sugar, for example N-acetyl glucosamine.

78. The use of the PglB oligosaccharyltransferase of paragraph 76 or 77 wherein a glucose residue in the saccharide is covalently attached to the N residue of the glycosylation sequence.

79. The use of any one of paragraphs 76-78 wherein the saccharide is a bacterial antigen, optionally a bacterial capsular polysaccharide antigen or a bacterial O-antigen.

80. The use of any one of paragraphs 76-79 wherein the saccharide is a Gram positive bacterial capsular polysaccharide antigen.

81. The use of any one of paragraphs 76-80 wherein the saccharide is an *E. coli O antigen, a Salmonella* sp antigen, a *Pseudomonas* sp. antigen, a *Klebsiella* sp antigen, a Acinetobacter O antigen, a *Chlamydia trachomatis* antigen, a *Vibrio cholera* antigen, a *Listeria* sp. Antigen, a *Legionella* pneumonia serotypes 1 to 15 antigen, a *Bordetella pertussis* antigen, a *Bordetalla parapertussis* antigen, a *Burkholderia mallei* or *pseudomallei* antigen, a *Francisella tularensis* antigen, a *Campylobacter* sp antigen, a *Clostridium difficile* antigen, a *Streptococcus pyogenes* antigen, a *Streptococcus agalactiae* antigen, a *Enterococcus faecalis* antigen, a *Borrelia burgdorferi* antigen, a *Neisseria meningitidis* antigen, a *Haemophilus* influenza antigen, a *Leishmania major* antigen, a *Shigella* sp. antigen, a

*Staphylococcus aureus* antigen, a *Salmonella enterica* antigen or a *Streptococcus pneumoniae* antigen.

82. The use of paragraph 81 wherein the saccharide is a *Streptococcus pneumoniae* capsular saccharide antigen.

83. The use of paragraph 82 wherein the *Streptococcus pneumoniae* capsular saccharide antigen is from serotype 1, 4, 19A, 22F, 23A, 35B or 8, preferably from serotype 8.

84. The use of any one of paragraphs 76-83 wherein the protein is a carrier protein comprising at least 1, 2 or 3 of the glycosylation consensus sequence(s).

85. The use of paragraph 84 wherein the carrier protein is *Pseudomonas aeruginosa* exoprotein A (EPA), diphtheria toxoid, CRM197, tetanus toxoid, pneumolysin.

86. The use of any one of paragraphs 76-85 wherein the PglB oligosaccharyltransferase or functional fragment thereof is capable of increasing the yield of glycosylation of the protein with the saccharide to produce a glycosylated protein by at least 1.5 fold, 2-fold, 3-fold, 5-fold, 10-fold, 20-fold, 50-fold, 100-fold, 200-fold, 500-fold, 700-fold, 1000-fold compared to a corresponding PglB oligosaccharyltransferase which has the sequence of SEQ ID NO:1.

87. The use of any one of paragraphs 76-86 wherein the PglB oligosaccharyltransferase or functional fragment thereof is capable of glycosylating at least 10%, 20%, 30%, 40%, 50%, 60%, 70%, 80% or 90% of the protein with a saccharide, wherein a glucose residue of the saccharide is covalently bound to the N residue of the glycosylation consensus sequence.

88. A use of a PglB oligosaccharyltransferase (OST) or functional fragment thereof of from *Campylobacter coli* ($PglB_{C.coli}$) in the production of a glycosylated protein in which a saccharide is attached to an N residue of a glycosylation consensus sequence, comprising the amino acid sequence Asp/Glu-$Z_1$-Asn-$Z_2$-Ser/Thr wherein $Z_1$ and $Z_2$ may be any natural amino acid except Pro, of a protein.

89. The use of paragraph 88 wherein the $PglB_{C.coli}$ has an amino acid sequence having at least 85%, 90%, 95%, 97%, 98% or 99% sequence identity to SEQ ID NO:12, 13 or 14, optionally to SEQ ID NO:12.

90. The use of paragraph 88 or 89 wherein the saccharide is selected from the group consisting of *S. flexneri* 2a, 3a and 6, and *E. coli O*18.

EXAMPLES

Various features and embodiments of the disclosure are illustrated in the following representative examples, which are intended to be illustrative, and not limiting.

Example 1

Plasmids and Strain Used to Assess the Activity of PglB Variants

The activity of PglB variants was tested in a derivative of *E. coli* W3110 with deletions of genes as described in WO 14/057109A1. Capsular polysaccharide-encoding loci were stably integrated into the *E. coli* chromosome based on the methods detailed in WO2014057109A1. Other required elements, including PglB, carrier proteins, supplementary biosynthetic enzymes and regulatory proteins were variously expressed from plasmids pEXT21 (Spec resistant, IPTG-inducible), pEXT22 (Kan resistant, IPTG-inducible), pEC415 (Kan resistant, arabinose-inducible) or pLAFR (tet resistant, constitutive) or derivatives thereof.

Plasmids:

| Name | Source |
|---|---|
| pEXT21 | Dykxhoorne et al., 1996 Gene 177: 133-136 |
| pEXT22 | Dykxhoorne et al., 1996 Gene 177: 133-136 |
| pEC415 | Schulz et al., 1998 Science 281, 1197-1200 |
| pLAFR1 | Friedmanet al., 1982 Gene 18(3): 289-96 |

Example 2

Detection of Glycosylation by ELISA from Small Scale Cultures

Variants of PglB were tested for their ability to catalyse the glycosylation of Exoprotein A from *Pseudomonas aeruginosa* (EPA) containing $D/E-Z_1-N-Z_2-S/T$ glycosylation sites (where $Z_1$ and $Z_2$ are not P) using a polysaccharide corresponding to that of *S. pneumoniae* serotype 8. Therefore a *E. coli* host cell was transformed with plasmids encoding glycosyltransferase genes required for the construction of a *S. pneumoniae* serotype 8 capsular polysaccharide, a variant PglB gene and EPA containing glycosylation sites.

Expression of the genes was induced using IPTG and arabinose and the *E. coli* host cells were grown overnight to allow expression of glycosyltransferases, PglB and EPA and glycosylation of EPA as follows.

The wells of a 96 deep well plate were filled with 1 ml of TB media and each well was inoculated with a single colony of host cell *E. coli* and incubated at 37 degrees C. overnight. Samples of each well were used to inoculate main cultures in a 96 deep well plate containing of 1 ml of TB supplemented with 10 mM $MgCl_2$ and appropriate antibiotics and were grown until an OD600 of 1.3-1.5 was reached. Cells were incubated with 1 mM IPTG and 0.1% arabinose overnight at 37 degrees C.

Periplasmic extracts were made by centrifuging the plates, removing supernatant and adding 0.2 ml of 50 mM Tris-HCl pH 7.5, 175 mM NaCl, 5 mM EDTA followed by shaking at 4 degrees C. to suspend the cells. 10 µl of 10 mg/ml polymyxin B was added to each well and the cells were incubated for 1 hour at 4 degrees C. The plate was centrifuged and the supernatant removed.

In order to isolate the glycosylated protein from the periplasmic extract, 120 µl of a 25% slurry of IMAC resin in 30 mM Tris pH 8.0, 10 mM imidazole, 500 mM NaCl was added to each well of a 96 well filter plate (Acroprep Advance) and placed on top of a Nunc ELISA plate. The plate was centrifuged and the flow through discarded. 150 µl of periplasmic extract and 37.5 ml of 5× binding buffer (150 mM Tris pH 8.0, 50 mM imidazole, 2.5M NaCl was added to each well. The samples were incubated for 30 minutes at room temperature. The plate was centrifuged and the flow through discarded and three more washing steps were carried out. Finally the glycosylated protein was eluted with 30 mM Tris pH 8.0, 500 mM imidazole, 200 mM NaCl, ready for use in an ELISA assay.

A sandwich ELISA was performed by coating the wells of a 96-well plate with an antibody that recognizes the saccharide part of the glycosylated protein (for example, a monoclonal antibody against *S. pneumoniae* serotype 8) diluted in PBS. The plate was incubated overnight at 4 degrees C. to allow coating. The plate was then washed with PBS containing 0.1% Tween. The plate was then blocked for 2 hours at room temperature using 5% bovine serum albumin in PBST. The plate was washed in PBST. The sample was diluted in PBST containing 1% BSA and incubated in the coated wells for one hour at room temperature. After washing a detection antibody, for example anti-Histag—horseradish peroxidase diluted in PBST containing 1% BSA was added to each well and incubated for one hour at room temperature. The plate was then washed before adding 3,3',5,5'-Tetramethylbenzidine liquid substrate, Supersensitive, for ELISA (Sigma-Aldrich). After a few minutes, the reaction was stopped by addition of 2M sulfuric acid. The results were obtained by reading the OD at 450 nm.

Results

As a starting point, mutations were generated in a PglB which already contained a mutation at N311V. A first round of variant generation identified Y77R as a mutation which further increased the OST activity of PglB (see FIG. 1). A PglB containing mutations at N311V and Y77R was subjected to mutation and promising variants were selected, sequenced and analysed for OST activity as described above. The fold increase in oligosaccharyltransferase activity of each variant was calculated and the results are shown in Table 3.

TABLE 3

| Improvement in engineered PglB OST activity in transferring *S. pneumoniae* 8 saccharide to a protein as determined by ELISA ROUND 2 | | |
|---|---|---|
| PglB Variant mutation | Amino acid substitution | Fold increase in OST activity |
| 57 | T R | T- 1.047, R-2.2755 |
| 63 | L Q | L-1.132, Q-1.146 |
| 94 | N | N-1.103 |
| 101 | W E H P R M G | W- 1.2635, E - 1.263, H-1.26, P-1.2595, R- 1.11325, M - 2.263, G - 1.235 |
| 176 | E G | E - 1.2805 |
| 191 | H D R Y | H-1.798, D-1.763, R-1.516, Y-2.017 |
| 193 | T H G F | T -1.2375, H-1.291, G-1.508, F-1.5055 |
| 233 | V | V-1.431 |
| 234 | H C W | H-1.761, C-1.302, W-1.838 |
| 286 | A Q L | A-1.296, Q-1.091, L-1.132 |
| 301 | P G F | P-1.210, G-1.3, F-1.135 |
| 319 | A Q L T | A-1.329, Q-1.423, L-1.724, T-1.626 |
| 397 | N L Q | N - 1.093, L - 1.1245, |
| 402 | R H | R-1.434, H-1.191 |
| 435 | A L F H R | A-1.214, L-1.442, F-1.719, H-1.213, R-1.471 |
| 446 | G | G-1.4375 |
| 462 | P C W T N | P-2.221, C-1.2895, W-2.112, T-1.362, N-1.247 |
| 479 | M | M-1.582 |
| 523 | R | R-1.171 |
| 532 | H | H-1.4085 |
| 605 | D | D-1.209 |
| 610 | P L R D A | P-1.227, I-1.34, R-1.518, D-1.245, A-1.467 |
| 645 | L S H | L-1.377, 1.225, H-1.481 |
| 676 | Q W G | Q-1.247, W-1.84, G-1.279 |
| 695 | I Q | I-1.218 |

The mutations 57T, 57R, 63L, 63Q, 94N, 101W, 101E, 101H, 101P, 101R, 101M, 101G, 172E, 176E, 176G, 191H, 191D, 101R, 101Y, 193T, 193H, 193G, 193F, 233V, 234H, 234C, 234W, 255H, 286A, 286Q, 286L, 301P, 301G, 301F, 319A, 319Q, 319L, 319T, 397N, 397L, 397Q, 402R, 402H, 425S, 435A, 435L, 435F, 435H, 435R, 446G, 462P, 462C, 462W, 462T, 462N 479M, 523R, 532H, 601G, 605D, 606P, 610P, 610L, 610R, 610D, 610A, 645L, 645S, 645H, 676Q, 676W, 676G, 6951 and 695Q were noted as mutations which appeared in several PglB variants which were capable of enhanced catalysis of the addition of a *S. pneumoniae* serotype 8 saccharide to a carrier protein. Out of these, the A57R mutation was selected as a promising mutation to take forward into further rounds due to its high increase in OST activity, its frequency of appearance in promising variants and its position in the PglB structure.

The ability of residues 462 and 479 to synergise in order to produce higher fold increases in OST activity when both residues are mutated is demonstrated in the following table showing results for individual:

| PglB variant mutation | Fold increase in OST activity | Sample number |
|---|---|---|
| H479M | 7.483 | S00099450 |
| H479M | 6.8 | S00099887 |
| Y462W | 2.377 | S00109538 |
| Y462W | 2.164 | S00109534 |
| Y462W + H479M | 12.404 | S00099448 |
| Y462W + H479M + A84W+ M155Q + T523R | 15.071 | S00099611 |

In a further round of experiments, the favourable A57R mutation was added to the Y77R and N311V mutations. Further mutations were added to PglB with A57R, Y77R and N311V mutations. The new mutations were tested for increased PglB activity by ELISA using *S. pneumoniae* PS8 as the saccharide added to EPA. The results are shown in Table 4 below.

TABLE 4

| Improvement in engineered PglB OST activity in transferring *S. pneumoniae* 8 saccharide to a protein as determined by ELISA ROUND 3 | | |
|---|---|---|
| PglB Variant mutation | Amino acid substitution | Fold increase in OST activity |
| 78 | T | T-1.2455 |
| 84 | W | W-1.361 |
| 300 | L | L-1.123 |
| 301 | G P | G-1.419. P-2.22 |
| 306 | H | H-1.375 |
| 462 | N T W | N-1.76, T-1.4246, W-1.681, |
| 479 | M | M-5.5548 |
| 570 | R V | R-1.083, V-1.419 |
| 462W + 479M | | 12.404, 8.368 |

From this round, the combination of 462W and 479M was found in 52 separate PglB variants, producing fold increases in OST activity of up to 15 fold, or 8-12 fold where these mutations were the only new mutations present. These mutations are considered as important for improving the efficiency of PglB for glycosylation of proteins with saccharides containing a glucose residue at the reducing end of the saccharide.

The mutations N300L, L301P, F308W and L570R were also noted as mutations which appeared in several PglB variants which were capable of enhanced catalysis of the addition of a *S. pneumoniae* serotype 8 saccharide to a carrier protein.

N300L, L301P, F308W, Y462W, H479M and L570R were selected as promising mutations to take forward into further rounds of mutation/selection due to their ability to increase OST activity, their frequency of appearance in efficient PglB variants and their position in the molecular structure of PglB. These residues were added to the Y77R, N311V and A57R mutations and further point mutations were tested for their ability to improve the activity of PglB to add a *S. pneumoniae* serotype 8 saccharide to a protein. The results are shown in Table 5 below

TABLE 5

| Improvement in engineered PglB OST activity in transferring *S. pneumoniae* 8 saccharide to a protein as determined by ELISA ROUND 4 | | |
|---|---|---|
| PglB Variant mutation | Amino acid substitution | Fold increase in OST activity |
| 218 | A | A-3.084 |
| 308 | F | F-1.519 |
| 319 | L | L-1.218 |
| 382 | S | S-2.77 |
| 523 | R | R-1.086 |
| L191Y, Y286Q, S295L, A382S, K482R + T523R | | 9.166 |

From this round L191Y, Y286Q, S295L, A382S, K482R and T523R mutations were added to the previously tested mutations resulting in a reference PglB containing the following mutations: Y77R, N311V, A57R, N300L, L301P, F308W, Y462W, H479M, L570R, L191Y, Y286Q, S295L, A382S, K482R and T523R. In the next round, further mutations were tested for their ability to further increase the efficiency of a PglB containing Y77R, N311V, A57R, N300L, L301P, F308W, Y462W, H479M, L570R, round L191Y, Y286Q, S295L, A382S, K482R and T523R further and the results are shown in Table 6 below.

TABLE 6

| Improvement in engineered PglB OST activity in transferring *S. pneumoniae* 8 saccharide to a protein as determined by ELISA ROUND 5 | | |
|---|---|---|
| PglB Variant mutation | Amino acid substitution | Fold increase in OST activity |
| 21 | S L | S - 1.7; L - 4.415 |
| 27 | S A M W | S - 2.01; A - 2.156; M - 2.21; W - 2.505 |
| 42 | W C | W - 1.32; C - 3.566 |
| 44 | M H | M - 1.348; H - 1.76 |
| 53 | S I H | S - 1.556; I - 1.611; H 2.298 |
| 80 | A D | A - 1.647; D - 1.788 |
| 97 | I | I - 3.456 |
| 297 | K Y S R | K - 1.96; Y - 2.033; S - 2.1635; R - 2.51 |
| 317 | S A | S - 1.3805; A - 2.283 |
| 341 | L | L - 2.103 |
| 383 | M | M - 2.208 |
| 388 | I M | I - 1.34; M - 2.261 |
| 410 | I | I - 2.143 |
| 421 | G | G - 2.235 |
| 480 | W Q I N M T | W - 1.246; Q - 1.715; I - 1.727; N - 1.864; M - 1.924; T - 4.098 |
| 486 | N V C L | N - 1.231; V - 1.479; C - 2.315; L - 4.4 |

From this round a E297R was selected due to the increase in activity produced where this mutation was present and the frequency of appearance of this mutation. A S80D mutation was also selected as a promising residue due to its frequency of appearance in variants with higher levels of OST activity.
Summary of Evolution Over the course of this study, the activity of PglB in the context of adding a *S. pneumoniae* serotype 8 saccharide to a protein containing a glycosylation consensus sequence was increased by over three orders of magnitude (FIG. 1). The introduction of A57R into a PglB into a PglB enzyme already containing Y77R and N311V mutations led to a 24 fold increase in PglB activity. The further addition of N300L, L301P, F308W, Y462W, H479M and L750R led to a cumulative increase in activity of 360 fold. The further incorporation of L191Y, Y286Q, S295L, A382S, K482R and T523R led to a cumulative increase of activity of 2520 fold and the further inclusion of a E297R mutation led to a cumulative 5040 fold increase in activity. Further rounds of evolution allowed small increases in PglB activity, however the largest increases in activity were achieved in rounds 1-3 (see FIG. 1).

Example 3

Measurement of PglB Activity at Shake Flask Volume

Some of the mutated PglB enzymes were used in larger scale assays in order to confirm increases in activity in glycosylating an EPA protein containing 3 glycosylation consensus sequences with *S. pneumoniae* serotype 8 saccharide.

Electrocompetent *E. coli* strains were transformed with the required plasmids by electroporation. The cells were allowed to recover for 1 hour and plated onto agar plates containing appropriate antibiotics and 2 mM MgCl$_2$. The plates were incubated overnight. A preculture was made by inoculating TB media containing appropriate antibiotics and 10 mM MgCl$_2$ with cells from the plate and incubating overnight.

The main culture was started by diluting the preculture in TB medium containing appropriate antibiotics and 10 mM MgCl$_2$ to an OD600 nm of 0.1. The culture was grown to an OD600 nm of 0.8-1.0 and the cells were then induced using an appropriate inducer (e.g. arabinose of IPTG). The cell were then incubated overnight.

A periplasmic extract was made by the following process. The culture was centrifuged to pellet the *E. coli*. The supernatant was discarded and the pellet resuspended in 30 mM Tris-HCl pH 8.5, 1 mM EDTA, 20% sucrose. Lysozyme was added to a final concentration of 1 mg/ml and the cells were incubated with the lysozyme for 25 minutes at 4 degrees C. with shaking. After centrifugation, the periplasmic extract was retained.

1 ml of periplasmic extract was mixed with 0.25 ml of 150 mM Tris pH8.0, 50 mM imidazole, 2.5M NaCl and 20 mM MgCl$_2$. 0.2 ml of a 50% slurry or pre-equilibrated NiNTA agarose (Qiagen) was added and the sample incubated for 20 minutes at room temperature with shaking. The IMAC resin was centrifuged and the supernatant discarded. 0.5 ml of 30 mM Tris pH 8.0, 10 mM imidazole, 500 mM NaCl with 0.1% n-Dodecyl-B-maltose was added, the resin centrifuged and the supernatant discarded. The resin was further washed three times with 30 mM Tris pH 8.0, 10 mM imidazole, 500 mM NaCl. 0.2 ml of elution buffer (30 mM Tris pH 8.0, 10 mM imidazole, 50 mM NaCl) was added to the resin and incubated for 5 minutes at room temperature. The eluate was recovered and used for further analysis.

The amount of glycosylation was assessed by SDS-PAGE and western blotting. After running the samples on an SDS-PAGE, the proteins were transferred to nitrocellulose membrane. The membrane was blocked with 10% milk for at least 10 minutes. After blocking the membrane was incubated with a first antibody (a mouse Mab against *S. pneumoniae* serotype 8 for example) in PBS-T containing 1% milk for 1 hour. After washing with PBS-T, the membrane was incubated with a second antibody—HRP conjugate (anti-mouse IgG Fc HRP) in PBS-T with 1% milk for an hour. The membrane was washed in PBS-T and developed using BioFX TMB One Component HRP membrane substrate.

Results

FIG. 1 shows a gel in which enhanced levels of EPA glycosylated with *S. pneumoniae* serotype 8 capsular saccharide were obtained. The most important increases in OST activity were achieved in rounds 1-3, with smaller fold increases in activity being achieved in subsequent rounds. At a shake flask scale, yield increases of well over 1,000 fold were achieved.

Example 4

The Mutated PglB Oligosaccharyltransferases Show Enhanced Efficiency at Catalyzing Glycosylation with Further Saccharides Further experiments were carried out to investigate whether the modified PglB OSTs from each round could produce higher yields of further bioconjugates where different saccharides were bonded to the EPA protein.

The protocols of example 2 and 3 were used to make bioconjugates of *S. pneumoniae* serotype 22F covalently bonded to modified EPA. The results of ELISA and western blotting show that good yields of *S. pneumoniae* serotype 22F-EPA conjugate could be achieved using the modified PglBs generated from rounds 3, 4 and 5 of example 2. The yield using a round 3 PglB with mutations at A57R, Y77R and N311V is good but is improved further by using the PglB from round 4 which contains additional point mutations at N300L, L301P, F308W, Y462W, H479M and L570R. The yield is further improved by using the round 5 PglB containing further mutations at L191Y, Y286Q, S295L and A382S.

Figure 3:
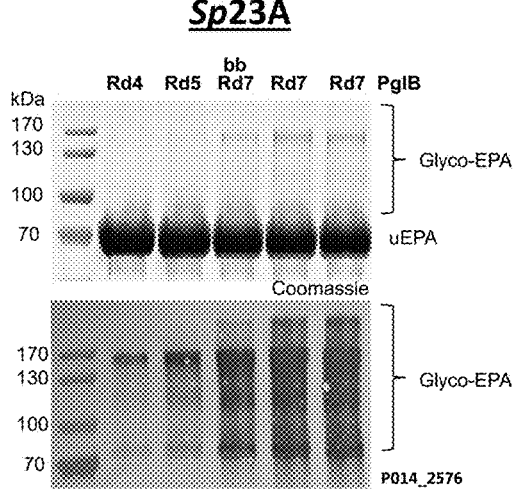
FIG. 3—The mutated PglBs have increased activity for transfer of *S. pneumoniae* serotypes 23A and 35B to a protein. Panel A shows the results of a coomassie gel and a western blot showing increased glycosylation of EPA with *S. pneumoniae* serotype 23A polysaccharide when round 4, 5 and 7 PglBs were used to catalyse the transfer. Panel B shows increased glycosylation of EPA when a round 3 PglB was used to transfer the capsular saccharide of *S. pneumoniae* serotype 35B, compared to using wild type PglB.
Figure 3:
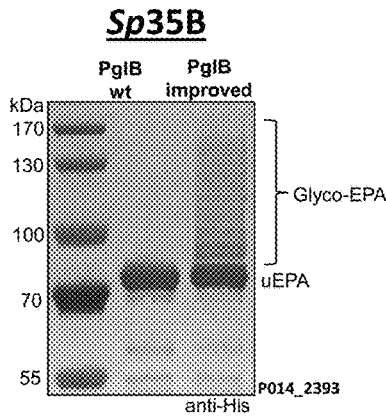

The mutated PglB OSTs were also efficient at catalysing the addition of *S. pneumoniae* serotype 23A saccharide to a protein as shown in FIG. 3A. The mutated PglB OSTs were also efficient at catalysing the addition of *S. pneumoniae* serotype 35B to a protein as shown in FIG. 3B. The inclusion of substitutions at A57R, Y77R and N311V led to the improved activity shown in FIG. 3B.

Figure 4:
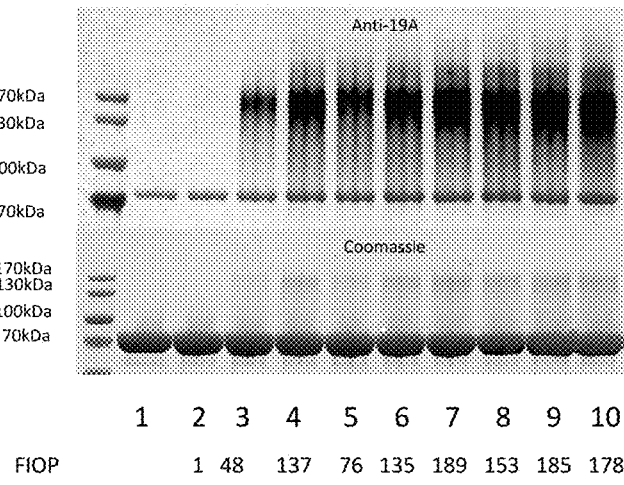
FIG. 4—The mutated PglBs have increased activity for transfer of *S. pneumoniae* serotype 19A to a protein. Coomassie straining and western blot results for the amount of EPA glycosylated with *S. pneumoniae* serotype 19A using: lane 1—inactive PglB, lane 2—PglB containing Y77R, N311V and H479M mutations, lane 3—Round 6 PglB, Lanes 4-10— various round 7 PglB mutations.

The mutated PglB OSTs were also efficient at catalysing the addition of *S. pneumoniae* serotype 19A to a protein as shown in FIG. 4.

Sequence Listing
Wild type PglB from *C. jejuni*. (pLMTB1937)

SEQ ID NO: 1

MLKKEYLKNPYLVLFAMIILAYVFSVFCRFYWVWWASEFNEYFFNNQLMIISNDGYAFAEGARDM

IAGFHQPNDLSYYGSSLSALTYWLYKITPFSFESIILYMSTFLSSLVVIPTILLANEYKRPLMGFVAAL

LASIANSYYNRTMSGYYDTDMLVIVLPMFILFFMVRMILKKDFFSLIALPLFIGIYLWWYPSSYTLNV

ALIGLFLIYTLIFHRKEKIFYIAVILSSLTLSNIAWFYQSAIIVILFALFALEQKRLNFMIIGILGSATLIFLI

LSGGVDPILYQLKFYIFRSDESANLTQGFMYFNVNQTIQEVENVDLSEFMRRISGSEIVFLFSLFGFV

WLLRKHKSMIMALPILVLGFLALKGGLRFTIYSVPVMALGFGFLLSEFKAIMVKKYSQLTSNVCIVF

ATILTLAPVFIHIYNYKAPTVFSQNEASLLNQLKNIANREDYVVTWWDYGYPVRYYSDVKTLVDGG

KHLGKDNFFPSFALSKDEQAAANMARLSVEYTEKSFYAPQNDILKTDILQAMMKDYNQSNVDLFL

ASLSKPDFKIDTPKTRDIYLYMPARMSLIFSTVASFSFINLDTGVLDKPFTFSTAYPLDVKNGEIYLSN

GVVLSDDFRSFKIGDNVVSVNSIVEINSIKQGEYKITPIDDKAQFYIFYLKDSAIPYAQFILMDKTMFN

SAYVQMFFLGNYDKNLFDLVINSRDAKVFKLKI

PglB *C. jejuni* containing N311V and Y77R mutations (DLMTB4028)

SEQ ID NO: 2

MLKKEYLKNPYLVLFAMIILAYVFSVFCRFYWVWWASEFNEYFFNNQLMIISNDGYAFAEGARDM

IAGFHQPNDLS<u>R</u>YGSSLSALTYWLYKITPFSFESIILYMSTFLSSLVVIPTILLANEYKRPLMGFVAALL

ASIANSYYNRTMSGYYDTDMLVIVLPMFILFFMVRMILKKDFFSLIALPLFIGIYLWWYPSSYTLNV

ALIGLFLIYTLIFHRKEKIFYIAVILSSLTLSNIAWFYQSAIIVILFALFALEQKRLNFMIIGILGSATLIFLI

LSGGVDPILYQLKFYIFRSDESANLTQGFMYFNV<u>V</u>QTIQEVENVDLSEFMRRISGSEIVFLFSLFGFV

WLLRKHKSMIMALPILVLGFLALKGGLRFTIYSVPVMALGFGFLLSEFKAIMVKKYSQLTSNVCIVF

ATILTLAPVFIHIYNYKAPTVFSQNEASLLNQLKNIANREDYVVTWWDYGYPVRYYSDVKTLVDGG

KHLGKDNFFPSFALSKDEQAAANMARLSVEYTEKSFYAPQNDILKTDILQAMMKDYNQSNVDLFL

ASLSKPDFKIDTPKTRDIYLYMPARMSLIFSTVASFSFINLDTGVLDKPFTFSTAYPLDVKNGEIYLSN

GVVLSDDFRSFKIGDNVVSVNSIVEINSIKQGEYKITPIDDKAQFYIFYLKDSAIPYAQFILMDKTMFN

SAYVQMFFLGNYDKNLFDLVINSRDAKVFKLKI

PglB *C. jejuni* with A57R, Y77R and N311V mutations (DLMTB4768)

SEQ ID NO: 3

MLKKEYLKNPYLVLFAMIILAYVFSVFCRFYWVWWASEFNEYFFNNQLMIISNDGYRFAEGARDM

IAGFHQPNDLSRYGSSLSALTYWLYKITPFSFESIILYMSTFLSSLVVIPTILLANEYKRPLMGFVAALL

ASIANSYYNRTMSGYYDTDMLVIVLPMFILFFMVRMILKKDFFSLIALPLFIGIYLWWYPSSYTLNV

ALIGLFLIYTLIFHRKEKIFYIAVILSSLTLSNIAWFYQSAIIVILFALFALEQKRLNFMIIGILGSATLIFLI

LSGGVDPILYQLKFYIFRSDESANLTQGFMYFNVVQTIQEVENVDLSEFMRRISGSEIVFLFSLFGFV

WLLRKHKSMIMALPILVLGFLALKGGLRFTIYSVPVMALGFGFLLSEFKAIMVKKYSQLTSNVCIVF

ATILTLAPVFIHIYNYKAPTVFSQNEASLLNQLKNIANREDYVVTWWDYGYPVRYYSDVKTLVDGG

KHLGKDNFFPSFALSKDEQAAANMARLSVEYTEKSFYAPQNDILKTDILQAMMKDYNQSNVDLFL

ASLSKPDFKIDTPKTRDIYLYMPARMSLIFSTVASFSFINLDTGVLDKPFTFSTAYPLDVKNGEIYLSN

GVVLSDDFRSFKIGDNVVSVNSIVEINSIKQGEYKITPIDDKAQFYIFYLKDSAIPYAQFILMDKTMFN

SAYVQMFFLGNYDKNLFDLVINSRDAKVFKLKI

PglB *C. jejuni* with A57R, Y77R, N300L, L301P, F308W, N311V,
Y462W, H479M, L570R mutations (pLMTB5298)

SEQ ID NO: 4

MLKKEYLKNPYLVLFAMIILAYVFSVFCRFYWVWWASEFNEYFFNNQLMIISNDGYRFAEGARDM

IAGFHQPNDLSRYGSSLSALTYWLYKITPFSFESIILYMSTFLSSLVVIPTILLANEYKRPLMGFVAALL

ASIANSYYNRTMSGYYDTDMLVIVLPMFILFFMVRMILKKDFFSLIALPLFIGIYLWWYPSSYTLNV

ALIGLFLIYTLIFHRKEKIFYIAVILSSLTLSNIAWFYQSAIIVILFALFALEQKRLNFMIIGILGSATLIFLI

LSGGVDPILYQLKFYIFRSDESALPTQGFMYWNVVQTIQEVENVDLSEFMRRISGSEIVFLFSLFGFV

WLLRKHKSMIMALPILVLGFLALKGGLRFTIYSVPVMALGFGFLLSEFKAIMVKKYSQLTSNVCIVF

ATILTLAPVFIHIYNYKAPTVFSQNEASLLNQLKNIANREDYVVTWWDYGWPVRYYSDVKTLVDG

-continued

GKMLGKDNFFPSFALSKDEQAAANMARLSVEYTEKSFYAPQNDILKTDILQAMMKDYNQSNVDLF

LASLSKPDFKIDTPKTRDIYLYMPARMSRIFSTVASFSFINLDTGVLDKPFTFSTAYPLDVKNGEIYLS

NGVVLSDDFRSFKIGDNVVSVNSIVEINSIKQGEYKITPIDDKAQFYIFYLKDSAIPYAQFILMDKTMF

NSAYVQMFFLGNYDKNLFDLVINSRDAKVFKLKI

PglB *C. jejuni* with A57R, Y77R, L191Y, Y286Q, S295L, N300L, L301P,
F308W, N311V, A382S, Y462W, H479M, K482R, T523R, L570R mutations
(pLMTB5685)

SEQ ID NO: 5

MLKKEYLKNPYLVLFAMIILAYVFSVFCRFYWVWWASEFNEYFFNNQLMIISNDGYRFAEGARDM

IAGFHQPNDLSRYGSSLSALTYWLYKITPFSFESIILYMSTFLSSLVVIPTILLANEYKRPLMGFVAALL

ASIANSYYNRTMSGYYDTDMLVIVLPMFILFFMVRMILKKDFFSLIALPLFIGIYYWWYPSSYTLNV

ALIGLFLIYTLIFHRKEKIFYIAVILSSLTLSNIAWFYQSAIIVILFALFALEQKRLNFMIIGILGSATLIFLI

LSGGVDPILQQLKFYIFRLDESALPTQGFMYWNVVQTIQEVENVDLSEFMRRISGSEIVFLFSLFGFV

WLLRKHKSMIMALPILVLGFLALKGGLRFTIYSVPVMSLGFGFLLSEFKAIMVKKYSQLTSNVCIVF

ATILTLAPVFIHIYNYKAPTVFSQNEASLLNQLKNIANREDYVVTWWDYGWPVRYYSDVKTLVDG

GKMLGRDNFFPSFALSKDEQAAANMARLSVEYTEKSFYAPQNDILKRDILQAMMKDYNQSNVDLF

LASLSKPDFKIDTPKTRDIYLYMPARMSRIFSTVASFSFINLDTGVLDKPFTFSTAYPLDVKNGEIYLS

NGVVLSDDFRSFKIGDNVVSVNSIVEINSIKQGEYKITPIDDKAQFYIFYLKDSAIPYAQFILMDKTMF

NSAYVQMFFLGNYDKNLFDLVINSRDAKVFKLKI

PglB *C. jejuni* with A57R, Y77R, L191Y, Y286Q, S295L, E297R, N300L,
L301P, F308W, N311V, A382S, Y462W, H479M, K482R, T523R, L570R
mutations (pLMTB5967)

SEQ ID NO: 6

MLKKEYLKNPYLVLFAMIILAYVFSVFCRFYWVWWASEFNEYFFNNQLMIISNDGYRFAEGARDM

IAGFHQPNDLSRYGSSLSALTYWLYKITPFSFESIILYMSTFLSSLVVIPTILLANEYKRPLMGFVAALL

ASIANSYYNRTMSGYYDTDMLVIVLPMFILFFMVRMILKKDFFSLIALPLFIGIYYWWYPSSYTLNV

ALIGLFLIYTLIFHRKEKIFYIAVILSSLTLSNIAWFYQSAIIVILFALFALEQKRLNFMIIGILGSATLIFLI

LSGGVDPILQQLKFYIFRLDRSALPTQGFMYWNVVQTIQEVENVDLSEFMRRISGSEIVFLFSLFGFV

WLLRKHKSMIMALPILVLGFLALKGGLRFTIYSVPVMSLGFGFLLSEFKAIMVKKYSQLTSNVCIVF

ATILTLAPVFIHIYNYKAPTVFSQNEASLLNQLKNIANREDYVVTWWDYGWPVRYYSDVKTLVDG

GKMLGRDNFFPSFALSKDEQAAANMARLSVEYTEKSFYAPQNDILKRDILQAMMKDYNQSNVDLF

LASLSKPDFKIDTPKTRDIYLYMPARMSRIFSTVASFSFINLDTGVLDKPFTFSTAYPLDVKNGEIYLS

NGVVLSDDFRSFKIGDNVVSVNSIVEINSIKQGEYKITPIDDKAQFYIFYLKDSAIPYAQFILMDKTMF

NSAYVQMFFLGNYDKNLFDLVINSRDAKVFKLKI

PglB *C. jejuni* with A57R, Y77R, S80D, L191Y, Y286Q, S295L, E297R,
N300L, L301P, F308W, N311V, A382S, Y462W, H479M, K482R, T523R, L570R
mutations (pLMTB6274)

SEQ ID NO: 7

MLKKEYLKNPYLVLFAMIILAYVFSVFCRFYWVWWASEFNEYFFNNQLMIISNDGYRFAEGARDM

IAGFHQPNDLSRYGDSLSALTYWLYKITPFSFESIILYMSTFLSSLVVIPTILLANEYKRPLMGFVAAL

LASIANSYYNRTMSGYYDTDMLVIVLPMFILFFMVRMILKKDFFSLIALPLFIGIYYWWYPSSYTLN

VALIGLFLIYTLIFHRKEKIFYIAVILSSLTLSNIAWFYQSAIIVILFALFALEQKRLNFMIIGILGSATLIF

LILSGGVDPILQQLKFYIFRLDRSALPTQGFMYWNVVQTIQEVENVDLSEFMRRISGSEIVFLFSLFGF

VWLLRKHKSMIMALPILVLGFLALKGGLRFTIYSVPVMSLGFGFLLSEFKAIMVKKYSQLTSNVCIV

FATILTLAPVFIHIYNYKAPTVFSQNEASLLNQLKNIANREDYVVTWWDYGWPVRYYSDVKTLVD

GGKMLGRDNFFPSFALSKDEQAAANMARLSVEYTEKSFYAPQNDILKRDILQAMMKDYNQSNVD

-continued

LFLASLSKPDFKIDTPKTRDIYLYMPARMSRIFSTVASFSFINLDTGVLDKPFTFSTAYPLDVKNGEIY

LSNGVVLSDDFRSFKIGDNVVSVNSIVEINSIKQGEYKITPIDDKAQFYIFYLKDSAIPYAQFILMDKT

MFNSAYVQMFFLGNYDKNLFDLVINSRDAKVFKLKI

PelB *C. jejuni* with A57R, Y77R, S80D, I187V, L191Y, Y286Q, S295L,
E297R, N300L, L301P, F308W, N311V, I359Q, A382S, N406I, Y462W,
H479M, K482R, T523R, L570R mutations (pLMTB6526)

SEQ ID NO: 8

MLKKEYLKNPYLVLFAMIILAYVFSVFCRFYWVWWASEFNEYFFNNQLMIISNDGYRFAEGARDM

IAGFHQPNDLSRYGDSLSALTYWLYKITPFSFESIILYMSTFLSSLVVIPTILLANEYKRPLMGFVAAL

LASIANSYYNRTMSGYYDTDMLVIVLPMFILFFMVRMILKKDFFSLIALPLFVGIYYWWYPSSYTLN

VALIGLFLIYTLIFHRKEKIFYIAVILSSLTLSNIAWFYQSAIIVILFALFALEQKRLNFMIIGILGSATLIF

LILSGGVDPILQQLKFYIFRLDRSALPTQGFMYWNVVQTIQEVENVDLSEFMRRISGSEIVFLFSLFGF

VWLLRKHKSMIMALPQLVLGFLALKGGLRFTIYSVPVMSLGFGFLLSEFKAIMVKKYSQLTSIVCIV

FATILTLAPVFIHIYNYKAPTVFSQNEASLLNQLKNIANREDYVVTWWDYGWPVRYYSDVKTLVD

GGKMLGRDNFFPSFALSKDEQAAANMARLSVEYTEKSFYAPQNDILKRDILQAMMKDYNQSNVD

LFLASLSKPDFKIDTPKTRDIYLYMPARMSRIFSTVASFSFINLDTGVLDKPFTFSTAYPLDVKNGEIY

LSNGVVLSDDFRSFKIGDNVVSVNSIVEINSIKQGEYKITPIDDKAQFYIFYLKDSAIPYAQFILMDKT

MFNSAYVQMFFLGNYDKNLFDLVINSRDAKVFKLKI

PglB of *C. jejuni*

SEQ ID NO: 9

MLKKEYLKNP YLVLFAMIIL AYVFSVFCRF YWVWWASEFN EYFFNNQLMI

ISNDGYAFAE

GARDMIAGFH QPNDLSYYGS SLSALTYWLY KITPFSFESI ILYMSTFLSS

LVVIPTILLA

NEYKRPLMGF VAALLASIAN SYYNRTMSGY YDTDMLVIVL PMFILFFMVR

MILKKDFFSL

IALPLFIGIY LWWYPSSYTL NVALIGLFLI YTLIFHRKEK IFYIAVILSS

LTLSNIAWFY

QSAIIVILFA LFALEQKRLN FMIIGILGSA TLIFLILSGG VDPILYQLKF

YIFRSDESAN

LTQGFMYFNV NQTIQEVENV DLSEFMRRIS GSEIVFLFSL FGFVWLLRKH

KSMIMALPIL

VLGFLALKGG LRFTIYSVPV MALGFGFLLS EFKAIMVKKY SQLTSNVCIV

FATILTLAPV

FIHIYNYKAP TVFSQNEASL LNQLKNIANR EDYVVTWWDY GYPVRYYSDV

KTLVDGGKHL

GKDNFFPSFA LSKDEQAAAN MARLSVEYTE KSFYAPQNDI LKTDILQAMM

KDYNQSNVDL

FLASLSKPDF KIDTPKTRDI YLYMPARMSL IFSTVASFSF INLDTGVLDK

PFTFSTAYPL

-continued

DVKNGEIYLS NGVVLSDDFR SFKIGDNVVS VNSIVEINSI KQGEYKITPI

DDKAQFYIFY

LKDSAIPYAQ FILMDKTMFN SAYVQMFFLG NYDKNLFDLV INSRDAKVFK

LKIYPYDVPD

YA

PglB of *C. lari*

SEQ ID NO: 10

MKLQQNFTDN NSIKYTCILI LIAFAFSVLC RLYWVAWASE

FYEFFFNDQL

MITTNDGYAF AEGARDMIAG FHQPNDLSYF GSSLSTLTYW

LYSILPFSFE SIILYMSAFF ASLIVVPIIL IAREYKLTTY

GFIAALLGSI ANSYYNRTMS GYYDTDMLVL VLPMLILLTF

IRLTINKDIF TLLLSPVFIM IYLWWYPSSY SLNFAMIGLF

GLYTLVFHRK EKIFYLTIAL MIIALSMLAW QYKLALIVLL

FAIFAFKEEK INFYMIWALI FISILILHLS GGLDPVLYQL

KFYVFKASDV QNLKDAAFMY FNVNETIMEV NTIDPEVFMQ

RISSSVLVFI LSFIGFILLC KDHKSMLLAL PMLALGFMAL

RAGLRFTIYA VPVMALGFGY FLYAFFNFLE KKQIKLSLRN

KNILLILIAF FSISPALMHI YYYKSSTVFT SYEASILNDL

KNKAQREDYV VAWWDYGYPI RYYSDVKTLI DGGKHLGKDN

FFSSFVLSKE QIPAANMARL SVEYTEKSFK ENYPDVLKAM

VKDYNKTSAK DFLESLNDKD FKFDTNKTRD VYIYMPYRML

RIMPVVAQFA NTNPDNGEQE KSLFFSQANA IAQDKTTGSV

MLDNGVEIIN DFRALKVEGA SIPLKAFVDI ESITNGKFYY

NEIDSKAQIY LLFLREYKSF VILDESLYNS SYIQMFLLNQ

YDQDLFEQIT NDTRAKIYRL KR

SEQ ID NO: 11

MLKKEYLKNPYLVLFAMIILAYVFSVFCRFYWVWWASEFNEYFFNNQLMIISNDGYAFAEGARDM

IAGFHQPNDLSHYGSSLSALTYWLYKITPFSFESIILYMSTFLSSLVVIPTILLANEYKRPLMGFVAAL

LASIANSYYNRTMSGYYDTDMLVIVLPMFILFFMVRMILKKDFFSLIALPLFIGIYLWWYPSSYTLNV

ALIGLFLIYTLIFHRKEKIFYIAVILSSLTLSNIAWFYQSAIIVILFALFALEQKRLNFMIIGILGSATLIFLI

LSGGVDPILYQLKFYIFRSDESANLTQGFMYFNVVQTIQEVENVDLSEFMRRISGSEIVFLFSLFGFV

WLLRKHKSMIMALPILVLGFLALKGGLRFTIYSVPVMALGFGFLLSEFKAIMVKKYSQLTSNVCIVF

ATILTLAPVFIHIYNYKAPTVFSQNEASLLNQLKNIANREDYVVTWWDYGYPVRYYSDVKTLVDGG

KHLGKDNFFPSFALSKDEQAAANMARLSVEYTEKSFYAPQNDILKTDILQAMMKDYNQSNVDLFL

ASLSKPDFKIDTPKTRDIYLYMPARMSLIFSTVASFSFINLDTGVLDKPFTFSTAYPLDVKNGEIYLSN

GVVLSDDFRSFKIGDNVVSVNSIVEINSIKQGEYKITPIDDKAQFYIFYLKDSAIPYAQFILMDKTMFN

SAYVQMFFLGNYDKNLFDLVINSRDAKVFKLKI

PglB from Campylobacter_coli_jv20.ASM14683v1 EFM37568

SEQ ID NO: 12

MLKKEYFKNPTFILLAFIILAYVFSVLCRFYWIFWASEFNEYFFNNELMIISNDGYAFAEGARDMIAG

FHQPNDLSYYGSSLSTLTYWFYKITPFSLESIFIYISTFLSSLVIPLILIANEYKRPLMGFVAALLASIA

NSYYNRTMSGYYDTDMLVIVLAMMIVFFMIRLILKKDLLSLITLPLFVGIYLWWYPSSYTLNVALLG

-continued

LFFIYTLVFHIKEKTLYMAIILASITLSNIAWFYQSAIIVILFSLFVLQNKRFSFALLGILGLATLVFLILS

GGIDPILYQLKFYIFRSDESANLAQGFMYFNVNQTIQEVESIDLSIFMQRISGSELVFFVSLIGFIFLVR

KHKSMILALPMLALGFLALKSGLRFTIYAVPVLALGFGFLMSLLQERKQKNNNTYWWANIGVFIFT

FLSLIPMFYHINNYKAPTVFSQNEATKLDELKKIAQREDYVVTWWDYGYPIRYYSDVKTLADGGK

HLGKDNFFPSFVLSKDQVAAANMARLSVEYTEKSFYAPLNDILKNDLLQAMMKDYNQNNVDLFL

ASLSKPDFKINMPKTRDVYIYMPARMSLIFSTVASFSFVDLETGEINKPFTFSAAYPLDVKNGEIYLS

NGIALSDDFRSFKINNSTISVNSIIEINSIKQGEYKITPIDDMAQFYIFYLKDSTIPYAQFILMDKTMFNS

AYVQMFFLGNYDKNLYDLVINARDAKVFKLKI

PglB from Campylobacter_coli_76339.3S CDG57218

SEQ ID NO: 13

MLKKEYFKNPTFILLTLIILAYAFSVLCRFYWVFWASEFNEYFFNNELMIISNDGYAFAEGARDMIA

GFHQPNDLSYYGSSLSTLTYWFYKITPFSLESIFIYISTFLSSLVVVPLILIANEYKRPLMGFVAALLASI

ANSYYNRTMSGYYDTDMLVIVLAMMIVFFMIRLILRKDLLSLIALPLFVGIYLWWYPSSYTLNVAL

LGLLFIYTLVFHIKEKTLYMAIILASITLSNIAWFYQSAIIVILFSLFVLQNKRFSFALLGFLGLATLVFL

ILSGGVDPILYQLKFYIFRSDESANLAQGFMYFNVNQTIQEVESIDLSIFMKRISGSELVFFISLIGFIFL

VRKHKSMILALPMLALGFLALKGGLRFTIYAVPVLALGFGFLMSLLQERKWKNKNIYWASVSIFTF

LSLLPMFYHIINYKAPTVFSQNEASKLDELKKIAQREDYVVAWWDYGYPIRYYSDVKTLADGGKH

LGKDNFFPSFILSKDQTAAANMARLSVEYTEKSFYAPSNDILKNDLLKAMMKDYKQNNVDLFLAS

LSKPDFKINTPKTRDVYIYMPARMSLIFSTVASFSFVDLDTGKIDKPFTFSAAYPLDVKNGEIYLSNGI

VLSDDFRSFKINHNTIPVNSIIEVSSIKQGEYKITPIDDTAQFYILYLKDSTIPYAQFILMDKAMFNSAY

VQMFFLGNYDKNLYDLVINTRDTKVFKLKI

PglB from Campylobacter_coli_317_04.ASM25395v3 EIA90085

SEQ ID NO: 14

MLKKEYFKNPTFILLAFIILAYVFSVLCRFYWVFWASEFNEYFFNNELMIISNDGYAFAEGARDMIA

GFHQPNDLSYYGSSLSTLTYWFYKITPFSLESIFIYISTFLSSLVVIPLILIANEYKRPLMGFVAALLASI

ANSYYNRTMSGYYDTDMLVIVLAMMIVFFMIRLILKKDLLSLIALPLFVGIYLWWYPSSYTLNVAL

LGLFFIYTLVFHIKEKTLYMAIILASITLSNIAWFYQSAIIVILFSLFVLQNKRFSFALLGILGLATLVFLI

LSGGIDPILYQLKFYIFRSDESANLAQGFMYFNVNQTIQEVESIDLSIFMQRISGSELVFFVSLIGFIFLV

RKHKSMILALPMLALGFLALKSGLRFTIYAVPVLALGFGFLMSLLQERKQKNNNTYWWANIGVFIF

TFLSLIPMFYHINNYKAPTVFSQNEATKLDELKKIAQREDYVVAWWDYGYPIRYYSDVKTLADGG

KHLGKDNFFPSFVLSKDQVAAANMARLSVEYTEKSFYAPLNDILKNDLLQAMMKDYNQNNVDLF

LALLSKPDFKINTPKTRDVYIYMPARMSLIFSTVASFSFVDLGTGEINKPFTFSAAYPLDVKNGEIYLS

NGIVLSDDFRSFKINNSTISVNSIIEINSIKQGEYKITPIDDTAQFYIFYLKDSTIPYAQFILMDKTMFNS

AYVQMFFLGNYDKNLYDLVINARDAKVFKLKF

---

The invention claimed is:

1. An engineered PglB oligosaccharyltransferase (OST) polypeptide comprising an amino acid sequence that is at least 90%, 95%, 96%, 97%, 98%, or 99% identical to the amino acid sequence of SEQ ID NO: 1 or SEQ ID NO: 2 wherein the engineered PglB OST polypeptide comprises a substitution at the amino acid residue corresponding to the amino acid at position 57 of the amino acid sequence of SEQ ID NO: 1, wherein said substitution is to R, K or T and at least one substitution at an amino acid residue at a position selected from the group consisting of R63, Y77, Y78, A84, P94, I101, M155, I172, D176, L191, W193, L233, S234, Q255, Y286, F293, S295, N300, L301, M306, F308, N311, N319, V397, Q402, Y425, Q435, N446, Y462, V464, H479, T523, D532, D601, G605, E606, S610, Y645, K676, and N695, wherein said position(s) correspond to the amino acid sequence of SEQ ID NO:1, and wherein the engineered PglB OST polypeptide increases the yield of glycosylation of a protein with a saccharide by at least 1.5 fold compared to a corresponding PglB OST polypeptide comprising the amino acid sequence of SEQ ID NO:1.

2. The engineered PglB OST polypeptide of claim 1, wherein said at least one substitution is selected from the group consisting of: Y78T, A84W, M155Q, F293C, N300L, L301P, L301G, M306H, F308W, Y462W, Y462N, Y462T, V464L, H479M, T523R, L570R, and L570V.

3. The engineered PglB OST polypeptide of claim 1 wherein said at least one substitution is selected from the group consisting of: L301P, F308W, Y462W, Y462N, and H479M.

4. The engineered PglB OST polypeptide of claim 1 comprising at least 2, 3, 4, 5, or 6 substitutions selected from the group consisting of: N300L, L301P, F308W, Y462W, H479M, and L570R.

5. The engineered PglB OST polypeptide of claim 1, comprising the substitutions Y77R and N311V.

6. The engineered PglB OST polypeptide of claim 1, comprising the substitutions A57R, Y462W, and H479M.

7. The engineered PglB OST polypeptide of claim 1 wherein the engineered PglB OST polypeptide is full length with a length of 712, 713, or 714 amino acids.

8. A *Campylobacter coli* PglB comprising the amino acid sequence of SEQ ID NO: 12, with the exception of a substitution at the amino acid residue corresponding to the amino acid at position 57 of the amino acid sequence of SEQ ID NO: 12, wherein said substitution is to R.

9. A process for preparing a glycosylated protein comprising the steps of:

(a) culturing a host cell comprising the engineered PglB OST polypeptide of claim 1 under conditions suitable for the production of proteins; and (b) isolating the glycosylated protein from the host cell.

* * * * *